US008592368B2

(12) United States Patent
Mohapatra

(10) Patent No.: US 8,592,368 B2
(45) Date of Patent: Nov. 26, 2013

(54) JAK/STAT INHIBITORS AND MAPK/ERK INHIBITORS FOR RSV INFECTION

(75) Inventor: Shyam S. Mohapatra, Tampa, FL (US)

(73) Assignee: University of South Florida, Tampa, FL (US)

( * ) Notice: Subject to any disclaimer, the term of this patent is extended or adjusted under 35 U.S.C. 154(b) by 1848 days.

(21) Appl. No.: 11/018,954

(22) Filed: Dec. 20, 2004

(65) Prior Publication Data
US 2005/0159385 A1 Jul. 21, 2005

Related U.S. Application Data

(60) Provisional application No. 60/531,052, filed on Dec. 19, 2003.

(51) Int. Cl.
A61K 38/00 (2006.01)
A61K 39/395 (2006.01)
A61K 48/00 (2006.01)

(52) U.S. Cl.
USPC .......... 514/3.7; 514/7.5; 514/44 A; 514/44 R; 424/146.1

(58) Field of Classification Search
USPC ...................................... 424/130.1
See application file for complete search history.

(56) References Cited

U.S. PATENT DOCUMENTS

| 4,937,232 | A | 6/1990 | Bell et al. |
| 4,990,519 | A | 2/1991 | Jones et al. |
| 5,141,957 | A | 8/1992 | Jiang et al. |
| 5,204,370 | A | 4/1993 | Jiang et al. |
| 5,216,014 | A | 6/1993 | Jiang et al. |
| 5,270,310 | A | 12/1993 | Bell et al. |
| 5,461,146 | A | 10/1995 | Lewis et al. |
| 5,481,003 | A | 1/1996 | Gillig et al. |
| 5,488,167 | A | 1/1996 | Hudlicky |
| 5,491,242 | A | 2/1996 | Gillig et al. |
| 5,545,636 | A | 8/1996 | Heath, Jr. et al. |
| 5,578,590 | A | 11/1996 | Grunicke et al. |
| 5,616,577 | A | 4/1997 | Nambi et al. |
| 5,621,098 | A | 4/1997 | Heath, Jr. et al. |
| 5,621,101 | A | 4/1997 | Lewis et al. |
| 5,744,166 | A | 4/1998 | Illum |
| 5,783,405 | A | 7/1998 | Mochly-Rosen et al. |
| 5,882,927 | A | 3/1999 | Bennett et al. |
| 5,962,445 | A | 10/1999 | Stewart |
| 6,107,327 | A | 8/2000 | Jirousek et al. |
| 6,153,599 | A | 11/2000 | Dean et al. |
| 6,235,723 | B1 | 5/2001 | Dean |
| 6,258,831 | B1 | 7/2001 | Camden |
| 6,489,306 | B2 | 12/2002 | Mohapatra et al. |
| 6,900,299 | B1 | 5/2005 | Mohapatra et al. |
| 7,118,888 | B2 | 10/2006 | Mohapatra et al. |
| 7,354,908 | B2 | 4/2008 | Mohapatra et al. |
| 2001/0006951 | A1 | 7/2001 | Mohapatra et al. |
| 2002/0165158 | A1 | 11/2002 | King |
| 2003/0060469 | A1 | 3/2003 | Ludwig et al. |
| 2003/0068333 | A1 | 4/2003 | Mohapatra et al. |
| 2003/0138407 | A1 | 7/2003 | Lu et al. |
| 2003/0148989 | A1 | 8/2003 | Bennett et al. |
| 2003/0198624 | A1 | 10/2003 | Mohapatra et al. |
| 2004/0009152 | A1 | 1/2004 | Mohapatra et al. |
| 2004/0014049 | A1 | 1/2004 | Cowsert et al. |
| 2004/0048861 | A1 | 3/2004 | Bemis et al. |
| 2004/0082631 | A1 | 4/2004 | Hale et al. |
| 2004/0175384 | A1 | 9/2004 | Mohapatra et al. |
| 2004/0209799 | A1 | 10/2004 | Vasios |
| 2004/0248082 | A1 | 12/2004 | Scallon |
| 2005/0158327 | A1 | 7/2005 | Mohapatra et al. |
| 2005/0266093 | A1 | 12/2005 | Mohapatra |
| 2005/0272650 | A1 | 12/2005 | Mohapatra |
| 2006/0239971 | A1 | 10/2006 | Mohapatra |
| 2006/0276382 | A1 | 12/2006 | Mohapatra |
| 2007/0009951 | A1 | 1/2007 | Mohapatra et al. |
| 2007/0238676 | A1 | 10/2007 | Mohapatra et al. |
| 2007/0265204 | A1 | 11/2007 | Mohapatra et al. |
| 2008/0070858 | A1 | 3/2008 | Mohapatra |
| 2008/0175832 | A1 | 7/2008 | Mohapatra et al. |
| 2008/0214437 | A1 | 9/2008 | Mohapatra et al. |

(Continued)

FOREIGN PATENT DOCUMENTS

WO   WO 93/20101 A1   10/1993
WO   WO 94/29455 A1   12/1994

(Continued)

OTHER PUBLICATIONS

Yura et al., Effects of protein tyrosine kinase inhibitors on the replication of herpes simplex virus and the phosphorylation of viral proteins Intervirology: Jan./Feb. 1997. vol. 40, Iss. 1; p. 7-14.*
U.S. Appl. No. 11/079,834, filed Mar. 14, 2005, Mohapatra et al.
U.S. Appl. No. 10/526,584, filed Mar. 3, 2005, Mohapatra.
Aringer, M. et al. "Janus kinases and their role in growth and disease" Life Sci., 1999, 64(24):2173-2186.
Barber, S.A. et al. "Visna virus-induced activation of MAPK is required for virus replication and correlates with virus-induced neuropathology" J. Virol., 2002, 76:817-828.
Behera, A.K. et al. "Respiratory syncytial virus induces the expression of 5-lipoxygenase and endothelin-1 in bronchial epithelial cells" Biochem. Biophys. Res. Commun., 1998, 251(3):704-709.
Behera, A.K. et al. "Blocking intercellular adhesion molecule-1 on human epithelial cells decreases respiratory syncytial virus infection" Biochem. Biophys. Res. Commun., 2001, 280(1):188-195.

(Continued)

Primary Examiner — Mary E Mosher
Assistant Examiner — Myron Hill
(74) Attorney, Agent, or Firm — Saliwanchik, Lloyd & Eisenschenk

(57) ABSTRACT

The present invention concerns a method for treating or reducing the likelihood of developing a respiratory syncytial virus (RSV) infection in a subject by administering an effective amount of an inhibitor of the janus kinase (JAK)/signal transducer and activator of transcription (STAT) signaling pathway or the mitogen-activated kinase (MAPK)/extracellular signal-regulated kinase (ERK1/2) signaling pathway to the subject. Another aspect of the invention concerns a pharmaceutical composition that includes an inhibitor of JAK/STAT or MAPK/ERK signaling to the subject; and a pharmaceutically acceptable carrier. Another aspect of the invention concerns a method for identifying agents useful for treating or reducing the likelihood of developing an RSV infection.

27 Claims, 17 Drawing Sheets

(56) References Cited

U.S. PATENT DOCUMENTS

| | | | |
|---|---|---|---|
| 2008/0214494 | A1 | 9/2008 | Mohapatra et al. |
| 2008/0249057 | A1 | 10/2008 | Mohapatra et al. |
| 2009/0176706 | A1 | 7/2009 | Mohapatra |
| 2009/0226423 | A1 | 9/2009 | Mohapatra et al. |
| 2011/0052558 | A1 | 3/2011 | Mohapatra et al. |

FOREIGN PATENT DOCUMENTS

| | | |
|---|---|---|
| WO | WO 98/53103 A1 | 11/1998 |
| WO | WO 00/50062 | 8/2000 |
| WO | WO 03/028759 A1 | 4/2003 |
| WO | WO 03/070983 A1 | 8/2003 |
| WO | WO 2004/074314 A2 | 9/2004 |
| WO | WO 2004/076664 A2 | 9/2004 |
| WO | PCT/US2004/040727 | 12/2004 |

OTHER PUBLICATIONS

Bitko, V. and Barik, S. "Persistent activation of RelA by respiratory syncytial virus involves protein kinase C, underphosphorylated I↓Bβ, and sequestration of protein phosphatase 2A by the viral phosphoprotein" *J. Virol.*, 1998, 72(7):5610-5618.

Bitko, V. et al. "Transcriptional induction of multiple cytokines by human respiratory syncytial virus requires activation of NF-κB and is Inhibited by sodium salicylate and aspirin"*Virology*, 1997, 232(2):369-378.

Bourgeois, C. et al. "Heparin-like structures on respiratory syncytial virus are Involved in its infectivity in vitro" *J. Virol.*, 1998, 72:7221-7227.

Bruder, J.T. and Kovesdi, I. "Adenovirus infection stimulates the Raf/MAPK signaling pathway and induces interleukin-8 expression" *J. Virol.*, 1997, 71(1):398-404.

Brunet, A. et al. "Nuclear translocation of p42/p44 mitogen-activated protein kinase is required for growth factor-induced gene expression and cell cycle entry" *EMBO J.*, 1999, 18:664-674.

Cameron, R. et al. "Identification of contaminating adenovirus type 1 in the ATCC reference strain of respiratory syncytial virus A2 (VR-1302)" *Virus Res.*, 2003, 92:151-156.

Cartier, C. et al. "Association of ERK2 mitogen-activated protein kinase with human immunodeficiency virus particles" *J. Virol.*, 1997, 71:4832-4837.

Chen, W. et al. "Activation of ERK2 by respiratory syncytial virus in A549 cells is linked to the production of interleukin 8" *Exp. Lung Res.*, 2000, 26:13-26.

Cremer, I. et al. "A non-classical ISRE/ISGF3 pathway mediates induction of RANTES gene transcription by type I IFNs" *FEBS Lett.*, 2002, 511(1-3):41-45.

Cruz, M.T. et al. "LPS induction of IκB-α degradation and iNOS expression in a skin dendritic cell line is prevented by the janus kinase 2 inhibitor, tyrphostin B42" *Nitric Oxide*, 2001, 5:53-61.

De Magalhaes, J.C. et al. "A mitogenic signal triggered at an early stage of vaccinia virus infection" *J. Biol. Chem.*, 2001, 276:38353-38360.

De Vos, J. et al. "JAK2 tyrosine kinase inhibitor tyrphostin AG490 downregulates the mitogen-activated protein kinase (MAPK) and signal transducer and activator of transcription (STAT) pathways and induces apoptosis in myeloma cells" *Br. J. Haematol.*, 2000, 109:823-828.

Dudley, D.T. et al. "A synthetic inhibitor of the mitogen-activated protein kinase cascade" *Proc. Natl. Acad. Sci. USA*, 1995, 92:7686-7689.

Durbin, J.E. et al. "Targeted disruption of the mouse Stat1 gene results in compromised innate immunity to viral disease" *Cell*, 1996, 84(3):443-450.

Eckmann, L. et al. "Analysis by high density cDNA arrays of altered gene expression in human intestinal epithelial cells in response to infection with the invasive enteric bacteria *Salmonella*" *J. Biol. Chem.*, 2000, 275(19):14084-14094.

Elias, J.A. et al. "Epithelial interleukin-11" *J. Biol. Chem.*, 1994, 269(35):22261-22268.

Favata, M.F. et al. "Identification of a novel inhibitor of mitogen-activated protein kinase kinase" *J. Biol. Chem.*, 1998,273:18623-18632.

Feldman, S.A. et al. "Human respiratory syncytial virus surface glycoproteins F, G and SH form an oligomeric complex"*Arch. Virol.*, 2001, 146:2369-2383.

Feldman, S.A. et al. "Identification of a linear heparin binding domain for human respiratory syncytial virus attachment glycoprotein G" *J. Virol.*, 1999, 73(8):6610-6617.

Fiedler, M.A. et al. "Inhibition of viral replication reverses respiratory syncytial virus-induced NF-κB activation and interleukin-8 gene expression in A549 cells" *J. Virol.*, 1996, 70(12):9079-9082.

Garcia, R. et al. "Constitutive activation of Stat3 in fibroblasts transformed by diverse oncoproteins and in breast carcinoma cells" *Cell Growth Differ.*, 1997, 8:1267-1276.

Garofalo, R. et al. "Respiratory syncytial virus infection of human respiratory epithelial cells up-regulates class I MHC expression through the induction of IFN-β and IL-1α" *J. Immunol.*, 1996, 157(6):2506-2513.

Garofalo, R. et al. "Transcriptional activation of the interleukin-8 gene by respiratory syncytial virus infection in alveolar epithelial cells: nuclear translocation of the RelA transcription factor as a mechanism producing airway mucosal inflammation" *J. Virol.*, 1996, 70(12):8773-8781.

Improta, T. and Pine, R. "Susceptibility to virus infection is determined by a stat-mediated response to the autocrine effect" *Cytokine*, 1997, 9(6):383-393.

Jahnke, A. and Johnson, J.P. "Synergistic activation of intercellular adhesion molecule 1 (ICAM-1) by TNF-α and IFN-γ is mediated by p65/p50 and p65/c-Rel and interferon-responsive factor Stat1α (p91) that can be activated by both IFN-γ and IFN-α" *FEBS Lett.*, 1994, 354:220-226.

Jamaluddin, M. et al. "The major component of IκBα proteolysis occurs independently of the proteasome pathway in respiratory syncytial virus-infected pulmonary epithelial cells" *J. Virol.*, 1998, 72(6):4849-4857.

Karger, A. et al. "Recombinant bovine respiratory syncytial virus with deletions of the G or SH genes: G and F proteins bind heparin" *J. Gen. Virol.*, 2001, 82:631-640.

Kelemen, B.R. et al. "Selective in vivo inhibition of mitogen-activated protein kinase activation using cell-permeable peptides" *J. Biol. Chem.*, 2002, 277:8741-8748.

Knockaert, M. et al. "p42/p44 MAPKs are intracellular targets of the CDK inhibitor purvalanol" *Oncogene*, 2002, 21:6413-6424.

Kong, X. et al. "Respiratory syncytial virus infection activates STAT signaling in human epithelial cells" *Biochem. Biophys. Res. Commun.*, 2003, 306:616-622.

Lackey, K. et al. "The discovery of potent cRaf1 kinase inhibitors" *Bioorg. Med. Chem. Lett.*, 2000, 10:223-226.

Lewis, T.S. et al. "Signal transduction through MAP kinase cascades" *Adv. Cancer Res.*, 1998, 74:49-139.

Li, J-D. et al. "Activation of NF-κB via a Src-dependent Ras-MAPK-pp90rsk pathway is required for *Pseudomonas aeruginosa*-induced mucin overproduction in epithelial cells" *Proc. Natl. Acad. Sci. USA*, 1998, 95:5718-5723.

Liu, N.Q. et al. "Human immunodeficiency virus type 1 enters brain microvascular endothelia by macropinocytosis dependent on lipid rafts and the mitogen-activated protein kinase signaling pathway" *J. Virol.*, 2002, 76:6689-6700.

Ludwig, S. et al. "Influenza-virus-induced signaling cascades: targets for antiviral therapy?" *Trends Mol. Med.*, 2003, 9:46-52.

Lund, T.C. et al. "Activation of STAT transcription factors by herpesvirus saimiri Tip-484 requires p56$^{lck}$" *J. Virol.*, 1997, 71(9):6677-6682.

Lyons, J.F. et al. "Discovery of a novel Raf kinase inhibitor" *Endocrine-Related Cancer*, 2001, 8:219-225.

Matsuse, H. et al. "Recurrent respiratory syncytial virus infections in allergen-sensitized mice lead to persistent airway inflammation and hyperresponsiveness" *J. Immunol.*, 2000, 164(12):6583-6592.

Molden, J. et al. "A Kaposi's sarcoma-associated herpesvirus-encoded cytokine homolog (vIL-6) activates signaling through the shared gp130 receptor subunit" *J. Biol. Chem.*, 1997, 272(31):19625-19631.

(56) References Cited

OTHER PUBLICATIONS

Monia, B.P. et al. "Antitumor activity of a phosphorothioate antisense oligodeoxynucleotide targeted against C-raf kinase" *Nat. Med.*, 1996, 2(6):668-675.
Pages, G. et al. "Mitogen-activated protein kinases $p42^{mapk}$ and $p44^{mapk}$ are required for fibroblast proliferation" *Proc. Natl. Acad. Sci.* USA, 1993, 90:8319-8323.
Panteva, M. et al. "Hepatitis viruses and the MAPK pathway: is this a survival strategy?" *Virus Res.*, 2003, 92:131-140.
Pazdrak, K. et al. "MAPK activation is involved in post-transcriptional regulation of RSV-induced RANTES gene expression" *Am. J. Physiol. Lung Cell Mol. Physiol.*, 2002, 283:L364-L372.
Pearson, G. et al. "Mitogen-activated protein (MAP) kinase pathways: regulation and physiological functions" *Endocr. Rev.*, 2001, 22:153-183.
Planz, O. et al. "MEK-specific inhibitor U0126 blocks spread of borna disease virus in cultured cells" *J. Virol.*, 2001, 75:4871-4877.
Pleschka, S. et al. "Influenza virus propagation is impaired by inhibition of the Raf/MEK/ERK signaling cascade" *Nat. Cell Biol.*, 2001, 3:301-305.
Quandt, K. et al. "Matind and Matinspector new fast and versatile tools for detection of consensus matches in nucleotide sequence data" *Nucleic Acids Res.*, 1995, 23:4878-4884.
Roy, J. et al. "Intercellular adhesion molecule-1 (ICAM-1) gene expression in human T cells is regulated by phosphotyrosyl phosphatase activity" *J. Biol. Chem.*, 2001, 276(18):14553-14561.
Sampath, D. et al. "Constitutive activation of an epithelial signal transducer and activator of transcription (STAT) pathway in asthma" *J. Clin. Invest.*, 1999, 103(9):1353-1361.
Seger, R. et al. "The MAPK signaling cascade" *FASEB J.*, 1995, 9:726-735.
Sepolt-Leopold, J.S. et al. "Blockade of the MAP kinase pathway suppresses growth of colon tumors in vivo" *Nat. Med.*, 1999, 5:810-816.
Shrikant P. et al. "HIV glycoprotein 120 enhances intercellular adhesion molecule-1 gene expression in glial cells" *J. Immunol.*, 1996, 156(3):1307-1314.
Stancato, L.F. et al. "Activation of Raf-1 by interferon γ and oncostatin M requires expression of the Stat1 transcription factor" *J. Biol. Chem.*, 1998, 273:18701-18704.
Techaarpornkul, S. et al. "Respiratory syncytial virus with the fusion protein as its only viral glycoprotein is less dependent on cellular glycosaminoglycans for attachment than complete virus" *Virology*, 2002, 294:296-304.
Turkson, J. et al. "STAT proteins: novel molecular targets for cancer drug discovery" *Oncogene*, 2000, 19:6613-6626.
Weber-Nordt, R.M. et al. "Constitutive activation of STAT proteins in primary lymphoid and myeloid leukemia cells and in Epstein-Barr virus (EBV)-related lymphoma cells lines" *Blood*, 1996, 88(3):809-816.
Yamamura, Y. et al. "Erythropoietin and friend virus gp55 activate different JAK/STAT pathways through the erythropoietin receptor in erythroid cells" *Mol. Cell Biol.*, 1998, 18(3):1172-1180.
Yang, X. and Gabuzda, D. "Regulation of human immunodeficiency virus type 1 infectivity by the ERK mitogen-activated protein kinase signaling pathway" *J. Virol.*, 1999, 73:3460-3466.
Zhu, H. et al. "Cellular gene expression altered by human cytomegalovirus: global monitoring with oligonucleotide arrays" *Proc. Natl. Acad. Sci.* USA, 1998, 95(24):14470-14475.
Akira, S. "Functional roles of STAT family proteins: lessons from knockout mice" *Stem Cells*, 1999, 17:138-146.
Cheng, H.Y. et al. "Arsenic inhibition of the JAK-STAT pathway" *Oncogene*, 2004, 3:3603-3612.
Espinos, E. et al. "Cooperation between phosphorylation and acetylation processes in transcriptional control" *Mol. Cell. Biol.*, 1999, 19:3474-3484.
Garofalo, R.P. "Mechanisms of eosinophil activation by RSV" National Institute of Allergy and Infections Diseases, grant application abstract, Computer Retrieval of Information on Scientific Projects (CRISP) biomedical database, 2002.
Hirayama, E. et al. "Ras/MAP kinase pathway is associated with the control of myotube formation but not myofibril assembly in quail myoblasts transformed with Rous sarcoma virus" *Cell Structure and Function*, 2001, 26:253-261.
Kawazoe, Y. et al. "Signal transducer and activator of transcription (STAT)-induced STAT inhibitor 1 (SSI-1)/suppressor of cytokine signaling 1 (SOCS1) inhibits insulin signal transduction pathway through modulating insulin receptor substrate 1 (IRS-1) phosphorylation" *J. Exp. Med.*, 2001, 193:263-269.
Kong, X. et al. "ERK-1/2 activity is required for efficient RSV infection" *FEBS Letters*, 2004, 559:33-38, published online Jan. 21, 2004.
Liu, X. et al. "Human immunodeficiency virus type 1 (HIV-1) Tat induces nitric-oxide synthase in human astroglia" *J. Biol. Chem.*, 2002, 277:39312-39319.
Monick, M.M. et al. "Respiratory syncytial virus infection results in activation of multiple protein kinase C isoforms leading to activation of mitogen-activated protein kinase" *J. Immunol.*, 2001, 166:2681-2687.
Winder, D.G. et al. "ERK plays a regulatory role in induction of LTP by theta frequency stimulation and its modulation by β-adrenergic receptors" *Neuron*, 1999, 24:715-726.
Elliott, M.B. et al. "Recombinant Respiratory Syncytial Viruses Lacking the C-Terminal Third of the Attachment (G) Protein Are Immunogenic and Attenuated In Vivo and In Vitro" *Journal of Virology*, Jun. 2004, pp. 5773-5783, vol. 78, No. 11.
Furuta, Y. et al. "In Vitro and In Vivo Activities of Anti-Influenza Virus Compound T-705" *Antimicrobial Agents and Chemotherapy*, Apr. 2002, pp. 977-981, vol. 46, No. 4.
Miller, A.L. et al. "Respiratory Syncytial Virus-Induced Chemokine Production: Linking Viral Replication to Chemokine Production In Vitro and In Vivo" *The Journal of Infectious Diseases*, 2004, pp. 1419-1430, vol. 189.
Ojwang, J.O. et al. "A novel inhibitor of respiratory syncytial virus isolated from ethnobotanicals" *Antiviral Research*, 2005, pp. 163-172, vol. 68.
Richardson, J.Y. et al. "Respiratory Syncytial Virus (RSV) Infection Induces Cyclooxygenase 2: A Potential Target for RSV Therapy" *The Journal of Immunology*, 2005, pp. 4356-4364, vol. 174.
Tsutsumi, H. et al. "Respiratory syncytial virus infection of human respiratory epithelial cells enhances inducible nitric oxide synthase gene expression" *Journal of Leukocyte Biology*, 1999, pp. 99-104, vol. 66.
Weiss, W.J. et al. "Inhalation efficacy of RFI-641 in an African green monkey model of RSV infection" *Journal of Medical Primatology*, 2003, pp. 82-88, vol. 32.
Wyde, P.R. et al. "Antiviral efficacy of VP14637 against respiratory syncytial virus in vitro and in cotton rats following delivery by small droplet aerosol" *Antiviral Research*, 2005, pp. 18-26, vol. 68.
Behera, A.K. et al. "Adenovirus-Mediated Interferon γ Gene Therapy for Allergic Asthma: Involvement of Interleukin 12 and STAT4 Signaling" *Human Gene Therapy*, Sep. 2002, pp. 1697-1709, vol. 13.
Behera, A.K. et al. "2'-5' Oligoadenylate Synthetase Plays a Critical Role in Interferon-γ Inhibition of Respiratory Syncytial Virus Infection of Human Epithelial Cells" *The Journal of Biological Chemistry*, Jul. 2002, pp. 25601-25608, vol. 277, No. 28.
Mohapatra, S. "Mucosal gene expression vaccine: a novel vaccine strategy for respiratory syncytial virus" *The Pediatric Infectious Disease Journal*, Feb. 2003, pp. S100-S104, vol. 22, No. 2.
Mohapatra, S.S. et al. "Natriuretic peptides and genesis of asthma: An emerging paradigm?" *Journal of Allergy and Clinical Immunology*, 2004, pp. 520-526, vol. 114.
Spann, K.M. et al. "Suppression of the Induction of Alpha, Beta, and Gamma Interferons by the NS1 and NS2 Proteins of Human Respiratory Syncytial Virus in Human Epithelial Cells and Macrophages" *Journal of Virology*, Apr. 2004, pp. 4363-4369, vol. 78, No. 8.
Zhao, C.A. et al. "Inhibition of respiratory syncytial virus replication in cultured cells by RNA-cleaving DNAzyme" *Chinese Journal of Pediatrics*, 2003, pp. 594-597, vol. 41, No. 8, Medline XP002513933 Database accession No. NLM14744382.
Ahmad, S. et al. "Antisense Expression of Protein Kinase C[alpha] Inhibits the Growth and Tumorigenicity of Human Glioblastoma Cells" *Neurosurgery*, Nov. 1994, 35(5):904-909.

(56) References Cited

OTHER PUBLICATIONS

Anderson, R.G.W. "The Caveolae Membrane System" *Annual Review of Biochemistry*, 1998, 67:199-225.
Biotech Week, Isis Pharaceuticals, Inc.; "Results of Affinitak phase III trial in non-small cell lung cancer released" Apr. 9, 2003, pp. 74 (p. 1 of 2).
Brown, G. et al. "Respiratory syncytial virus assembly occurs in GM1-rich regions of the host-cell membrane and alters the cellular distribution of tyrosine phosphorylated caveolin-1" *Journal of General Virology*, 2002, 83:1841-1850.
Brown, G. et al. "Caveolin-1 is incorporated into mature respiratory syncytial virus particles during virus assembly on the surface of virus-infected cells" *Journal of General Virology*, 2002, 83:611-621.
Budge, P. et al. "RhoA-Derived Peptide Dimers Share Mechanistic Properties with Other Polyanionic Inhibitors of Respiratory Syncytial Virus (RSV), Including Disruption of Viral Attachment and Dependence on RSV G" *J. Virol.*, May 2004, 78(10):5015-5022.
Carpenter, L. et al. "Respiratory syncytial virus and TNFalpha induction of chemokine gene expression involves differential activation of Rel A and NF-kappaBI" *BMC Infect. Dis.*, 2002, 2(1):5, 9 pages.
Chakravarthy, B.R. et al. "The Direct Measurement of Protein Kinase C (PKC) Activity in Isolated Membranes Using a Selective Peptide Substrate" *Analytical Biochemistry*, 1991, 196:144-150.
Constantinescu, S. et al. "Effects of protein kinase C inhibitors on viral entry and infectivity" *FEBS*, Nov. 1991, 292(1-2):31-33.
Disatnik, M-H. et al. "Sequential activation of individual PKC isozymes in integrin-mediated muscle cell spreading: a role for MARCKS in an integrin signaling Pathway" *Journal of Cell Science*, 2002, 115:2151-2163.
Duncan, M. et al. "Microbial entry through caveolae: variations on a theme" *Cellular Microbiology*, 2002, 4(12):783-791.
Eichholtz, T. et al. "A Myristoylated Pseudosubstrate Peptide, a Novel Protein Kinase C Inhibitor" *The Journal of Biological Chemistry*, Jan. 25, 1993, 268(3):1982-1986.
Godson, C. et al. "Inhibition of Expression of Protein Kinase C α by Antisense cDNa Inhibits Phorbol Ester-mediated Arachidonate Release" *The Journal of Biological Chemistry*, Jun. 5, 1993, 268(16):11946-11950.
Gower, T. et al. "RhoA is Activated Durinhg Respiratory Syncytial Virus Infection" *Virology*, 2001, 283:188-196.
Hallak, L.K. et al. "Glycosaminoglycan Sulfation Requirements for Respiratory Syncytial Virus Infection" *Journal of Virology*, Nov. 2000, 74(22):10508-10513.
Hannun, Y. et al. "Aminoacridines, Potent Inhibitors of Protein Kinase C" *The Journal of Biological Chemistry*, Apr. 15, 1988, 263(11):5124-5131.
Hannun, Y. et al. "The Adriamycin-Iron(III) Comples is a Potent Inhibitor of Protein Kinase C" *The Journal of Biological Chemistry*, Jun. 15, 1989, 264(17):9960-9966.
Harris, T. et al. "A myristoylated pseudosubstrate peptide inhibitor of protein kinase C: effects on glucose- and carbachol- induced insulin secretion" *Molecular and Cellular Endocrinology*, 1996, 121:133-141.
Henry, S.P. et al. "Toxicological and pharmacokinetic properties of chemically modified antisense oligonucleotide inhibitors of PKC-α and C-*raf* kinase" *Anti-Cancer Drug Design*, 1997, 12:409-420.
Hidaka, H. et al. "Isoquinolinesulfonamides, Novel and Potent Inhibitors of Cyclic Nucleotide Dependent Protein Kinase and Protein Kinase C" *Biochemistry*, 1984, 23:5036-5041.
Kitano, T. et al. "Assay and Purification of Protein Kinase C" *Meth. Enzymol.*, 1986, 124:349-352.
Kobayashi, E. et al. "Calphostin C (UCN-1028C), a Novel Microbial Compound, is a Highly Potent and Specific Inhibitor of Protein Kinase C" *Biochemical and Biophysical Research Communications*, Mar. 15, 1989, 159(2):548-553.
Lehel, C. et al. "A Chemiluminescent Microtiter Plate Assay for Sensitive Detection of Protein Kinase Activity" *Analytical Biochemistry*, 1997, 244:340-346.

Levesque, L. et al. "Antisense Oligonucleotides Targeting Human Protein Kinase C-α Inhibit Phorbol Ester-Induced Reduction of Bradykinin-Evoked Calcium Mobilization in A549 Cells" *Molecular Pharmacology* 1997, 51:209-216.
Liebmann, C. et al. "Regulation of MAP kinase activity by peptide receptor signalling pathway: Paradigms of multiplicity" *Cellular Signalling*, 2001, 13:777-785.
Lu, Z. et al. "Activation of Protein Kinase C Triggers Its Ubiquitination and Degradation" *Mollecular and Cellular Biology*, Feb. 1998, 18(2):839-845.
Malladi, V. et al. "Enteropathogenic *Escherichia coli* outer membrane proteins induce changes in cadherin junctions of Caco-2 cells through activation of PKCα" *Microbes and Infection*, 2004, 6:38-50.
Martinez, I. and Melero, J. "Binding of human respiratory syncytial virus to cells: implication of sulfated cell surface proteoglycans" *Journal of General Virology*, 2000, 81:2715-2722.
McCurdy, L. and Graham, B. "Role of Plasma Membrane Lipid Microdomains in Respiratory Syncytial Virus Filament Formation" *Journal of Virology*, Feb. 2003, 77(3):1747-1756.
Meier, O. et al. "Adenovirus triggers macropinocytosis and endosomal leakage together with its clathrin-mediated uptake" *The Journal of Cell Biology*, Sep. 16, 2002, 158(6):1119-1131.
Messing, R.O. et al. "Chronic Ethanol Exposure Increases Levels of Protein Kinase C δ and ε and Protein Kinase C-mediated Phosphorylation in Cultured Neural Cells" *The Journal of Biological Chemistry*, Dec. 5, 1991, 266(34):23428-23432.
Meyer, T. et al. "A Derivative of Staurosporine (CGP 41 251) Shows Selectivity for Protein Kinase C Inhibition and in vitro Anti-Proliferative as well as in vivo Anti-Tumor Activity" *Int. J. Cancer*, 1989, 43:851-856.
Mineo, C. and Anderson, R. "Potocytosis" *Histochem. Cell Biol.*, 2001, 116:109-118,.
Mochly-Rosen, D. and Gordon, A. "Anchoring proteins for protein kinase C: a means for isozyme selectivity" *FASEB J.*, 1998, 12:35-42.
Nakano, M. et al. "The First Step of Adenovirus Type 2 Disassembly Occurs at the Cell Surface, Independently of Endocytosis and Escape to the Cytosol" *Journal of Virology*, Aug. 2000, 74(15):7085-7095.
Naranatt, P. et al. "Kaposi's Sarcoma-Associated Herpesvirus Induces the Phosphatidylinositol 3-Kinase-PKCζ-MEK-ERK Signalling Pathway in Target Cells Early during Infection: Implications for Infectivity" *Journal of Virology*, Jan. 2003, 77(2):1524-1539.
Parekh, D. et al. "Multiple pathways control protein kinase C phosphorylation" *The EMBO J.*, 2000, 19(4):496-503.
Patil, S.D. et al. "DNA-based Therapeutics and DNA Delivery Systems: A comprehensive Review" *The AAPS Journal*, 2005, 7(1; article 9):E61-E77
Pelkmans, L. et al. "Local Actin Polymerization and Dynamin Recruitment in SV40-Induced Internalization of Caveolae" *Science*, Apr. 2002, 296:535-539.
Prevostel, C. et al. "Protein kinase Cα actively downregulates through caveolae-dependent traffic to an endosomal compartment" *Journal of Cell Science*, 2000, 113:2575-2584.
Razinkov, V. et al. "RFI-641 inhibits entry of respiratory syncytial virus via interactions with fusion protein" *Chemistry & Biology*, 2001, 8:645-659.
Root, C. et al. "Entry of influenza viruses into cells is inhibited by a highly specific protein kinase C inhibitor" *Joural of General Virology* 2000, 81:2697-2705.
San-Juan-Vergara, H. et al. "Protein Kinase C-α Activity Is Required for Respiratory Syncytial Virus Fusion to Human Broncial Epithelial Cells" *Journal of Virology*, Dec. 2004, 78(24):13717-13726.
Schechtman, D. and Mochly-Rosen, D. "Isozyme-Specific Inhibtors and Activators of Protein Kinase C" *Methods Enzymol.*, 2002, 345:470-489.
Schwartz, G.K. et al. "A Pilot Clinical/Pharmacological Study of the Protein Kinase C-specific Inhibitor Safingol Alone and in Combination with Doxorubicin" *Clinical Cancer Research*, Apr. 1997, 3:537-543.
Sieczkarski, S. et al. "Role of Protein Kinase C βII in Influenza Virus Entry via Late Endosomes" *Journal of Virology*, Jan. 2003, 77(1):460-469.
Simoes, E.A.F. "Respiratory syncytial virus infection" *The Lancet*, Sep. 4, 1999, 354:847-852.

(56) References Cited

OTHER PUBLICATIONS

Soh, J-W. et al. "Novel Roles of Specific Isoforms of Protein Kinase C in Activation of the c-*fos* Serum Response Element" *Molecular and Cellular Biology*, Feb. 1999, 19(2):1313-1324.

Souroujon, M.C. and Mochly-Rosen, D. "Peptide modulators of protein-protein interactions in intracellular signaling" *Nature Biotechnology*, Oct. 1998, 16:919-924.

Sukumaran, S. and Prasadarao, N. "Regulation of Protein Kinase C in *Escherichia coli* K1 Invastion of Human Brain Microvascular Endothelial Cells" *The Journal of Biological Chemistry*, Apr. 5, 2002, 277(14):12253-12262.

Tamaoki, T. et al. "Staurosporine, a Potent Inhibitor of Phospholipids/$Ca^{++}$ Dependent Protein Kinase" *Biochemical and Biophysical Research Communications*, Mar. 13, 1986, 135(2):397-402.

Techaarpornkul, S. et al. "Functional Analysis of Recombinant Respiratory Syncytial Virus Deletion Mutants Lacking the Small Hydrophobic and/or Attachment Glycoprotein Gene" *Journal of Virology*, Aug. 2001, 75(15):6825-6834.

Toullec, D. et al. "The Bisindolylmaleimide GF 109203X Is a Potent and Selective Inhibitor of Protein Kinase C" *The Journal of Biological Chemistry*, Aug. 25, 1991, 266(24):15771-15781.

Urbach, V. et al. "Cellular mechanisms for apical ATP effects on intracellular pH in human bronchial epithelium" *Journal of Physiology*, 2002, 543.1:13-21.

Vanderplasschen, A. and Smith, G. "A Novel Virus Binding Assay Using Confocal Microscopy: Demonstration that the Intracellular and Extracellular Vaccinia Virions Bind to Different Cellular Receptors" *Journal of Virology*, May 1997, 71(5):4032-4041.

Vanderplasschen, A. et al. "Intracellular and extracellular vaccinia virions enter cells by different mechanisms" *Journal of General Virology*, 1998, 79:877-887.

Villalba, M. et al. "Vav1/Rac-dependent actin cytoskeleton reorganization is required for lipid raft clustering in T cells" *The Journal of Cell Biology*, Oct. 29, 2001, 155(3):331-338.

Wagner, S. et al. "Analysis of the Subcellular Distribution of Protein Kinase Cα Using PKC-GFP Fusion Proteins" *Experimental Cell Research*, 2000, 258:204-214.

Wanaski, S. et al. "Caveolin Scaffolding Region and the Membrane Binding Region of Src Form Lateral Membrane Domains" *Biochemistry*, 2003, 42:42-56.

Wang, Y. et al. "Metabolic Stress Opens $K^+$ Channels in Hepatoma Cells through a $Ca^{2+}$-and Protein Kinase Cα-dependent Mechanism" *The Journal of Biological Chemistry*, Jul. 26, 1996, 271(30):18107-18113.

Wyatt, T. et al. "Stimulation of protein kinase C activity by tumor necrosis factor-α in bovine bronchial epithelial cells" *Am. J. Physiol.*, 1997, 273:L1007-1013.

Hayden, F. "Combination antiviral therapy for respiratory virus infections" *Antiviral Research*, 1996, 29:45-48.

Hu, W-Y. et al. "Inhibition of Retroviral Pathogenesis by RNA Interference" *Current Biology*, Aug. 6, 2002, 12:1301-1311.

Marcusson, E.G. et al. "Preclinical and Clinical Pharmacology of Antisense Oligonucleotides" *Molecular Biotechnology*, 1999, 12:1-11.

Nyce, J. "Respirable antisense oligonucleotides: a new, third drug class targeting respiratory disease" *Current Opinion in Allergy and Clinical Immunology*, 2002, 2:533-536.

San-Juan, H.G. et al. "Activation of PKC Isozymes in Normal Human Bronchial Epithelial Cells by Respiratory Syncytial Virus Infection" *J Allergy Clin Immunol*, Jan. 2002, 109:S362, Abstract No. 1128.

Zhang, Y. et al. "Ribavirin Treatment Up-Regulates Antiviral Gene Expression via the Interferon-Stimulated Response Element in Respiratory Syncytial Virus-Infected Epithelial Cells" *Journal of Virology*, May 2003, 77(10):5933-5947.

Burdelya, L. et al. "Combination Therapy with AG-490 and Interleukin 12 Achieves Greater Antitumor Effects than Either Agent Alone" *Molecular Cancer Therapeutics*, Sep. 2002, 1:893-899.

Galan, A. et al. "Extracellular signaling-regulated kinase-1 and -2 (ERK 1/2) mediate referred hyperalgesia in a murine model of visceral pain" *Molecular Brain Research*, 2003, 116:126-134.

Salzmann, J. et al. "Importance of ERK activation in behavioral and biochemical effects induced by MDMA in mice" *British Journal of Pharmacology*, 2003, 140:831-838.

Wang, Z. et al. "Effects of extracellular signal-regulated kinase (ERK) on focal cerebral ischemia" *Chinese Medical Journal*, 2003, 116(10):1497-1503.

Miller, A.L. et al. "CXCR2 Regulates Respiratory Syncytial Virus-Induced Airway Hyperreactivity and Mucus Overproduction" *The Journal of Immunology*, 2003, 170:3348-3356.

Office Action dated Dec. 14, 2011 in U.S. Appl. No. 12/384,384, filed Apr. 3, 2009.

Office Action dated May 28, 2013 in U.S. Appl. No. 12/384,384, filed Apr. 3, 2009.

San-Juan-Vergara, HG et al. "Inhibition of PKC-Alpha Activity Blocks Respiratory Syncytial Virus Infection" *Journal of Allergy and Clinical Immunology*, 113(2):S196, Abstract 681, 2004.

Wetsel, W.C. et al. "Tissue and Cellular Distribution of the Extended Family of Protein Kinase C Isoenzymes" *The Journal of Cell Biology*, Apr. 1992, 117(1):121-133.

\* cited by examiner

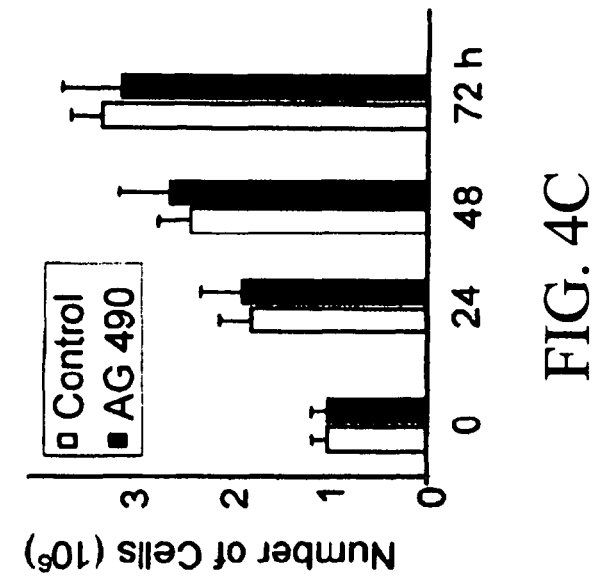
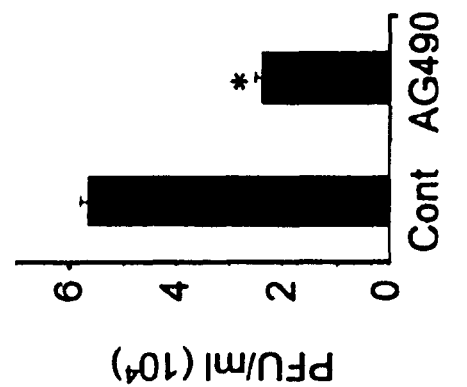
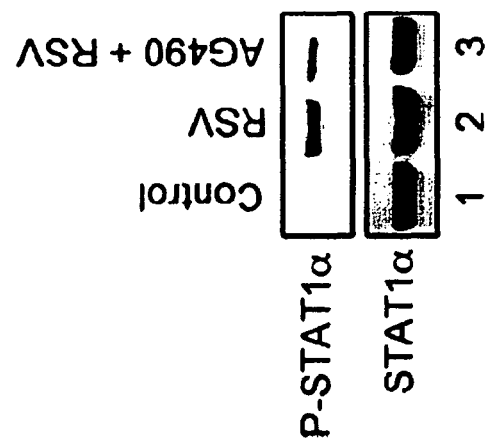
FIG. 4C
FIG. 4B
FIG. 4A

JAK/STAT INHIBITORS AND MAPK/ERK INHIBITORS FOR RSV INFECTION

CROSS-REFERENCE TO RELATED APPLICATION

The present application claims the benefit of U.S. Application Ser. No. 60/531,052, filed Dec. 19, 2003, which is hereby incorporated by reference herein in its entirety, including any figures, tables, nucleic acid sequences, amino acid sequences, and drawings.

BACKGROUND OF THE INVENTION

Respiratory syncytial virus (RSV) is a respiratory pathogen that produces annual epidemics of respiratory illness primarily in infants, but also in adults (Murry, A. R. and Dowell, S. F., Respiratory syncytial virus: not just for kids, Hosp. Pract. (Off. Ed.), 1997, 32(7): 87-88, 91-94, 98 passim; Centers for Disease Control and Prevention, Update: respiratory syncytial virus activity—United States, 1995-96 Season, *JAMA*, 1996, 275(1): 29). RSV causes bronchiolitis and exacerbates asthma and may also lead to life-threatening respiratory conditions resulting in prolonged hospitalization and death in high-risk individuals (Armstrong, D. S. and Menahem, S. *J. Paediatr. Child Health*, 1993, 29(4): 309-311; Fiedler, M. A. et al. *J. Virol.*, 1996, 70(12): 9079-9082; Jeng, M. J. and Lemen, R. J. *Am. Fam. Physician*, 1997, 55(4): 1139-1146, 1149-1150).

RSV infection upregulates the expression of IL-1, IL-6, IL-8, TNF-, MIP1, RANTES, and ICAM-1 in epithelial cells, which are the main targets of RSV infection in vivo (Garofalo, R. et al. *J. Immunol.*, 1996, 157(6): 2506-2513; Behera, A. K. et al. *Biochem. Biophys. Res. Commun.*, 2001, 280(1): 188-195; Bitko, V. et al. *Virology*, 1997, 232(2): 369-378; Elias, J. A. et al. *J. Biol. Chem.*, 1994, 269(35): 22261-22268). The elevated expression of these inflammatory molecules in RSV infection has been attributed to activation of nuclear factor-κB (Fiedler, M. A. et al. *J. Virol.*, 1996, 70(12): 9079-9082; Garofalo, R. et al. *J. Virol.*, 1996, 70(12): 8773-8781; Jamaluddin, M. et al. *J. Virol.*, 1998, 72(6): 4849-4857; Bitko, V. and Barik, S. *J. Virol.*, 1998, 72(7): 5610-5618).

The signal transducers and activators of transcription (STATs) mediate responses to diverse cytokine and non-cytokine stimuli, resulting in the altered expression of genes involved in inflammation (Bruder, J. T. and Kovesdi, I. *J. Virol.*, 1997, 71(1): 398-404; Improta, T. and Pine, R. *Cytokine*, 1997, 9(6): 383-393; Durbin, J. E. et al. *Cell*, 1996, 84(3): 443-450). A number of viruses utilize the STAT pathway for gene activation through cell surface binding of viral proteins. Epstein-Barr virus-transformed lymphoblastoid cells and Friend leukemia virus-transformed erythroid cells exhibit a constitutively activated JAK-STAT pathway (Weber-Nordt, R. M. et al. *Blood*, 1996, 88(3): 809-816; Yamamura, Y. et al. *Mol. Cell Biol.*, 1998, 18(3): 1172-1180), and the tyrosine kinase-interacting proteins of herpes virus saimiri and HIV induce the activation of a JAK-STAT cascade (Lund, T. C. et al. *J. Virol.*, 1997, 71(9): 6677-6682; Molden, J. et al. *J. Biol. Chem.*, 1997, 272(31): 19625-19631; Shrikant, P. et al. *J. Immunol.*, 1996, 156(3): 1307-1314). However, STATs have not previously been implicated in RSV infection. It has been shown that RSV infection of epithelial cells leads to the induction of a variety of cytokines, chemokines, and adhesion molecules (Behera, A. K. et al. *Biochem. Biophys. Res. Commun.*, 1998, 251(3): 704-709; Matsuse, H. et al. *J. Immunol.*, 2000, 164(12): 6583-6592). The presence of STAT-1- and AP1-binding sequences in the promoters of RSV-inducible genes (ICAM-1, RANTES, and endothelin-1) (Behera, A. K. et al. *Biochem. Biophys. Res. Commun.*, 2001, 280(1): 188-195) and the report that STAT-1 is constitutively expressed in asthmatics (Sampath, D. et al. *J. Clin. Invest.*, 1999, 103(9): 1353-1361). However, it is not known whether RSV infection may activate STAT-1.

Based on the transfac promoter analysis of RSV-induced early genes identified in microarray studies, the present inventor postulated that RSV activates multiple signaling pathways in epithelial cells (Quandt, K. et al. *Nucleic Acids Res.*, 1995, 23: 4878-4884; Kong, X. et al. *Biochem. Biophys. Res. Commun.*, 2003, 306: 616-622). This analysis revealed binding sites for activator protein-1 suggesting that extracellular signal-regulated kinases (ERKs) may also be involved in early gene expression. ERK-1 and ERK-2 mediate specific responses to diverse stimuli, including viruses, cytokines, and growth factors and hormones (Li, J. D. et al. *Proc. Natl. Acad. Sci. USA*, 1998, 95: 5718-5723; Bruder, J. T. and Kovesdi, I. *J. Virol.*, 1997, 71: 398-404; Jahnke, A. and Johnson, J. P. *FEBS Lett.*, 1994, 354: 220-226; Garcia, R. et al. *Cell Growth Differ.*, 1997, 8: 1267-1276; Improta, T. and Pine, R. *Cytokine*, 1997, 9: 383-393). RSV-induced production of IL-8 and RANTES is dependent on activated ERK-2 (Chen, W. et al. *Exp. Lung Res.*, 2000, 26: 13-26; Pazdrak, K. et al. *Am. J. Physiol., Lung Cell Mol. Physiol.*, 2002, 283:L364-L372). However, the role of ERKs in early signaling responses in RSV infection remains poorly understood. Also, whether interrupting ERK pathways can alter the course of viral infection is not known.

BRIEF SUMMARY OF THE INVENTION

The present invention concerns a method for treating or reducing the likelihood of developing a respiratory syncytial virus (RSV) infection in a subject administering an effective amount of an inhibitor of signal transducer and activator of transcription (STAT) or the extracellular signal-regulated kinase (ERK1/2) signaling pathway to the subject.

Optionally, the method further includes the step of determining whether the subject is suffering from an RSV infection. The determining step can be determined before, during, and/or after the inhibitor is administered to the subject.

Another aspect of the invention concerns a method for treating or reducing the likelihood of RSV infection in cells in vitro, by administering an effective amount of an inhibitor of signal transducers and activators of transcription (STAT) or the extracellular signal-regulated kinase (ERK1/2) signaling pathway to the cells in vitro. The method is useful for carrying out research in vitro.

Another aspect of the invention concerns a method for identifying agents useful for treating or reducing the likelihood of developing an RSV infection by determining whether a candidate agent acts as an inhibitor of signal transducers and activators of transcription (STAT) or ERK1/2 signaling, wherein inhibition of STAT or ERK1/2 signaling is indicative of an agent useful for treating or reducing the likelihood of developing RSV infection. Optionally, the method further includes the step of manufacturing the inhibitor. Optionally, the method further includes the step of formulating the inhibitor for delivery to the respiratory epithelium.

Another aspect of the invention concerns a pharmaceutical composition that includes an inhibitor of signal transducers and activators of transcription (STAT) or ERK1/2 signaling to the subject; and a pharmaceutically acceptable carrier.

BRIEF DESCRIPTION OF THE DRAWINGS

For a fuller understanding of the invention, reference should be made to the following detailed description, taken in connection with the accompanying drawings, in which:

In FIG. 1C, the numbers in parentheses are the fold increases in expression determined by one of two microarray analyses.

FIGS. 2A and 21B show that RSV activates STAT-1α in A549 and NHBE cells. Lysates from uninfected and supRSV-infected A549 and NHBE cells were separated by SDS-PAGE, blotted and probed with anti-phospho-STAT-1α, and then re-probed with anti-STAT-1α. Lysates from uninfected A549 cells (control) and cells exposed to sucrose-purified RSV (purRSV) or sucrose alone (sucrose) for 30 minutes were blotted and probed with anti-phospho-STAT-1α, then re-probed with anti-STAT-1α antibodies. Results are shown in FIG. 2A. A549 and NHBE cells were exposed to sucrose, supRSV, or purRSV at an MOI of 1 for 30 minutes, then stained for phospho-STAT1. Results are shown in FIG. 2B.

FIGS. 4A-4F that blocking STAT-1α attenuates RSV gene transcription and infection. A549 cells were treated with 50 M AG490 for 4 hours before being exposed to supRSV for 30 minutes. Lysates were separated by SDS-PAGE and immunoblotted using antibodies to phospho-STAT-1α and STAT-1α. Results are shown in FIG. 4A. The total number of syncytia-forming plaques (PFU/ml) was counted 72 hours post-infection. Results are shown in FIG. 4B. Each value represents means SEM (N=3, *p<0.001). Cell proliferation was determined by viable cell counts. Results are shown in FIG. 4C. A549 cells were cotransfected with the pRL-TK plasmid and either the WT (pRc/CMV STAT-1α) (lanes 1 and 2) or DN mutant (pRc/CMV STAT-1α) (Y701F) (lanes 3 and 4) and then exposed to supRSV for 30 minutes. Lysates were separated by SDS-PAGE and immunoblotted for phospho-STAT-1α or STAT-1α. Results are shown in FIG. 4D. A549 cells were transfected with WT or DN-STAT-1α constructs and 24 hours later exposed to RSV for 30 minutes. RSV replication was measured by RT-PCR analysis of N protein gene expression. Results are shown in FIG. 4E. The percentage of infected cells was determined using immunofluorescence in cells transfected with WT or DN-STAT-1α. Results are shown in FIG. 4F. The values are means SEM (*p<0.001).

FIGS. 5A-5E1 show that RSV activates STAT-3 in A549 cells through an IL-6-dependent pathway. Lysates of uninfected A549 cells (C) and cells exposed for 30 minutes to two different batches of purRSV (RSV) were blotted and probed first with anti-phospho-STAT-3 or -STAT-5 and then re-probed with anti-STAT-3 or -STAT-5 antibodies. Results are shown in FIG. 5A. Nuclear extracts of uninfected cells (C) or cells infected with RSV for 30, 60, or 120 minutes (RSV) were analyzed by an electrophoretic mobility shift assay for binding to hSIE oligos. Nuclear extract from cells exposed to RSV for 30 minutes (lane 5) was subjected to supershift assay using antibody to STAT-3 (arrow). NIH3T3 (NIH) fibroblasts stimulated with PDGF were used as control. Results are shown in FIG. 5B. A549 cells were transfected with the EGFP reporter gene cloned downstream of the IL-6 promoter (pIL6-EGFP), then 24 hours later were infected with purRSV or supRSV. Results are shown in FIG. 5C, with lane 1, pIL6-EGFP control; lane 2, vector control; lanes 3 and 4, vector control+RSV; lane 5, pIL6-EGFP+purRSV; and lane 6, pIL6-EGFP+supRSV. EGFP expression was measured by flow cytometry. supRSV was incubated with goat serum (C) or anti-IL-6 and used to infect A549 cells. Lysates were blotted and probed for phospho-STAT-3 and -STAT-1α. Results are shown in FIG. 5D. A549 cells were infected with purRSV and total RNA was isolated at 30, 60, and 120 minutes after infection. RT-PCR was done using human IL-6 and β-actin primers. The bands were quantified by densitometry and normalized to β-actin (N=3, *p<0.0001). The results are shown in FIGS. 5E and 5E-1.

In FIG. 6A, RSV exposure induces rapid phosphorylation of ERK-1/2 in A549 cells. Western blots of total proteins extracted from uninfected cells and RSV-infected cells for 5, 10, 15 or 30 minutes and for 1, 4, or 24 hours probed with anti-phospho ERK-1/2, stripped, and then re-probed with anti-ERK-1/2. FIG. 6B shows results of an activity assay of ERK-1/2 immunoprecipitated from 200 μg of total proteins extracted from uninfected cells and sucrose-purified RSV-infected cells.

In FIG. 8A, AG490- or PD98059-treated A549 cells were infected with RSV for 15 minutes. Total proteins were Western-blotted using specific anti-phospho antibodies to STAT-1α, ERK-1/2 or IκBα. Lane 1: mock-infected, lanes 2-4: RSV infected for 30 minutes, lane 3: cells treated with 50 μM of AG490 prior to RSV infection, lane 4: cells treated with 25 μM of PD98059 for 4 hours prior RSV infection. In FIG. 8B, the bands were quantified by densitometry and the relative intensity of phospho-STAT-1α, phospho-ERK and phospho-IκBα with respect to uninfected control (lane 1) was determined. The experiment was repeated twice and the result of a representative experiment is shown. FIG. 8C shows the effect of DN STAT-1α on ERK activation. A549 cells were co-transfected with RL-TK plasmid and either the WT (pRc/CMV-STAT-1α) (lanes 3 and 4) or DN mutant (pRc/CMV-STAT-1α) (Y701F) (lanes 5 and 6) and were infected with RSV for 30 minutes after 24 hours of transfection. Total proteins were extracted and Western-blotted using antibodies to phospho-STAT-1α, phospho-ERK-1/2 and re-probed with antibodies to STAT-1α or ERK-1/2. In FIG. 8D, the bands were quantified by densitometry and the relative intensity of phospho-ERK and ERK was determined in each band. The experiment was repeated twice and the result of a representative experiment is shown.

In FIG. 9A, PD98059- or DMSO-treated A549 cells were infected with RSV. Supernatants were collected from control and treated cells at 72 hours. The RSV titers were determined using a HEP-2 cell-based plaque assay as described. FIG. 9B shows single cell immunofluorescent assays of A549 cells co-transfected with RL-TK plasmid and either the WT (pCMV-HAMEK) or DN mutant (pCMV-HA MEKm). Twenty-four hours after transfection, A549 cells were infected with RSV for 90 minutes and 24 hours after the % of infected cells was determined with FITC-RSV antibody.

BRIEF DESCRIPTION OF THE SEQUENCES

Figure 1B:
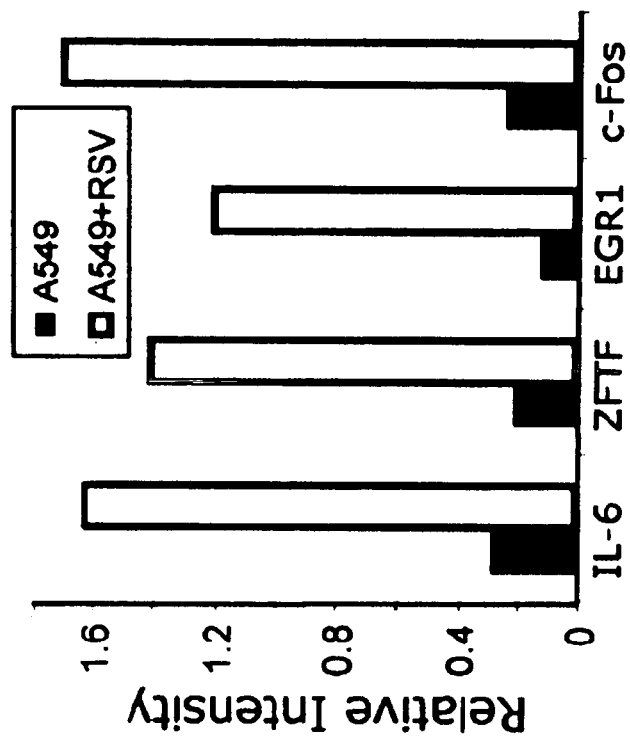
FIGS. 1A-1C show that RSV induces a number of regulatory genes in A549 cells. Cells were exposed to RSV for 30 minutes, total RNA was isolated from both non-infected (C) and supRSV-infected (RSV) cells, and expression of IL-6, the zinc-finger transcription factor (ZFTF), early growth response factor-1 (EGR-1), and the oncogene c-Fos was determined by RT-PCR (FIG. 1A). Densitometry readings were normalized to β-actin. Results are shown in FIG. 1B. Transfac promoter analysis of RSV-activated early genes is shown in FIG. 1C, where SBE, STAT-binding element; κB, nuclear factor κB; AP1, activator protein 1; and IRF-1, interferon regulatory factor-1.

SEQ ID NO: 1 is the forward primer Egr-1-fp.
SEQ ID NO:2 is the reverse primer Egr-1-rp.
SEQ ID NO:3 is the forward primer cFos-fp.
SEQ ID NO: 4 is the reverse primer cFos-rp.
SEQ ID NO: 5 is the forward primer ZFTF-fp.
SEQ ID NO:6 is the reverse primer ZFTF-rp.
SEQ ID NO:7 is the forward primer beta-actin-fp.
SEQ ID NO:8 is the reverse primer beta-actin-rp.
SEQ ID NO:9 is the forward primer IL6-fp.
SEQ ID NO:10 is the reverse primer IL6-rp.
SEQ ID NO:11 is the forward primer RSV N-fp.
SEQ ID NO:12 is the reverse primer RSV N-rp.
SEQ ID NO:13 is the Sis-inducible element SIE.
SEQ ID NO:14 is a peptide inhibitor of ERK1/2 activation.
SEQ ID NOs:15-19 are nuclear localization signals (NLS).

DETAILED DESCRIPTION OF THE INVENTION

The presence of STAT-1- and AP1-binding sequences in the promoters of respiratory syncytial virus (RSV)-inducible genes (ICAM-1, RANTES, and endothelin-1) and the report that STAT-1 is constitutively expressed in asthmatics led the present inventor to hypothesize that RSV infection may activate STAT-1. To test this, A549 NHBE cells were examined for the role of STATs in RSV-induced early gene activation. RSV was found to activate STAT-1 and STAT-3, and activation was necessary for early gene activation and successful infection of epithelial cells.

ERK-1 and ERK-2 mediate specific responses to diverse stimuli, including viruses, cytokines, and growth factors and hormones. RSV-induced production of IL-8 and RANTES is dependent on activated ERK-2. However, the understanding of the role of ERKs in early signaling responses in RSV infection is limited. Also, whether interrupting ERK pathways can alter the course of viral infection was not previously known. In this study, the results demonstrate that both ERK-1 and ERK-2 are rapidly activated in A549 cells upon RSV exposure and that ERK-1/2 activation is required for a successful RSV replication.

The present invention concerns a method for treating or reducing the likelihood of developing an RSV infection in a subject administering an inhibitor of signal transducers and activators of transcription (STAT) or the extracellular signal-regulated kinase (ERK1/2) signaling pathway to the subject.

Optionally, the method further includes the step of determining whether the subject is suffering from an RSV infection. The determining step can be determined before, during, and/or after the inhibitor is administered to the subject.

Another aspect of the invention concerns a pharmaceutical composition that includes an inhibitor of STAT or ERK signaling to the subject; and a pharmaceutically acceptable carrier.

The methods of the present invention are especially useful for treating or reducing the likelihood of RSV infection by the use of an inhibitor of ERK or STAT. As used herein, unless otherwise indicated, the terms "ERK" and "STAT" refer to all known isoforms of the respective enzymes including but not limited to ERK1, ERK2, STAT 1, STAT 2, STAT 3, STAT 4, STAT 5, and STAT 6.

The methods and compositions of the present invention can employ any STAT or ERK inhibitor. A wide variety of suitable inhibitors may be employed, guided by art-recognized criteria such as efficacy, toxicity, stability, specificity, half-life, etc. Information about STAT inhibitors and ERK inhibitors and methods for their preparation are readily available in the art (see, for example, Kohno M. et al., *Progress in Cell Cycle Research,* 2003, 5: 219-224).

A wide variety of cytokines, lymphokines, and growth factors activate (via cytokine receptors) the Janus Kinase (JAK) family (Aringer et al., *Life Sci.,* 1999, 64(24): 2173-2186). Receptor-activated JAK associations proceed to activate (e.g., tyrosine phosphorylate) signal transducers and activators of transcription (STAT) proteins. JAKS are believed to be the principle activators of the STAT proteins (Silvennoinen et al., *APMIS,* 1997, 105: 497-509). A model for STAT activation is that JAKS phosphorylate specific tyrosine residues within the activated cell receptor, creating docking sites to STATs to bind at their Src homology 2 (SH2) domains. JAKS catalyze phosphorylation, activating STAT dimerization and disengaging the STATs from the receptor. STAT dimmers then translocate to the cell nucleus, where thy function as transcription factors, binding to, for example, interferon DNA promoter regions (IRE and GAS) (Darnell, et al., *Science,* 1994, 264: 1415-1421; Ihle, Nature, 1995, Nature, 377: 591-594; Ihle, *TIBS,* 1994, 19: 222-227; Darnell, *Science,* 1997, 277: 1630-1635). Further upstream, JAK activation is directly linked to cellular cytokine transmembrane receptors that lack intrinsic kinase activity. JAKs are capable of binding to the cytoplasmic motifs of these receptors. The cellular receptors act to recruit/activate JAKs as their non-receptor protein kinase, to direct intracellular signaling.

The terms "STAT inhibitor", "JAK inhibitor", and "JAK/STAT inhibitor" are used interchangeably herein to refer to any agent capable of down-regulating or otherwise decreasing or suppressing the amount and/or activity of JAK-STAT interactions. JAK inhibitors down-regulate the quantity or activity of JAK molecules. STAT inhibitors down-regulate the quantity or activity of STAT molecules. Inhibition of these cellular components can be achieved by a variety of mechanisms known in the art, including, but not limited to binding directly to JAK (e.g., a JAK-inhibitor compound binding complex, or substrate mimetic), binding directly to STAT, or inhibiting the expression of the gene, which encodes the cellular components. JAK/STAT inhibitors are disclosed in U.S. patent publication 2004/0209799 (Vasios G.).

Examples of JAK/STAT inhibitors which may be useful in the methods of this invention include, but are not limited to: PIAS proteins, which bind and inhibit at the level of the STAT proteins (Chung et al. *Science*, 1997, 278: 1803-1805); members of an SH2 containing family of proteins, which are able to bind to JAKs and/or receptors and block signaling (see, for example, Aman and Leonard *Current Biology*, 1997, 7:R784-788; Nicholson and Hilton *J. Leukocyte Biol.*, 1998, 63: 665-668); cytokine-inducible Src homology 2-containing (CIS) protein, an inhibitor of STAT signaling (Yoshimura et al. *EMBO J.*, 1995, 14: 2816-2826); CIS-related proteins, which can inhibit STAT signaling or directly bind to Janus kinases (Yoshimura et al. *EMBO J.*, 1995, 14: 2816-2826; Matsumoto et al. *Blood*, 1997, 89: 3148-3154; Starr et al. *Nature*, 1997, 387: 917-921; Endo et al. *Nature*, 1997, 387: 921-924; Naka et al. *Nature*, 1997, 387: 924-929); Suppressor of Cytokine Signaling-I protein (SOCS-1, also referred to as JAB or SSI-1), which appears to associate with all JAKs to block the downstream activation of STAT3 (Ohya et al. *J. Biol. Chem.*, 1997, 272: 27178-27182); Tyrphostins, which are derivatives of benzylidene malononitrile, resembling tyrosine and erbstatin moieties (Gazit et al. *J. Med. Chem.*, 1989, 32: 2344-2352); AG-490, a member of the tyrophostin family of tyrosine kinase inhibitors (Wang et al. *J. Immunol.*, 1999, 162(7): 3897-3904, also Kirken et al. *J. Leukoc. Biol.*, 1999, 65: 891-899); 4,5-dimethoxy-2-nitrobenzoic acid and 4,5-dimethoxy-2-nitrobenzamide, which specifically inhibit JAK3 (Goodman et al. *J. Biol. Chem.*, 1998, 273: 17742-17748); 4-(phenyl)-amino-6,7-dimethoxyquinazoline (parent compound WHI-258) and derivatives of this compound which are structurally-derived from dimethoxyquinazoline compounds (Sudbeck et al. 1999); compounds containing a 4'-OH group, including 4-(4'-hydroxyphenyl)-amino-6,7-dimethoxyquinazoline (WHI-P131), 4-(3'-bromo-4'-hydroxylphenyl)-amino-6,7-dimethoxyquinazoline (WHI-P154), and 4-(3',5'-dibromo-4'-hydroxylphenyl)-amino-6,7-dimethoxyquinazoline (WHI-P97); WHI-P180, another dimethoxyquinazoline compound (Chen et al. *Pharm. Res.*, 1999, 16(1): 117-122); and cAMP elevating agents, such as forskolin, a direct activator of adenylate cyclase and dibutyryl cAMP, and 3-isobutyl-1-methylxanthine (IBMX), an inhibitor of cAMP phosphodiesterase (Kolenko et al. *Blood*, 1999, 93(7): 2308-2318).

In one embodiment of the invention, the STAT inhibitor is one selected from the group consisting of a suppressor of cytokine signaling (SOCS), STAT-induced STAT inhibitor (SSI), JAK binding protein (JAB), and STAT3 interacting protein (StP1) (Turkson J. et al., *Oncogene*, 2000, 19: 6613-6626). In a specific embodiment of the invention, the JAK/STAT inhibitor is AG490, which is a JAK3/STAT, JAK3/AP-1, and JAK3/MAPK signaling pathway inhibitor, and also blocks JAK3 autophosphorylation (Kirken R. A. et al., *J. Leukoc. Biol.*, 1999, 65: 891-899; Wang L. H. et al., *J. Immunol.*, 1999, 162: 3897-3904; and De Vos J. et al., *Br. J. Haematol.*, 2000, 109: 823-828).

Receptor tyrosine kinases, cytokine receptors, and some G protein-coupled receptors activate intracellular protein serine/threonine kinases known as mitogen-activated kinases (MAPKs). The activation of MAPKs requires a cascade-like mechanism in which each MAPK is phosphorylated by an upstream protein kinase, MAPK kinase (MAPKK), and the latter in turn is phosphorylated by a third protein kinase, MAPK kinase kinase (MAPKKK). The extracellular signal-regulated kinase (ERK) pathway (also referred to as the p44/42 mitogen-activated protein kinase (MAPK) pathway) is activated by a wide variety of mitogenic stimuli that interact with structurally distinct receptors and thus represents a convergence point for most, if not all, mitogenic signaling pathways (Seger R. et al., *FASEB J.*, 1995, 9: 726-735; Lewis T. S. et al., *Adv. Cancer Res.*, 1998, 74: 49-139; and Pearson G. et al., *Endocr. Rev.*, 2001, 22: 153-183). The present inventor has established that the activation of ERK1/2 (both ERK-1 and ERK-2 pathways) is required in RSV-induced early gene expression, providing a molecular link between ERK signaling and RSV infection. Any component of the ERK pathway is a potential therapeutic target for inhibition in accordance with the present invention. The mechanism of inhibition may be at the genetic level (e.g., interference with transcription or translation) or at the protein level (e.g., binding, competition). Because of their converging function, specific inhibition of MEK1/2 or ERK1/2 is expected to effectively intercept a wide variety of upstream mitogenic signals. Preferably, the inhibitor of ERK1 and/or ERK2 (ERK1/2) is a specific inhibitor, that either acts on MEK1/2 or ERK1/2 at the genetic level or protein level. Specific inhibition of the ERK pathway has been demonstrated using approaches such as expression of an ERK-specific antisense molecule (Pages G. et al., *Proc. Natl. Acad. Sci. USA*, 1993, 90: 8319-8323) and sequestration of ERK1/2 in the cytoplasm and therefore preventing ERK nuclear signaling (Brunet A. et al., *EMBO J*, 1999, 18: 664-674). Either or both approaches may be used in accordance with the present invention. For example, an inhibitor may be utilized that interferes with expression of ERK1 and/or ERK2, or which sequesters ERK 1 and/or ERK2 in the cytoplasm of the cell, preventing nuclear translocation.

As used herein, the term "ERK inhibitor" refers to agents capable of down-regulating or otherwise decreasing or suppressing the amount and/or activity of ERK-MAPK interactions. MAPK inhibitors may be used to down-regulate the quantity or activity of MAPK components (molecules). ERK inhibits down-regulate the quantity or activity of ERK components (molecules). Inhibition of these cellular components can be achieved by a variety of mechanisms known in the art, including, but not limited to, binding directly to ERK 1 or ERK2 (e.g., an ERK-inhibitor compound binding complex, or substrate mimetic), binding directly to MEK1 or MEK2, or inhibiting expression of the ERK or MEK genes. Examples of inhibitors of the ERK pathway that may be used in accordance with the invention include, but are not limited to, Raf-1 inhibitors, such as GW5074, BAY 43-9006, and ISIS 5132 (Lackey, K. et al., *Bioorg. Med. Chem. Lett.*, 2000, 10: 223-226; Lyons, J. F. et al., *Endocrine-related Cancer*, 2001, 8: 219-225; and Monia, B. P. et al., *Nat. Med.*, 1996, 2(6): 668-675, respectively); and MEK1/2 inhibitors, such as PD98059, PD184352, U0126 (Dudley D. T. et al., *Proc. Natl. Acad. Sci. USA*, 1995, 92: 7686-7689; Sepolt-Leopold J. S. et al., *Nat. Med.*, 1999, 5: 810-816; and Favata M. F. et al., *J. Biol. Chem.*, 273: 18623-18632, respectively). Both U0126 and PD98059 prevent phosphorylation of MEK1 by upstream kinases in a manner that appears to be substrate-directed (Davies, S. P. et al., *Biochem. J.*, 2000, 351: 95-105; Ahn N. G. et al., *Methods Enzymol.*, 2001, 332: 417-431). Based on recent evidence, it appears likely that PD98059, U0126, and PD184352 act as allosteric inhibitors, binding outside the ATP- and ERK1/2-binding sites on MEK1/2 and the modification of the three-dimensional structure of MEK1/2 renders it not phosphorylatable by upstream kinases (Davies, S. P. et al., 2001). Such a modification of MEK1/2 may also reduce their kinase activity towards ERK1/2; a high concentration of Uo126 and of PD184352 has been shown to inhibit MEK activity. A series of 3-cyano-4-(phenoxyanilo)quinolines with MEK inhibitory activity has also been developed by Wyeth-Ayerst (Zhang N. et al., *Bioorg Med. Chem. Lett.,* 2000, 10: 2825-2828). Several resorcylic acid lactones having inhibitor activity toward MEK have been isolated from microbial extracts. For example, Ro 09-2210, isolated from fungal broth FC2506, and L-783,277, purified from organic extracts of *Phoma* sp. (ATCC 74403), are competitive with ATP, and the MEK1 inhibition is reversible (Williams D. H. et al., *Biochemistry,* 1998, 37: 9579-9585; and Zhao A. et al., *J. Antibiot.,* 1999, 52: 1086-1094). Imidazolium trans-imidazoledimethyl sulfoxide-tetrachlororuthenate (NAMI-A) is a ruthenium-containing inhibitor of the phosphorylation of MEK, the upstream activator of ERK (Pintus G. et al., *Eur. J. Biochem.,* 2002, 269: 5861-5870).

A peptide corresponding to the amino-terminal 13 amino acids of MEK1 (MPKKKPTPIQLNP; SEQ ID NO:14), a region involved in the association of ERK1/2 with MEK1, has been shown to specifically inhibit the activation of ERK1/2 (Kelemen B. R. et al., *J. Biol. Chem.,* 2002, 277: 87841-8748). Purvalanol, one of the most potent cyclin-dependent kinase (CDK) inhibitors to date, has been shown to target ERK1 and ERK2 (Knockaert M. et al., *Oncogene,* 2002, 21: 6413-6424). Other ERK inhibitors that may be used in accordance with the present invention include those disclosed in U.S. patent publication 2003/0060469 (Ludwig S. et al.); U.S. patent publication 2004/0048861 (Bemis G. et al.); and U.S. patent publication 2004/0082631 (Hale M. et al.).

The terms "treatment", "treating" and the like are intended to mean obtaining a desired pharmacologic and/or physiologic effect, e.g., inhibition of respiratory syncytial virus (RSV) infection within a cell. The effect may be prophylactic in terms of completely or partially preventing the RSV infection or symptom thereof and/or may be therapeutic in terms of a partial or complete cure for RSV infection and/or adverse effect attributable to the infection. "Treatment" as used herein covers any treatment of a disease in a mammal, particularly a human, and includes: (a) preventing a disease or condition (e.g., preventing RSV infection) from occurring in an individual who may be predisposed to the disease but has not yet been diagnosed as having it; (b) inhibiting the disease, (e.g., arresting its development); or (c) relieving the disease (e.g., reducing symptoms associated with RSV infection).

The terms "administering", "administration", and "contacting" are intended to mean a mode of delivery including, without limitation, intranasal, oral, rectal, parenteral, subcutaneous, intravenous, intramuscular, intraperitoneal, intraarterial, transdermal or via a mucus membrane. The preferred route of administration for the STAT or ERK inhibitor is intranasal. Administration may be carried out locally, at a target site(s), or systemically. Preferably, the inhibitor is administered by a route such that an effective amount of the inhibitor is delivered to the respiratory tract of the subject. One skilled in the art recognizes that suitable forms of oral formulation include, but are not limited to, a tablet, a pill, a capsule, a lozenge, a powder, a sustained release tablet, a liquid, a liquid suspension, a gel, a syrup, a slurry, a suspension, and the like. For example, a daily dosage can be divided into one, two or more doses in a suitable form to be administered at one, two or more times throughout a time period.

As used herein, the term "co-administration" and variations thereof refers to the administration of two or more agents simultaneously (in one or more preparations), or consecutively. For example, one or more types of STAT or ERK inhibitors can be co-administered with other agents. Optionally, the method of the invention includes co-administration of a STAT or ERK inhibitor and an additional therapeutic agent such as an anti-viral agent or vaccine (e.g., an anti-RSV agent or gene expression vaccine).

The term "therapeutically effective" is intended to mean an amount of a STAT or ERK inhibitor sufficient to substantially improve some symptom associated with an RSV infection. For example, in the treatment of RSV infection, an agent that decreases, prevents, delays, suppresses, or arrests any symptom of the infection would be therapeutically effective. A therapeutically effective amount of the inhibitor is not required to cure the infection but will provide a treatment for the infection such that the onset of the infection is delayed, hindered, or prevented, or the associated symptoms are ameliorated, or the term of the infection is changed or, for example, is less severe or recovery is accelerated in subject.

When the STAT or ERK inhibitors are administered in combination therapies with other agents, they may be administered sequentially or concurrently to a subject. Alternatively, pharmaceutical compositions according to the present invention may comprise a combination of a STAT or ERK inhibitor, as described herein, a pharmaceutically acceptable carrier, and another therapeutic or prophylactic agent known in the art.

As used herein, the terms "individual", "patient", and "subject" are used interchangeably to refer to any vertebrate species, such as humans and animals, that are susceptible to respiratory syncytial virus (RSV) infection. Preferably, the patient is of a human or non-human mammalian species. Mammalian species that benefit from the disclosed methods include, and are not limited to, humans, apes, chimpanzees, orangutans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. Human or non-human animal subjects can range in age from neonates to elderly. Likewise, in vitro methods of the present invention can be carried out on cells of such mammalian species. Host cells comprising exogenous polynucleotides of the invention may be administered to the subject, and may, for example, be autogenic (use of one's own cells), allogenic (from one person to another), or transgenic or xenogenic (from one species to another), relative to the subject.

In accordance with another embodiment of the present invention, there is provided a method for treating or reducing the likelihood of developing an RSV infection by administering to a subject a pharmaceutically effective amount of a pharmaceutical composition of the present invention.

In one embodiment, the STAT or ERK inhibitor used in the methods and compositions of the invention is a polynucleotide that reduces expression of one or more of the subject's endogenous genes within the STAT or ERK pathways. Thus, the method involves administering an effective amount of polynucleotides that specifically target nucleotide sequence(s) within a target gene(s) of the STAT or ERK pathways. In one embodiment, the method of the invention involves reducing expression of one or more genes within the STAT or ERK pathways by administering a polynucleotide specific for the STAT or ERK pathway gene, wherein the polynucleotide interferes with expression of the gene in a sequence-specific manner, to yield reduced levels of the gene product (the translated polypeptide). Preferably, the polynucleotide is a silencing double stranded ribonucleic acid (RNA) sequence, also called a small interfering RNA (siRNA) that causes degradation of the targeted RNA. Thus, in one embodiment, the polynucleotide is a double stranded ribonucleic aid (dsRNA) that reduces expression of the STAT or ERK gene. In a specific embodiment, the targeted nucleotide sequence is at least a portion of the STAT or ERK genes, wherein a first strand of the dsRNA is substantially identical 19 to 49 consecutive nucleotides of the STAT or ERK gene, and a second strand of the dsRNA is substantially complementary to the first. In another embodiment, the polynucleotide is a double-stranded ribonucleic acid (dsRNA) comprising a first strand of nucleotides that is substantially identical to 19 to 25 consecutive nucleotides of the STAT or ERK gene, and a second strand that is substantially complementary to the first strand.

In another embodiment, the polynucleotide of the invention is a dsRNA comprising a first strand of nucleotides of at least 16 nucleotides sufficiently complementary to a target region of the STAT or ERK mRNA sequence to direct target-specific RNA interference (RNAi), and a second strand of nucleotides of at least 16 nucleotides substantially complementary to the first strand. In a further embodiment, the first strand is fully complementary to the target region of the mRNA sequence. In another embodiment, the dsRNA further comprises a loop formation comprising 4-11 nucleotides that connects the first and second strands. In a specific embodiment, the first and second strands each comprise 16, 17, 18, 19, 20, 21, 22, 23, 24, or 25 nucleotides. In another specific embodiment, the first and second strands each consist of 16, 17, 18, 19, 20, 21, 22, 23, 24, or 25 nucleotides.

In other embodiments, the polynucleotide of the invention is an antisense nucleic acid sequence (e.g., a single stranded oligonucleotide) that is complementary to a target region within the subject's STAT or ERK mRNA, which binds to the target region and inhibits translation. The antisense oligonucleotide may be DNA or RNA, or comprise synthetic analogs of ribo-deoxynucleotides. Thus, the antisense oligonucleotide inhibits expression of the STAT or ERK gene. In one embodiment, the antisense oligonucleotide consists of 8 nucleotides complementary to contiguous nucleotides within the RSV mRNA. In other embodiments, the oligonucleotide has a length of 9, 10, 11, 12, 13, 14, 15, or 16 nucleotides.

In other embodiments, the polynucleotide of the invention is an RNA molecule having enzymatic activity (a ribozyme) that inhibits expression of the target STAT or ERK gene(s). In one embodiment, the ribozyme comprises a 5'-end flanking region having 4-50 nucleotides and being complementary to a 3'-end target region within the STAT or ERK mRNA; a stem-loop region, comprising a stem portion having 2-12 nucleotide pairs and a loop portion comprising at least 2 unpaired nucleotides; and a 3'-end flanking region having 4-50 nucleotides and being complementary to a 5'end target site on the substrate RNA.

The nucleic acid target of the polynucleotides (e.g., siRNA, antisense oligonucleotides, and ribozymes) of the invention may be any location within the STAT or ERK gene or transcript.

Other aspects of the invention include vectors (e.g., viral vectors, expression cassettes, plasmids) comprising or encoding polynucleotides of the subject invention (e.g., siRNA, antisense nucleic acids, and ribozymes), and host cells genetically modified with polynucleotides or vectors of the subject invention. In one embodiment, the vector comprises a polynucleotide and expression control sequences that direct production of a transcript that hybridizes under physiological conditions to a target region within the subject's STAT or ERK mRNA.

The terms "reducing expression", "regulating expression", "reducing activity", or "regulating activity" generally refer to any process that functions to control or modulate the quantity or activity (functionality) of a cellular component. Static regulation maintains expression and/or activity at some given level. Up-regulation refers to a relative increase in expression and/or activity. In the present invention, regulation is preferably down-regulation of a cellular component. As used herein, down-regulation is synonymous with inhibition of a given cellular component.

As used herein, the term "polypeptide" refers to any polymer comprising any number of amino acids, and is interchangeable with "protein", "gene product", and "peptide".

As used herein, the term "nucleoside" refers to a molecule having a purine or pyrimidine base covalently linked to a ribose or deoxyribose sugar. Exemplary nucleosides include adenosine, guanosine, cytidine, uridine and thymidine. The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester linkage between 5' and 3' carbon atoms. The STAT or ERK inhibitors used in the methods and compositions of the present invention may include one or more nucleosides.

As used herein, the term "RNA" or "RNA molecule" or "ribonucleic acid molecule" refers generally to a polymer of ribonucleotides. The term "DNA" or "DNA molecule" or deoxyribonucleic acid molecule" refers generally to a polymer of deoxyribonucleotides. DNA and RNA molecules can be synthesized naturally (e.g., by DNA replication or transcription of DNA, respectively). RNA molecules can be post-transcriptionally modified. DNA and RNA molecules can also be chemically synthesized. DNA and RNA molecules can be single-stranded (i.e., ssRNA and ssDNA, respectively) or multi-stranded (e.g., double stranded, i.e., dsRNA and dsDNA, respectively). Based on the nature of the invention, however, the term "RNA" or "RNA molecule" or "ribonucleic acid molecule" can also refer to a polymer comprising primarily (i.e., greater than 80% or, preferably greater than 90%) ribonucleotides but optionally including at least one non-ribonucleotide molecule, for example, at least one deoxyribonucleotide and/or at least one nucleotide analog.

As used herein, the term "nucleotide analog", also referred to herein as an "altered nucleotide" or "modified nucleotide" refers to a non-standard nucleotide, including non-naturally occurring ribonucleotides or deoxyribonucleotides. Preferred nucleotide analogs are modified at any position so as to alter certain chemical properties of the nucleotide yet retain the ability of the nucleotide analog to perform its intended function. The STAT or ERK inhibitors used in the methods and compositions of the present invention may include one or more nucleotide analogs.

As used herein, the term "RNA analog" refers to a polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. As discussed above, the oligonucleotides may be linked with linkages which result in a lower rate of hydrolysis of the RNA analog as compared to an RNA molecule with phosphodiester linkages. Exemplary RNA analogues include sugar- and/or backbone-modified ribonucleotides and/or deoxyribonucleotides. Such alterations or modifications can further include addition of nonnucleotide material, such as to the end(s) of the RNA or internally (at one or more nucleotides of the RNA). An RNA analog need only be sufficiently similar to natural RNA that it has the ability to mediate (mediates) RNA interference or otherwise reduce target gene expression. The STAT or ERK inhibitors used in the methods and compositions of the present invention may include one or more RNA analogs.

As used herein, the terms "operably-linked" and "operatively-linked" are used interchangeably to refer to an arrangement of flanking sequences wherein the flanking sequences so described are configured or assembled so as to perform their usual function. Thus, a flanking sequence operably-linked to a coding sequence may be capable of effecting the replication, transcription and/or translation of the coding sequence. For example, a coding sequence is operably-linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence, and the promoter sequence can still be considered "operably-linked" to the coding sequence. Each nucleotide sequence coding for a siRNA will typically have its own operably-linked promoter sequence.

The term "vector" is used to refer to any molecule (e.g., nucleic acid, plasmid, or virus) used to transfer coding information (e.g., a polynucleotide of the invention) to a host cell. The term "expression vector" refers to a vector that is suitable for use in a host cell (e.g., a subject's cell) and contains nucleic acid sequences which direct and/or control the expression of exogenous nucleic acid sequences. Expression includes, but is not limited to, processes such as transcription, translation, and RNA splicing, if introns are present. The vectors of the present invention can be conjugated with chitosan or chitosan derivatives. Such chitosan conjugates can be administered to subjects or host cells according to the methods of the present invention. For example, polynucleotide chitosan nanoparticles (e.g., nanospheres) can be generated, as described by Roy, K. et al. (*Nat Med*, 1999, 5: 387). Chitosan allows increased bioavailability of the nucleic acid sequences because of protection from degradation by serum nucleases in the matrix and thus has great potential as a mucosal gene delivery system. Chitosan also has many beneficial effects, including anticoagulant activity, wound-healing properties, and immunostimulatory activity, and is capable of modulating immunity of the mucosa and bronchus-associated lymphoid tissue. In one embodiment of the present invention, the polynucleotides of the subject invention are conjugated with chitosan-derived nanoparticles.

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of target genes.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference.

As used herein, a siRNA having a "sequence sufficiently complementary to a target mRNA sequence to direct target-specific RNA interference (RNAi)" means that the siRNA has a sequence sufficient to trigger the destruction of the target mRNA by the RNAi machinery or process. STAT or ERK "mRNA", "messenger RNA", and "transcript" each refer to single-stranded RNA that specifies the amino acid sequence of one or more STAT or ERK polypeptides. This information is translated during protein synthesis when ribosomes bind to the mRNA.

As used herein, the term "cleavage site" refers to the residues, e.g., nucleotides, at which RISC* cleaves the target RNA, e.g., near the center of the complementary portion of the target RNA, e.g., about 8-12 nucleotides from the 5' end of the complementary portion of the target RNA.

As used herein, the term "mismatch" refers to a basepair consisting of non-complementary bases, e.g., not normal complementary G:C, A:T or A:U base pairs.

As used herein, the term "isolated" molecule (e.g., isolated nucleic acid molecule) refers to molecules which are substantially free of other cellular material, or culture medium when produced by recombinant techniques, or substantially free of chemical precursors or other chemicals when chemically synthesized.

As used herein, the term "in vitro" has its art recognized meaning, e.g., involving purified reagents or extracts, e.g., cell extracts. The term "in vivo" also has its art recognized meaning, e.g., involving living cells in an organism, e.g., immortalized cells, primary cells, and/or cell lines in an organism.

The methods of the invention may include further steps. In some embodiments, a subject with the relevant condition or disease (e.g., RSV infection, disorders associated with RSV infection, or disorders associated with impaired interferon production) is identified, or a subject at risk for the condition or disease is identified. A subject may be someone who has not been diagnosed with the disease or condition (diagnosis, prognosis, and/or staging) or someone diagnosed with disease or condition (diagnosis, prognosis, monitoring, and/or staging), including someone treated for the disease or condition (prognosis, staging, and/or monitoring). Alternatively, the subject may not have been diagnosed with the disease or condition but suspected of having the disease or condition based either on patient history or family history, or the exhibition or observation of characteristic symptoms.

As used herein, an "effective amount" of polynucleotide that selectively interferes with expression of the STAT or ERK gene(s) (e.g., an siRNA, an antisense nucleotide sequence or strand, and/or a ribozyme) is that amount effective to reduce expression of the target STAT or ERK gene(s) and bring about the physiological changes desired in the cells to which the polynucleotide is administered in vitro (e.g., ex vivo) or in vivo. The term "therapeutically effective amount" as used herein with respect to polynucleotides that interfere with expression of the STAT or ERK gene(s), means that amount of polynucleotide (e.g., an siRNA, an antisense oligonucleotide, and/or a ribozyme), alone or in combination with another agent according to the particular aspect of the invention, that elicits the biological or medicinal response in cells (e.g., tissue(s)) that is being sought by a researcher, veterinarian, medical doctor or other clinician, which includes alleviation and/or prevention of the symptoms of the disease or disorder being treated. For example, a polynucleotide can be administered to a subject in combination with other agents effective for alleviating or preventing the symptoms of RSV infection, such as the gene expression vaccines disclosed in international publication WO 03/028759A1, which is incorporated by reference herein in its entirety. The term "therapeutically effective amount" as used herein with respect to polynucleotides that encode a polypeptide that is an inhibitor of STAT or ERK signaling, means that amount of, alone or in combination with another agent according to the particular aspect of the invention, that elicits the biological or medicinal response in cells (e.g., tissue(s)) that is being sought by a researcher, veterinarian, medical doctor or other clinician, which includes alleviation and/or prevention of the symptoms of the disease or disorder being treated.

Various methods of the present invention can include a step that involves comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing a STAT or ERK inhibitor into a cell or subject. In another embodiment, a "suitable control" or "appropriate control" is a value, level, feature, characteristic, property, etc. determined in a cell or subject, e.g., a control or normal cell or organism, exhibiting, for example, normal traits. In yet another embodiment, a "suitable control" or "appropriate control" is a predefined value, level, feature, characteristic, property, etc.

In a preferred embodiment, the STAT or ERK inhibitor used in the methods and compositions of the invention includes one or more targeting moieties. As used herein, the term "targeting moiety" is intended to mean a functional group that serves to target or direct the inhibitor to a particular location or association (e.g., a specific binding event). Thus, for example, a targeting moiety may be used to target a molecule to a specific target protein or enzyme, or to a particular cellular location, or to a particular cell type, to selectively enhance accumulation of the contrast agent. Suitable targeting moieties include, but are not limited to, polypeptides, nucleic acids, carbohydrates, lipids, hormones including proteinaceous and steroid hormones, growth factors, receptor ligands, antigens and antibodies, and the like.

A targeting moiety may include components useful in targeting the STAT or ERK inhibitor to a particular subcellular location. As will be appreciated by those in the art, the localization of proteins within a cell is a simple method for increasing effective concentration. For example, shuttling a drug into the nucleus confines them to a smaller space thereby increasing concentration. The physiological target may simply be localized to a specific compartment, and the inhibitor must be localized appropriately. More than one targeting moiety can be conjugated or otherwise associated with each STAT or ERK inhibitor, and the target molecule for each targeting moiety can be the same or different.

Thus, suitable targeting sequences include, but are not limited to, binding sequences capable of causing binding of the moiety to a predetermined molecule or class of molecules, while retaining bioactivity of the inhibitor; sequences signaling selective degradation, of itself or co-bound proteins; and signal sequences capable of constitutively localizing the inhibitor to a predetermined cellular locale, including (a) subcellular locations such as the Golgi, endoplasmic reticulum, nucleus, nucleoli, nuclear membrane, mitochondria, chloroplast, secretory vesicles, lysosome, and cellular membrane; and (b) extracellular locations via a secretory signal. Particularly preferred is localization to either subcellular location.

The targeting moiety can function to target or direct the STAT or ERK inhibitor to a particular location, cell type, diseased tissue, or association. In general, the targeting moiety is directed against a target molecule. As will be appreciated by those in the art, the STAT or ERK inhibitors are preferably administered to the respiratory epithelium; thus, preferred targeting moieties are those that allow concentration of the agents in a particular localization. Thus, for example, antibodies, cell surface receptor ligands and hormones, lipids, sugars and dextrans, alcohols, bile acids, fatty acids, amino acids, peptides and nucleic acids may all be attached to localize or target the STAT or ERK inhibitor to a particular site.

In some embodiments, the targeting moiety is a polypeptide. In other embodiments, the targeting moiety is an antibody. In one embodiment, antibodies against virus or bacteria can be used as targeting moieties. As will be appreciated by those in the art, antibodies to any number of viruses may be used. Preferably, the antibody is directed against respiratory syncytial virus.

In a preferred embodiment, the targeting moiety is all or a portion (e.g., a binding portion) of a ligand for a cell surface receptor. In another embodiment, the targeting moiety is a carbohydrate. As used herein, the term "carbohydrate" includes compounds with the general formula $Cx(H_2O)_y$. Monosaccharides, disaccharides, and oligo- or polysaccharides are all included within the definition and comprise polymers of various sugar molecules linked via glycosidic linkages. In another embodiment, the targeting moiety is a lipid. As used herein, the term "lipid" includes fats, fatty oils, waxes, phospholipids, glycolipids, terpenes, fatty acids, and glycerides, particularly the triglycerides. Also included within the definition of lipids are the eicosanoids, steroids and sterols, some of which are also hormones, such as prostaglandins, opiates, and cholesterol.

In a preferred embodiment, the targeting moiety may be used to either allow the internalization of the STAT or ERK inhibitor to the cell cytoplasm or localize it to a particular cellular compartment, such as the nucleus. In a preferred embodiment, the targeting moiety is all or a portion of the HIV-1 Tat protein, and analogs and related proteins, which allows very high uptake into target cells (See for example, Fawell et al., *PNAS USA* 91: 664 (1994); Frankel et al., *Cell* 55: 1189 (1988); Savion et al., *J. Biol. Chem.* 256: 1149 (1981); Derossi et al., *J. Biol. Chem.* 269: 10444 (1994); and Baldin et al., *EMBO J.* 9: 1511 (1990), all of which are incorporated by reference.

In a preferred embodiment, the targeting moiety is a nuclear localization signal (NLS). NLSs are generally short, positively charged (basic) domains that serve to direct the moiety to which they are attached to the cell's nucleus. Numerous NLS amino acid sequences have been reported including single basic NLS's such as that of the SV40 (monkey virus) large T Antigen (Pro Lys Lys Lys Arg Lys Val; SEQ ID NO:15), Kalderon (1984), et al., *Cell,* 39: 499-509; the human retinoic acid receptor-beta nuclear localization signal (ARRRRP; SEQ ID NO:16); NFκB p50 (EEVQRKRQKL, SEQ ID NO:17; Ghosh et al., *Cell* 62: 1019 (1990)); NFκB p65 (EEKRKRTYE, SEQ ID NO:18; Nolan et al., *Cell* 64: 961 (1991)); and others (see for example Boulikas, *J. Cell. Biochem.* 55(1): 32-58 (1994), hereby incorporated by reference) and double basic NLSs exemplified by that of the *Xenopus* (African clawed toad) protein, nucleoplasmin (Ala Val Lys Arg Pro Ala Ala Thr Lys Lys Ala Gly Gln Ala Lys Lys Lys Lys Leu Asp; SEQ ID NO:19), Dingwall, et al., Cell, 30: 449-458, 1982 and Dingwall, et al., *J. Cell Biol.,* 107: 641-849; 1988). Numerous localization studies have demonstrated that NLSs incorporated in synthetic peptides or grafted onto reporter proteins not normally targeted to the cell nucleus cause these peptides and reporter proteins to be concentrated in the nucleus (see, for example, Dingwall, and Laskey, *Ann, Rev. Cell Biol.*, 2: 367-390, 1986; Bonnerot, et al., *Proc. Natl. Acad. Sci. USA*, 84: 6795-6799, 1987; Galileo, et al., *Proc. Natl. Acad. Sci. USA*, 87: 458-462, 1990).

In specific embodiments, a cell-binding agent is utilized as the targeting moiety. Selection of the appropriate cell-binding agent is a matter of choice that depends upon the particular cell population to be targeted, but in general monoclonal antibodies are preferred if an appropriate one is available.

Small Molecules

As used herein, the term "small molecules" encompasses molecules other than proteins or nucleic acids without strict regard to size. When STAT or ERK inhibitors are "small molecules" (or "small molecule STAT or ERK inhibitors") are referred to, what is meant is non-protein, non-nucleic acid inhibitors of STAT or ERK signaling. In many cases, such inhibitors are smaller than STAT or ERK inhibitors that are polypeptides or nucleic acids. Examples of small molecules that may be administered to screened according to the methods of the invention include small organic molecules, peptide-like molecules, peptidomimetics, carbohydrates, lipids or other organic (carbon containing) or inorganic molecules. Examples of small molecule ERK inhibitors include GW5074, BAY 43-9006, PD98059, PD184352, U0126, 3-cyano-4-(phenoxyanilno)quinolines (such as Wyeth-Ayerst Compound 14), resorcylic acid lactones (such as Ro 09-2210 and L-783,277), and purvalanol (Kohno M. et al., *Progress in Cell Cycle Research*, 2003, 5: 219-224).

Polypeptides

The STAT or ERK inhibitor used in the methods and compositions of the present invention can also be a polypeptide exhibiting STAT or ERK inhibitory activity, such as a receptor decoy. A peptide corresponding to the amino-terminal 13 amino acids of MEK1 (MPKKKPTPIQLNP; SEQ ID NO:14), a region involved in the association of ERK1/2 with MEK1, has been shown to specifically inhibit the activation of ERK1/2 (Kelemen B. R. et al., *J. Biol. Chem.*, 2002, 277: 87841-8748). Various means for delivering polypeptides to a cell can be utilized to carry out the methods of the subject invention. For example, protein transduction domains (PTDs) can be fused to the polypeptide, producing a fusion polypeptide, in which the PTDs are capable of transducing the polypeptide cargo across the plasma membrane (Wadia, J. S. and Dowdy, S. F., *Curr. Opin. Biotechnol.*, 2002, 13(1)52-56). Examples of PTDs include the *Drosophila* homeotic transcription protein antennapedia (Antp), the herpes simples virus structural protein VP22, and the human immuno-deficiency virus 1 (HIV-1) transcriptional activator Tat protein.

According to the methods of the subject invention, recombinant cells can be administered to a patient, wherein the recombinant cells have been genetically modified to express a nucleotide sequence encoding a STAT or ERK inhibitory polypeptide. If the cells to be genetically modified already express a nucleotide sequence encoding a STAT or ERK inhibitor polypeptide, the genetic modification can serve to enhance or increase expression of the nucleotide sequence beyond the normal or constitutive amount (e.g., "overexpression").

Antibodies

The STAT or ERK inhibitors used in accordance within this invention can be also be an antibody that is specifically reactive with a STAT or ERK protein, thereby inhibiting STAT or ERK signaling. As used herein, the term "antibody" refers to a protein comprising at least one, and preferably two, heavy (H) chain variable regions As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. Sequences of Proteins of Immunological Interest, Fifth Edition, U.S. Department of Health and Human Services, NIH Publication No. 91-3242, 1991; and Chothia, C. et al. *J. Mol. Biol.* 196: 901-917, 1987).

The antibody can further include a heavy and light chain constant region, to thereby form a heavy and light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

The term "antibody" includes antibody fragments (an antigen binding portion of an antibody), as are known in the art, including Fab or $Fab_2$, single chain antibodies (Fv for example), chimeric antibodies, etc., either produced by the modification of whole antibodies or those synthesized de novo using recombinant DNA technologies.

The term "antigen-binding fragment" of an antibody (or simply "antibody portion," or "fragment"), as used herein, refers to one or more fragments of a full-length antibody that retain the ability to specifically bind to an antigen. Examples of binding fragments encompassed within the term "antigen-binding fragment" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., *Nature* 341: 544-546, 1989), which consists of a VH domain; and (vi) an isolated complementarity determining region (CDR). Furthermore, although the two domains of the Fv fragment, VL and VH, are coded for by separate nucleic acids, they can be joined, using recombinant methods, by a synthetic linker that enables them to be made as a single protein chain in which the VL and VH regions pair to form monovalent molecules (known as single chain Fv (scFv); see e.g., Bird et al., *Science* 242: 423-426, 1988; and Huston et al., *Proc. Natl. Acad. Sci. USA* 85: 5879-5883, 1988). Such single chain antibodies are also intended to be encompassed within the term "antigen-binding fragment" or "fragment" of an antibody. These antibody fragments are obtained using conventional techniques known to those with skill in the art, and the fragments are screened for utility in the same manner as are intact antibodies. The term "monoclonal antibody" or "monoclonal antibody composition", as used herein, refers to a population of antibody molecules that contain only one species of an antigen binding site capable of immunoreacting with a particular epitope. A monoclonal antibody composition thus typically displays a single binding affinity for a particular protein with which it immunoreacts.

Anti-protein/anti-peptide antisera or monoclonal antibodies can be made as described herein by using standard protocols (See, for example, Antibodies: A Laboratory Manual ed. by Harlow and Lane (Cold Spring Harbor Press: 1988)).

A STAT or ERK protein, or a portion or fragment thereof, can be used as an immunogen to generate antibodies that bind the component using standard techniques for polyclonal and monoclonal antibody preparation. The full-length component protein can be used or, alternatively, antigenic peptide fragments of the component can be used as immunogens.

Typically, a peptide is used to prepare antibodies by immunizing a suitable subject, (e.g., rabbit, goat, mouse or other mammal) with the immunogen. An appropriate immunogenic preparation can contain, for example, a recombinant STAT or ERK protein or a chemically synthesized protein. The preparation can further include an adjuvant, such as Freund's complete or incomplete adjuvant, or similar immunostimulatory agent. Immunization of a suitable subject with an immunogenic component or fragment preparation induces a polyclonal antibody response.

Additionally, antibodies produced by genetic engineering methods, such as chimeric and humanized monoclonal antibodies, comprising both human and non-human portions, which can be made using standard recombinant DNA techniques, can be used. Such chimeric and humanized monoclonal antibodies can be produced by genetic engineering using standard DNA techniques known in the art, for example using methods described in U.S. Pat. No. 4,816,567; Better et al., *Science* 240: 1041-1043, 1988; Liu et al., *PNAS* 84: 3439-3443, 1987; Liu et al., *J. Immunol.* 139: 3521-3526, 1987; Sun et al. *PNAS* 84: 214-218, 1987; Nishimura et al., *Canc. Res.* 47: 999-1005, 1987; Wood et al., *Nature* 314: 446-449, 1985; and Shaw et al., *J. Natl. Cancer Inst.* 80: 1553-1559, 1988); Morrison, S. L., *Science* 229: 1202-1207, 1985; Oi et al., *BioTechniques* 4: 214, 1986; U.S. Pat. No. 5,225,539; Jones et al., *Nature* 321: 552-525, 1986; Verhoeyan et al., *Science* 239: 1534, 1988; and Beidler et al., *J. Immunol.* 141: 4053-4060, 1988.

In addition, a human monoclonal antibody directed against STAT or ERK proteins can be made using standard techniques. For example, human monoclonal antibodies can be generated in transgenic mice or in immune deficient mice engrafted with antibody-producing human cells. Methods of generating such mice are described, for example, in Wood et al. PCT publication WO 91/00906, Kucherlapati et al. PCT publication WO 91/10741; Lonberg et al. PCT publication WO 92/03918; Kay et al. PCT publication WO 92/03917; Kay et al. PCT publication WO 93/12227; Kay et al. PCT publication 94/25585; Rajewsky et al. PCT publication WO 94/04667; Ditullio et al. PCT publication WO 95/17085; Lonberg, N. et al. *Nature* 368: 856-859, 1994; Green, L. L. et al. *Nature Genet.* 7: 13-21, 1994; Morrison, S. L. et al. *Proc. Natl. Acad. Sci. USA* 81: 6851-6855, 1994; Bruggeman et al. *Year Immunol.* 7: 33-40, 1993; Choi et al. *Nature Genet.* 4: 117-123, 1993; Tuaillon et al. *PNAS* 90: 3720-3724, 1993; Bruggeman et al. (1991) *Eur. J. Immunol.* 21: 1323-1326, 1991; Duchosal et al. PCT publication WO 93/05796; U.S. Pat. No. 5,411,749; McCune et al. *Science* 241: 1632-1639, 1988, Kamel-Reid et al. *Science* 242: 1706, 1988; Spanopoulou *Genes & Development* 8: 1030-1042, 1994; Shinkai et al. *Cell* 68: 855-868, 1992. A human antibody-transgenic mouse or an immune deficient mouse engrafted with human antibody-producing cells or tissue can be immunized with STAT or ERK proteins or an antigenic peptide thereof, and splenocytes from these immunized mice can then be used to create hybridomas. Methods of hybridoma production are well known.

Human monoclonal antibodies can also be prepared by constructing a combinatorial immunoglobulin library, such as a Fab phage display library or a scFv phage display library, using immunoglobulin light chain and heavy chain cDNAs prepared from mRNA derived from lymphocytes of a subject (see, e.g., McCafferty et al. PCT publication WO 92/01047; Marks et al. *J. Mol. Biol.* 222: 581-597, 1991; and Griffiths et al. *EMBO J.* 12: 725-734, 1993). In addition, a combinatorial library of antibody variable regions can be generated by mutating a known human antibody. For example, a variable region of a human antibody known to bind a STAT or ERK protein can be mutated by, for example, using randomly altered mutagenized oligonucleotides, to generate a library of mutated variable regions which can then be screened to bind to STAT or ERK proteins. Methods of inducing random mutagenesis within the CDR regions of immunoglobin heavy and/or light chains, methods of crossing randomized heavy and light chains to form pairings and screening methods can be found in, for example, Barbas et al. PCT publication WO 96/07754; Barbas et al. *Proc. Nat'l Acad. Sci. USA* 89: 4457-4461, 1992.

RNA Interference

RNAi is an efficient process whereby double-stranded RNA (dsRNA, also referred to herein as siRNAs or ds siR-NAs, for double-stranded small interfering RNAs) induces the sequence-specific degradation of targeted mRNA in animal and plant cells (Hutvagner and Zamore, *Curr. Opin. Genet. Dev.*, 12: 225-232 (2002); Sharp, *Genes Dev.*, 15: 485-490 (2001)). In mammalian cells, RNAi can be triggered by 21-nucleotide (nt) duplexes of small interfering RNA (siRNA) (Chiu et al., *Mol. Cell.*, 10: 549-561 (2002); Elbashir et al., *Nature* 411: 494-498 (2001)), or by micro-RNAs (mRNA), functional small-hairpin RNA (shRNA), or other dsRNAs which can be expressed in vivo using DNA templates with RNA polymerase III promoters (Zeng et al., *Mol. Cell* 9: 1327-1333 (2002); Paddison et al., *Genes Dev.* 16: 948-958 (2002); Lee et al., *Nature Biotechnol.* 20: 500-505 (2002); Paul et al., *Nature Biotechnol.* 20: 505-508 (2002); Tuschl, T., *Nature Biotechnol.* 20: 440-448 (2002); Yu et al., *Proc. Natl. Acad. Sci. USA* 99(9): 6047-6052 (2002); McManus et al., *RNA* 8: 842-850 (2002); Sui et al., *Proc. Natl. Acad. Sci. USA* 99(6): 5515-5520 (2002)). Accordingly, the method of the invention involves administering such molecules that are targeted to STAT or ERK mRNAs within the subject or host cells.

siRNA Molecules

The nucleic acid molecules or constructs of the invention include dsRNA molecules comprising 16-30 nucleotides, e.g., 16, 17, 18, 19, 20, 21, 22, 23, 24, 25, 26, 27, 28, 29, or 30 nucleotides, in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA of the subject or host cell's STAT or ERK mRNA, and the other strand is identical or substantially identical to the first strand. The dsRNA molecules of the invention can be chemically synthesized, or can be transcribed in vitro from a DNA template, or in vivo from, e.g., shRNA. The dsRNA molecules can be designed using any method known in the art, for instance, by using the following protocol:

1. Beginning with the AUG start codon, look for AA dinucleotide sequences; each AA and the 3' adjacent 16 or more nucleotides are potential siRNA targets. Further, siR-NAs with lower G/C content (35-55%) may be more active than those with G/C content higher than 55%. Thus, in one embodiment, the invention includes polynucleotides having 35-55% G/C content. In addition, the strands of the siRNA can be paired in such a way as to have a 3' overhang of 1 to 4, e.g., 2, nucleotides. Thus, in another embodiment, the polynucleotides can have a 3' overhang of 2 nucleotides. The overhanging nucleotides can be either RNA or DNA.

2. Using any method known in the art, compare the potential targets to the appropriate genome database (human, mouse, rat, etc.) and eliminate from consideration any target sequences with significant homology to other coding sequences for which reduced expression is not desired. One such method for such sequence homology searches is known as BLAST, which is available at the National Center for Biotechnology Information web site of the National Institutes of Health.

3. Select one or more sequences that meet the particular criteria for evaluation. Further general information regarding the design and use of siRNA can be found in "The siRNA User Guide," available at the web site of the laboratory of Dr. Thomas Tuschl at Rockefeller University.

4. Negative control siRNAs preferably have the same nucleotide composition as the selected siRNA, but without significant sequence complementarity to the appropriate genome. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

The polynucleotides of the invention can include both unmodified siRNAs and modified siRNAs as known in the art. Thus, the invention includes siRNA derivatives that include siRNA having two complementary strands of nucleic acid, such that the two strands are crosslinked. For example, a 3' OH terminus of one of the strands can be modified, or the two strands can be crosslinked and modified at the 3' OH terminus. The siRNA derivative can contain a single crosslink (e.g., a psoralen crosslink). In some embodiments, the siRNA derivative has at its 3' terminus a biotin molecule (e.g., a photocleavable biotin), a peptide (e.g., a Tat peptide), a nanoparticle, a peptidomimetic, organic compounds (e.g., a dye such as a fluorescent dye), or dendrimer. Modifying siRNA derivatives in this way can improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

The nucleic acid compositions of the invention can be unconjugated or can be conjugated to another moiety, such as a nanoparticle, to enhance a property of the compositions, e.g., a pharmacokinetic parameter such as absorption, efficacy, bioavailability, and/or half-life. The conjugation can be accomplished by methods known in the art, e.g., using the methods of Lambert et al., *Drug Deliv. Rev.* 47(1): 99-112 (2001) (describes nucleic acids loaded to polyalkylcyanoacrylate (PACA) nanoparticles); Fattal et al., *J. Control Release* 53(1-3): 137-43 (1998) (describes nucleic acids bound to nanoparticles); Schwab et al., *Ann. Oncol.* 5 Suppl. 4: 55-8 (1994) (describes nucleic acids linked to intercalating agents, hydrophobic groups, polycations or PACA nanoparticles); and Godard et al., *Eur. J. Biochem.* 232(2): 404-10 (1995) (describes nucleic acids linked to nanoparticles).

The nucleic acid molecules of the present invention can also be labeled using any method known in the art; for instance, the nucleic acid compositions can be labeled with a fluorophore, e.g., Cy3, fluorescein, or rhodamine. The labeling can be carried out using a kit, e.g., the SILENCER siRNA labeling kit (AMBION). Additionally, the siRNA can be radiolabeled, e.g., using $^{3}H$, $^{32}P$, or other appropriate isotope.

In accordance with the invention, siRNAs can be fused to other nucleotide molecules, or to polypeptides, in order to direct their delivery or to accomplish other functions. Thus, for example, fusion proteins comprising a siRNA oligonucleotide that is capable of specifically interfering with expression of one or more STAT or ERK genes may comprise affinity tag polypeptide sequences, which refers to polypeptides or peptides that facilitate detection and isolation of the polypeptide via a specific affinity interaction with a ligand. The ligand may be any molecule, receptor, counter-receptor, antibody or the like with which the affinity tag may interact through a specific binding interaction as provided herein. Such peptides include, for example, poly-His or "FLAG" or the like, e.g., the antigenic identification peptides described in U.S. Pat. No. 5,011,912 and in Hopp et al., (*Bio/Technology* 6: 1204, 1988), or the XPRESS epitope tag (INVITROGEN, Carlsbad, Calif.). The affinity sequence may be a hexa-histidine tag as supplied, for example, by a pBAD/His (INVITROGEN) or a pQE-9 vector to provide for purification of the mature polypeptide fused to the marker in the case of a bacterial host, or, for example, the affinity sequence may be a hemagglutinin (HA) tag when a mammalian host, e.g., COS-7 cells, is used. The HA tag corresponds to an antibody defined epitope derived from the influenza hemagglutinin protein (Wilson et al., 1984 *Cell* 37: 767).

Furthermore, because RNAi is believed to progress via at least one single-stranded RNA intermediate, the skilled artisan will appreciate that ss-siRNAs (e.g., the antisense strand of a ds-siRNA) can also be designed as described herein and utilized according to the claimed methodologies.

siRNA Delivery for Longer-Term Expression

Synthetic siRNAs can be delivered into cells in vitro or in vivo by methods known in the art, including cationic liposome transfection and electroporation. However, these exogenous siRNA generally show short-term persistence of the silencing effect (4 to 5 days in cultured cells), which may be beneficial in certain embodiments. To obtain longer term suppression of STAT or ERK gene expression and to facilitate delivery under certain circumstances, one or more siRNA duplexes, e.g., STAT or ERK ds siRNA, can be expressed within cells from recombinant DNA constructs. Such systems for expressing siRNA duplexes within cells from recombinant DNA constructs to allow longer-term target gene suppression in cells are known in the art, including mammalian Pol III promoter systems (e.g., H1 or U6/snRNA promoter systems (Tuschl (2002), supra) capable of expressing functional double-stranded siRNAs; (Bagella et al., *J. Cell. Physiol.* 177: 206-213 (1998); Lee et al. (2002), supra; Miyagishi et al. (2002), supra; Paul et al. (2002), supra; Yu et al. (2002), supra; Sui et al. (2002), supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by an H1 or U6 snRNA promoter can be expressed in cells, and can inhibit target gene expression (Bagella et al. (1998), supra; Lee et al. (2002), supra; Miyagishi et al. (2002), supra; Paul et al. (2002), supra; Yu et al. (2002), supra; Sui et al. (2002) supra). Constructs containing siRNA sequence(s) under the control of a T7 promoter also make functional siRNAs when co-transfected into the cells with a vector expressing T7 RNA polymerase (Jacque (2002), supra). A single construct may contain multiple sequences coding for siRNAs, such as multiple regions of the STAT and/or ERK mRNA, and can be driven, for example, by separate PolIII promoter sites.

Animal cells express a range of non-coding RNAs of approximately 22 nucleotides termed micro RNA (mRNAs) that can regulate gene expression at the post transcriptional or translational level during animal development. One common feature of mRNAs is that they are all excised from an approximately 70 nucleotide precursor RNA stem-loop, probably by Dicer, an RNase III-type enzyme, or a homolog thereof. By substituting the stem sequences of the mRNA precursor with mRNA sequence complementary to the target mRNA, a vector construct that expresses the novel mRNA can be used to produce siRNAs to initiate RNAi against specific mRNA targets in mammalian cells (Zeng (2002), supra). When expressed by DNA vectors containing polymerase III promoters, micro-RNA designed hairpins can silence gene expression (McManus (2002), supra). Viral-mediated delivery mechanisms can also be used to induce specific silencing of targeted genes through expression of siRNA, for example, by generating recombinant adenoviruses harboring siRNA under RNA Pol II promoter transcription control (Xia et al. (2002), supra). Infection of HeLa cells by these recombinant adenoviruses allows for diminished endogenous target gene expression. Injection of the recombinant adenovirus vectors into transgenic mice expressing the target genes of the siRNA results in in vivo reduction of target gene expression. In an animal model, whole-embryo electroporation can efficiently deliver synthetic siRNA into post-implantation mouse embryos (Calegari et al., *Proc. Natl. Acad. Sci. USA* 99(22): 14236-40 (2002)). In adult mice, efficient delivery of siRNA can be accomplished by the "high-pressure" delivery technique, a rapid injection (within 5 seconds) of a large volume of siRNA-containing solution into animal via the tail vein (Liu (1999), supra; McCaffrey (2002), supra; Lewis, *Nature Genetics* 32: 107-108 (2002)). Nanoparticles and liposomes can also be used to deliver siRNA into animals.

Uses of Engineered RNA Precursors to Induce RNAi

Engineered RNA precursors, introduced into host cells or whole organisms (subjects) as described herein, will lead to the production of a desired siRNA molecule. Such an siRNA molecule will then associate with endogenous protein components of the RNAi pathway to bind to and target a specific STAT or ERK mRNA sequence for cleavage and destruction. In this fashion, the mRNA to be targeted by the siRNA generated from the engineered RNA precursor will be depleted from the cell or organism, leading to a decrease in the concentration of the STAT or ERK protein encoded by that mRNA in the cell or organism. The RNA precursors are typically nucleic acid molecules that individually encode either one strand of a dsRNA or encode the entire nucleotide sequence of an RNA hairpin loop structure.

Antisense

The STAT or ERK inhibitor used in the methods and compositions of the invention can be an antisense nucleic acid molecule. An "antisense" nucleic acid molecule (antisense oligonucleotide) can include a nucleotide sequence that is complementary to a "sense" nucleic acid sequence encoding a STAT or ERK protein, e.g., complementary to the coding strand of a double-stranded cDNA molecule or complementary to at least a portion of a STAT or ERK gene. The antisense nucleic acid sequence can be complementary to an entire coding strand of a target sequence, or to only a portion thereof (for example, STAT or ERK genes, or a portion of either or both). In another embodiment, the antisense nucleic acid molecule is antisense to a "noncoding region" of the coding strand of a nucleotide sequence within the STAT or ERK gene. An antisense oligonucleotide can be, for example, about 7, 10, 15, 20, 25, 30, 35, 40, 45, 50, 55, 60, 65, 70, 75, 80, or more nucleotides in length. An example of an antisense oligonucleotide with inhibitory activity toward ERK signaling is ISIS 5132, a 20-base phosphorothioate antisense oligodoxynucleotide designed to hybridize to the 3' untranslated region of the c-raf-1 mRNA (Monia, B. P. et al., *Nat. Med.,* 1996, 2(6): 668-675; Stevenson J. P. et al., *J. Clin. Oncol.,* 1999, 17: 2227-2236; O'Dwyer P. J. et al., *Clin. Cancer Res.,* 1999, 5: 3977-3982).

An antisense nucleic acid molecule can be designed such that it is complementary to the entire STAT or ERK gene, but can also be an oligonucleotide that is antisense to only a portion of the STAT or ERK gene. For example, the antisense oligonucleotide can be complementary to the region surrounding the translation start site of the target mRNA, e.g., between the −10 and +10 regions of the target gene nucleotide sequence of interest. An antisense oligonucleotide sequence can be, for example, about 7, 10, 15, 20, 25, 30, 35, 40, 45, 50, 55, 60, 65, 70, 75, 80, or more nucleotides in length.

An antisense nucleic acid molecule of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid sequence also can be produced biologically using an expression vector into which a nucleic acid sequence has been subcloned in an antisense orientation (i.e., RNA transcribed from the inserted nucleic acid sequence will be of an antisense orientation to a target nucleic acid sequence of interest, described further in the following subsection).

The antisense nucleic acid molecules of the invention are typically administered to a subject (e.g., systemically or locally by direct injection at a tissue site), or generated in situ such that they hybridize with or bind to STAT or ERK mRNA to thereby inhibit expression of the STAT or ERK protein. Alternatively, antisense nucleic acid molecules can be modified to target selected cells (such as respiratory epithelial cells) and then administered systemically. For systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter can be used.

In yet another embodiment, the antisense oligonucleotide of the invention is an alpha-anomeric nucleic acid molecule. An alpha-anomeric nucleic acid molecule forms specific double-stranded hybrids with complementary RNA in which, contrary to the usual beta-units, the strands run parallel to each other (Gaultier et al., *Nucleic Acids. Res.* 15: 6625-6641 (1987)). The antisense nucleic acid molecule can also comprise a 2'-o-methylribonucleotide (Inoue et al. *Nucleic Acids Res.* 15: 6131-6148 (1987)) or a chimeric RNA-DNA analogue (Inoue et al. *FEBS Lett.,* 215: 327-330 (1987)).

Gene expression can be inhibited by targeting nucleotide sequences complementary to the regulatory region of the gene to form triple helical structures that prevent expression of the gene in target cells. See generally, Helene, C. *Anticancer Drug Des.* 6: 569-84 (1991); Helene, C. *Ann. N.Y. Acad. Sci.* 660: 27-36 (1992); and Maher, *Bioassays* 14: 807-15 (1992). The potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

Ribozymes

Ribozymes are a type of RNA that can be engineered to enzymatically cleave and inactivate other RNA targets in a specific, sequence-dependent fashion. By cleaving the target RNA, ribozymes inhibit translation, thus preventing the expression of the target gene. Ribozymes can be chemically synthesized in the laboratory and structurally modified to increase their stability and catalytic activity using methods known in the art. Alternatively, ribozyme encoding nucleotide sequences can be introduced into host cells through gene-delivery mechanisms known in the art. A ribozyme having specificity for STAT or ERK RNA can include one or more sequences complementary to the nucleotide sequence of at least a portion of STAT or ERK mRNA, and a sequence having known catalytic sequence responsible for mRNA cleavage (see U.S. Pat. No. 5,093,246 or Haselhoff and Gerlach *Nature* 334: 585-591 (1988)). For example, a derivative of a Tetrahymena L-19 IVS RNA can be constructed in which the nucleotide sequence of the active site is complementary to the nucleotide sequence to be cleaved in the STAT or ERK mRNA (see, e.g., Cech et al. U.S. Pat. No. 4,987,071; and Cech et al. U.S. Pat. No. 5,116,742). Alternatively, STAT or ERK mRNA encoding a STAT or ERK protein can be used to select a catalytic RNA having a specific ribonuclease activity from a pool of RNA molecules (see, e.g., Bartel, D. and Szostak, J. W. *Science* 261: 1411-1418 (1993)).

Nucleic Acid Targets

The nucleic acid targets of the polynucleotides useful as STAT or ERK inhibitors (e.g., antisense, RNAi, and ribozymes) may be any gene in the STAT or ERK pathways, or a portion of a gene in the STAT or ERK pathways. Optionally, a cocktail of polynucleotides specific for two or more genes may be administered to a subject. Thus, for example, the polynucleotide cocktail may include polynucleotides having nucleic acid targets in a STAT gene and an ERK gene. The nucleic acid target may be in any location within the STAT or ERK gene or transcript. For example, the nucleic acid target may be located at a site within a gene of the STAT or ERK pathway selected from the group consisting of the 5' untranslated region (UTR), transcription start site, translation start site, and the 3' UTR. In one embodiment, the nucleic acid target is located at a site within a STAT gene (such as the STAT1 or STAT3 gene) or ERK1/2 gene selected from the group consisting of the 5' untranslated region (UTR), transcription start site, translation start site, and the 3' UTR.

Pharmaceutical Compositions and Methods of Administration

The STAT or ERK inhibitors used in the compositions and methods of the subject invention can be incorporated into pharmaceutical compositions. Such compositions typically include the inhibitor and a pharmaceutically acceptable carrier. As used herein, the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions. Formulations (compositions) are described in a number of sources that are well known and readily available to those skilled in the art. For example, *Remington's Pharmaceutical Sciences* (Martin E. W., Easton Pa., Mack Publishing Company, 19$^{th}$ ed., 1995) describes formulations which can be used in connection with the subject invention.

Pharmaceutically acceptable carriers include any and all solvents (such as phosphate buffered saline buffers, water, saline), dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient (the STAT or ERK inhibitor), its use in therapeutic compositions is contemplated. Supplementary active ingredients can also be incorporated into the compositions. The pharmaceutical compositions of the subject invention can be formulated according to known methods for preparing pharmaceutically useful compositions. Formulations are described in a number of sources that are well known and readily available to those skilled in the art. For example, *Remington's Pharmaceutical Science* (Martin E. W. (1995) Easton Pa., Mack Publishing Company, 19$^{th}$ ed.) describes formulations which can be used in connection with the subject invention.

A pharmaceutical composition is formulated to be compatible with its intended route of administration, e.g., local or systemic. Examples of routes of administration include parenteral, e.g., intravenous, intradermal, subcutaneous, oral (e.g., inhalation), nasal, topical, transdermal, transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL (BASF, Parsippany, N.J.) or phosphate buffered saline (PBS). In all cases, the composition must be sterile and should be fluid to the extent that easy syringability exists. It should be stable under the conditions of manufacture and storage and be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. Isotonic agents, for example, sugars, polyalcohols such as manitol, sorbitol, sodium chloride can also be included in the composition. Prolonged absorption of the injectable compositions can be brought about by including in the composition an agent that delays absorption, such as aluminum monostearate or gelatin.

Sterile injectable solutions can be prepared by incorporating the active compound (e.g., a STAT or ERK inhibitor) in the required amount in an appropriate solvent with one or a combination of ingredients enumerated above, as required, followed by filtered sterilization. Generally, dispersions are prepared by incorporating the polynucleotide into a sterile vehicle, which contains a basic dispersion medium and the required other ingredients from those enumerated above. In the case of sterile powders for the preparation of sterile injectable solutions, suitable methods of preparation include vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Formulations suitable for nasal administration, wherein the carrier is a solid, include a coarse powder having a particle size, for example, in the range of about 20 to about 500 microns, which is administered in the manner in which snuff is taken, i.e., by rapid inhalation through the nasal passage from a container of the powder held close up to the nose. Suitable formulations wherein the carrier is a liquid for administration by nebulizer, include aqueous or oily solutions of the agent. For administration by inhalation, the STAT or ERK inhibitor can also be delivered in the form of drops or an aerosol spray from a pressured container or dispenser that contains a suitable propellant, e.g., a gas such as carbon dioxide, or a nebulizer. Such methods include those described in U.S. Pat. No. 6,468,798.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays, drops, or suppositories. For transdermal administration, the active compound (e.g., polynucleotides of the invention) are formulated into ointments, salves, gels, or creams, as generally known in the art.

The pharmaceutical compositions can also be prepared in the form of suppositories (e.g., with conventional suppository bases such as cocoa butter and other glycerides) or retention enemas for rectal delivery.

Polynucleotides that are STAT or ERK inhibitors, or which encode polypeptides that are STAT or ERK inhibitors, can also be administered by transfection or infection using methods known in the art, including but not limited to, the methods described in McCaffrey et al., *Nature* 418(6893): 38-39 (2002) (hydrodynamic transfection); Xia et al., *Nature Biotechnol.* 20(10): 1006-10 (2002) (viral-mediated delivery); or Putnam, *Am. J. Health Syst. Pharm.* 53(2): 151-160 (1996), erratum at *Am. J. Health Syst. Pharm.* 53(3): 325 (1996).

The polynucleotides can also be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in Hamajima et al., *Clin. Immunol. Immunopathol.* 88(2): 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996). Preferably, the polynucleotides used in the methods of the invention are administered to the subject such that an effective amount are delivered to the respiratory epithelial cells within the subject's airway, resulting in an effective amount of transcription and/or translation of the polynucleotides within the subject's airway.

In one embodiment, the polynucleotides are prepared with carriers that will protect the polynucleotide against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. Liposomal suspensions (including liposomes targeted to antigen-presenting cells with monoclonal antibodies) can also be used as pharmaceutically acceptable carriers. These can be prepared according to methods known to those skilled in the art, for example, as described in U.S. Pat. No. 4,522,811.

Preferably, the STAT or ERK inhibitors used in the method of the subject invention (e.g., compositions containing them) are administered locally or systemically such that they are delivered to the cells of the airway, such as airway epithelial cells, which line the nose as well as the large and small airways.

Toxicity and therapeutic efficacy of compositions can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions which exhibit high therapeutic indices can be used. While compositions that exhibit toxic side effects can be used, care should be taken to design a delivery system that targets such compounds to the site of affected tissue in order to minimize potential damage to uninfected cells and, thereby, reduce side effects.

Data obtained from cell culture assays and animal studies can be used in formulating a range of dosage for use in humans. The dosage of such compositions generally lies within a range of circulating concentrations that include the ED50 with little or no toxicity. The dosage can vary within this range depending upon the dosage form employed and the route of administration utilized. For any composition used in the method of the invention, the therapeutically effective dose can be estimated initially from cell culture assays. A dose can be formulated in animal models to achieve a circulating plasma concentration range that includes the IC50 (i.e., the concentration of the test composition which achieves a half-maximal inhibition of symptoms) as determined in cell culture. Such information can be used to more accurately determine useful doses in humans. Levels in plasma can be measured, for example, by high performance liquid chromatography.

In accordance with the invention, treatment of a subject with a therapeutically effective amount of a STAT or ERK inhibitor can include a single treatment or can include a series of treatments. The STAT or ERK inhibitor(s) can be administered on any appropriate schedule, e.g., from one or more times per day to one or more times per week; including once every other day, for any number of days or weeks, e.g., 1 day, 2 days, 3 days, 4 days, 5 days, 6 days, 1 week, 10 days, 2 weeks, 3 weeks, 4 weeks, 5 weeks, 6 weeks, 7 weeks, 8 weeks, 2 months, 3 months, 6 months, or more, or any variation thereon. The skilled artisan will appreciate that certain factors may influence the dosage and timing required to effectively treat a subject, including but not limited to the severity of the disease or disorder, previous treatments, the general health and/or age of the subject, and other diseases present.

The STAT or ERK inhbitor(s) used in the compositions and methods of the invention can be used in the form of salts. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include citric acid, lactic acid, tartaric acid, fatty acids, and the like.

Salts may also be formed with bases. Such salts include salts derived from inorganic or organic bases, for example alkali metal salts such as magnesium or calcium salts, and organic amine salts such as morpholine, piperidine, dimethylamine or diethylamine salts.

The polynucleotides used in the methods and compositions of the invention can be inserted into genetic constructs, e.g., viral vectors, retroviral vectors, expression cassettes, or plasmid viral vectors, e.g., using methods known in the art, including but not limited to those described in Xia et al., (2002), supra. Genetic constructs can be delivered to a subject by, for example, inhalation, orally, intravenous injection, local administration (see U.S. Pat. No. 5,328,470) or by stereotactic injection (see, e.g., Chen et al., *Proc. Natl. Acad. Sci. USA* 91: 3054-3057 (1994)). The pharmaceutical preparation of the delivery vector can include the vector in an acceptable diluent, or can comprise a slow release matrix in which the delivery vehicle is imbedded. Alternatively, where the complete delivery vector can be produced intact from recombinant cells, e.g., retroviral vectors, the pharmaceutical preparation can include one or more cells which produce the polynucleotide delivery system.

The polynucleotides of the invention can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21 nucleotides (Brummelkamp et al., *Science* 296: 550-553 (2002); Lee et al., (2002), supra; Miyagishi and Taira, *Nature Biotechnol.* 20: 497-500 (2002); Paddison et al. (2002), supra; Paul (2002), supra; Sui (2002) supra; Yu et al. (2002), supra.

The present invention also relates to vectors and to constructs that include or encode polynucleotides and in particular to "recombinant nucleic acid constructs" that include any nucleic acid such as a DNA polynucleotide segment that may be transcribed to yield STAT or ERK mRNA-specific siRNA polynucleotides according to the invention as provided above; to host cells which are genetically engineered with vectors and/or constructs of the invention and to the production of siRNA polynucleotides, polypeptides, and/or fusion proteins of the invention, or fragments or variants thereof, by recombinant techniques. Polynucleotides disclosed herein as RNA polynucleotides may be engineered to produce corresponding DNA sequences using well-established methodologies such as those described herein. Thus, for example, a DNA polynucleotide may be generated from any siRNA sequence described herein, such that the present siRNA sequences will be recognized as also providing corresponding DNA polynucleotides (and their complements). These DNA polynucleotides are therefore encompassed within the contemplated invention, for example, to be incorporated into the subject invention recombinant nucleic acid constructs from which siRNA may be transcribed.

According to the present invention, a vector may comprise a recombinant nucleic acid construct containing one or more promoters for transcription of an RNA molecule, for example, the human U6 snRNA promoter (see, e.g., Miyagishi et al., *Nat. Biotechnol.* 20: 497-500 (2002); Lee et al., *Nat. Biotechnol.* 20: 500-505 (2002); Paul et al., *Nat. Biotechnol.* 20: 505-508 (2002); Grabarek et al., *BioTechniques* 34: 73544 (2003); see also Sui et al., *Proc. Natl. Acad. Sci. USA* 99: 5515-20 (2002)). Each strand of a siRNA polynucleotide may be transcribed separately each under the direction of a separate promoter and then may hybridize within the cell to form the siRNA polynucleotide duplex. Each strand may also be transcribed from separate vectors (see Lee et al., supra). Alternatively, the sense and antisense sequences specific for an RSV sequence may be transcribed under the control of a single promoter such that the siRNA polynucleotide forms a hairpin molecule (Paul et al., supra). In such an instance, the complementary strands of the siRNA specific sequences are separated by a spacer that comprises at least four nucleotides, but may comprise at least 5, 6, 7, 8, 9, 10, 11, 12, 14, 16, 94 18 nucleotides or more nucleotides as described herein. In addition, siRNAs transcribed under the control of a U6 promoter that form a hairpin may have a stretch of about four uridines at the 3' end that act as the transcription termination signal (Miyagishi et al., supra; Paul et al., supra). By way of illustration, if the target sequence is 19 nucleotides, the siRNA hairpin polynucleotide (beginning at the 5' end) has a 19-nucleotide sense sequence followed by a spacer (which as two uridine nucleotides adjacent to the 3' end of the 19-nucleotide sense sequence), and the spacer is linked to a 19 nucleotide antisense sequence followed by a 4-uridine terminator sequence, which results in an overhang. siRNA polynucleotides with such overhangs effectively interfere with expression of the target polypeptide. A recombinant construct may also be prepared using another RNA polymerase III promoter, the H1 RNA promoter, that may be operatively linked to siRNA polynucleotide specific sequences, which may be used for transcription of hairpin structures comprising the siRNA specific sequences or separate transcription of each strand of a siRNA duplex polynucleotide (see, e.g., Brummelkamp et al., *Science* 296: 550-53 (2002); Paddison et al., supra). DNA vectors useful for insertion of sequences for transcription of an siRNA polynucleotide include pSUPER vector (see, e.g., Brummelkamp et al., supra); pAV vectors derived from pCWRSVN (see, e.g., Paul et al., supra); and pIND (see, e.g., Lee et al., supra), or the like.

Polynucleotides used in the methods and compositions of the invention can be expressed in mammalian cells, yeast, bacteria, or other cells under the control of appropriate promoters, providing ready systems for evaluation of STAT or ERK-specific polynucleotides that are capable of interfering with expression of STAT or ERK genes, as provided herein. Appropriate cloning and expression vectors for use with prokaryotic and eukaryotic hosts are described, for example, by Sambrook, et al., Molecular Cloning: A Laboratory Manual, Third Edition, Cold Spring Harbor, N.Y., (2001).

The appropriate DNA sequence(s) may be inserted into the vector by a variety of procedures. In general, the DNA sequence is inserted into an appropriate restriction endonuclease site(s) by procedures known in the art. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described, for example, in Ausubel et al. (1993 Current Protocols in Molecular Biology, Greene Publ. Assoc. Inc. & John Wiley & Sons, Inc., Boston, Mass.); Sambrook et al. (2001 Molecular Cloning, Third Ed., Cold Spring Harbor Laboratory, Plainview, N.Y.); Maniatis et al. (1982 Molecular Cloning, Cold Spring Harbor Laboratory, Plainview, N.Y.); and elsewhere.

The DNA sequence in the expression vector is operatively linked to at least one appropriate expression control (i.e., regulatory) sequence (e.g., a promoter or a regulated promoter) to direct mRNA synthesis. Representative examples of such expression control sequences include LTR or SV40 promoter, the E. coli lac or trp, the phage lambda $P_L$ promoter and other promoters known to control expression of genes in prokaryotic or eukaryotic cells or their viruses. Promoter regions can be selected from any desired gene using CAT (chloramphenicol transferase) vectors or other vectors with selectable markers. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art, and preparation of certain particularly preferred recombinant expression constructs comprising at least one promoter, or regulated promoter, operably linked to a polynucleotide of the invention is described herein.

As noted above, in certain embodiments the vector may be a viral vector such as a mammalian viral vector (e.g., retrovirus, adenovirus, adeno-associated virus, lentivirus). For example, retroviruses from which the retroviral plasmid vectors may be derived include, but are not limited to, Moloney Murine Leukemia Virus, spleen necrosis virus, retroviruses such as Rous Sarcoma Virus, Harvey Sarcoma virus, avian leukosis virus, gibbon ape leukemia virus, human immunodeficiency virus, adenovirus, Myeloproliferative Sarcoma Virus, and mammary tumor virus.

The viral vector includes one or more promoters. Suitable promoters that may be employed include, but are not limited to, the retroviral LTR; the SV40 promoter; and the human cytomegalovirus (CMV) promoter described in Miller, et al., Biotechniques 7: 980-990 (1989), or any other promoter (e.g., cellular promoters such as eukaryotic cellular promoters including, but not limited to, the histone, pol III, and beta-actin promoters). Other viral promoters that may be employed include, but are not limited to, adenovirus promoters, adeno-associated virus promoters, thymidine kinase (TK) promoters, and B19 parvovirus promoters. The selection of a suitable promoter will be apparent to those skilled in the art from the teachings contained herein, and may be from among either regulated promoters (e.g., tissue-specific or inducible promoters) or promoters as described above.

A tissue-specific promoter allows preferential expression of the polynucleotide in a given target tissue (such as tissue of the respiratory tract), thereby avoiding expression in other tissues. For example, to express genes specifically in the heart, a number of cardiac-specific regulatory elements can be used. An example of a cardiac-specific promoter is the ventricular form of MLC-2v promoter (see, Zhu et al., Mol. Cell Biol. 13: 4432-4444, 1993; Navankasattusas et al., Mol. Cell Biol. 12: 1469-1479, 1992) or a variant thereof such as a 281 bp fragment of the native MLC-2v promoter (nucleotides −264 to +17, Genebank Accession No. U26708). Examples of other cardiac-specific promoters include alpha myosin heavy chain (Minamino et al., Circ. Res. 88: 587-592, 2001) and myosin light chain-2 (Franz et al., Circ. Res. 73: 629-638, 1993). Endothelial cell gene promoters include endoglin and ICAM-2. See Velasco et al., Gene Ther. 8: 897-904, 2001. Liver-specific promoters include the human phenylalanine hydroxylase (PAH) gene promoters (Bristeau et al., Gene 274: 283-291, 2001), hB1F (Zhang et al., Gene 273: 239-249, 2001), and the human C-reactive protein (CRP) gene promoter (Ruther et al., Oncogene 8: 87-93, 1993). Promoters that are kidney-specific include CLCN5 (Tanaka et al., Genomics 58: 281-292, 1999), renin (Sinn et al., Physical Genomics 3: 25-31, 2000), androgen-regulated protein, sodium-phosphate cotransporter, renal cytochrome P-450, parathyroid hormone receptor and kidney-specific cadherin. See Am. J. Physiol. Renal Physiol. 279:F383-392, 2000. An example of a pancreas-specific promoter is the pancreas duodenum homeobox 1 (PDX-1) promoter (Samara et al., Mol. Cell Biol. 22: 4702-4713, 2002). A number of brain-specific promoters may be useful in the invention and include the thy-1 antigen and gamma-enolase promoters (Vibert et al., Eur. J. Biochem. 181: 33-39, 1989), the glial-specific glial fibrillary acidic protein (GFAP) gene promoter (Cortez et al., J. Neurosci. Res. 59: 39-46, 2000), and the human FGF1 gene promoter (Chiu et al., Oncogene 19: 6229-6239, 2000). The GATA family of transcription factors have promoters directing neuronal and thymocyte-specific expression (see Asnagli et al., J. Immunol. 168: 4268-4271, 2002).

In a specific embodiment of the expression vector (e.g., viral or non-viral) of the subject invention, the promoter is H1 or U6. Preferably, the expression vector (e.g., viral or non-viral) of the subject invention includes a tissue-specific promoter such as surfactant protein B (SPB) and/or a steroid response element (SRE), such as the glucocorticoid response element (GRE) (Bohinski, R. J. et al. J. Biol. Chem., 1993, 268(15): 11160-11166; Bohinski, R. J. et al. Mol. Cell Biol., 1994, 14(9): 5671-5681; Itani, O A. et al. Am. J. Physiol. Endocrinol. Metab., 2002, 283(5):E971-E979; Huynh, T. T. et al. J Endocrinol., 2002, 172(2): 295-302). Such regulatory sequences are particularly useful where selective expression of the operably linked polynucleotide within the subject's airway is desired and/or where expression of the polynucleotide only in the presence of steroids is desired. For example, it may be desirable to administer a polynucleotide encoding a STAT or ERK inhibitor operably linked to a steroid response element, wherein a steroid is co-administered to the subject as combination therapy.

Identification of STAT or ERK Inhibitors

Another aspect of the invention concerns a method for identifying agents useful for treating or reducing the likelihood of developing an RSV infection by determining whether a candidate agent acts as an inhibitor of signal transducers and activators of transcription (STAT) or ERK1/2 signaling, wherein inhibition of STAT or ERK1/2 signaling is indicative of an agent useful for treating or reducing the likelihood of developing RSV infection. Optionally, the method further includes the step of manufacturing the inhibitor. Optionally, the method further includes the step of formulating the inhibitor for delivery to the respiratory epithelium. The activity of agents potentially useful as inhibitors may be assayed in vitro, in vivo, or in a cell line. Using ERK as an example, in vitro assays include assay that determine inhibition of either the kinase activity or ATPase activity of activated ERK. Alternate in vitro assays quantitate the ability of the inhibitor to bind to ERK and may be measured either by radiolabelling the inhibitor prior to binding, isolating the inhibitor/ERK complex, and determining the amount of radiolabel bound, or by running a competition experiment where new inhibitors are incubated with ERK bound to known radioligands. One may use any type or isoform of ERK, depending upon which ERK type or isoform is to be inhibited.

As used in this specification, including the appended claims, the singular "a" "a" and "the" include plural reference unless the contact dictates otherwise. Thus, for example, a reference to "a STAT inhibitor" includes more than one such STAT inhibitor. A reference to "an ERK inhibitor" includes more than one such ERK inhibitor. A reference to "a cell" includes more than one such cell.

The terms "comprising", "consisting of" and "consisting essentially of" are defined according to their standard meaning. The terms may be substituted for one another throughout the instant application in order to attach the specific meaning associated with each term.

MATERIALS AND METHODS FOR EXAMPLES 1-5

Virus and Cell Lines.

The RSV A2 long strain (VR-1302) and the human lung epithelial cell lines A549 and HEp-2 were obtained from the American Type Culture Collection (ATCC, Rockville, Md.). Normal human bronchial epithelial (NHBE) cells were obtained from CLONETICS (San Diego Calif.). Cell lines were grown at 37° C. in 5% $CO_2$ in Earle's modified Eagle's medium (EMEM), supplemented with 10% fetal bovine serum. NHBE primary cells were cultured in the supplemented medium provided by the supplier.

Reagents.

AG490, a JAK2 inhibitor was purchased from CALBIOCHEM (San Diego, Calif.). STAT-1 WT and DN constructs were obtained from Dr. Richard Jove of Moffitt Cancer Center, University of South Florida. Antibodies to IL-6 were purchased from PHARMINGEN. Heparin and heparinase were from SIGMA.

RSV Purification and Plaque Assay.

Supernatants from RSV-infected HEp-2 cells (supRSV) were clarified by centrifugation at 3200 g for 20 minutes at 4° C. and PEG 8000 (50%, w/v) was added to a final concentration of 10% (Mbiguino, A. and Menezes, J. *J. Virol. Methods*, 1991, 31(2-3): 161-170; Senterfit, L. B. and Baldridge, P. B. *J. Immunol. Methods*, 1974, 4(2): 349-357). Virus was precipitated for 90 minutes at 4° C. with stirring, followed by centrifugation at 3200 g for 20 minutes at 4° C. Pellets were snap frozen and stored at −80° C. PEG-precipitated virus was purified on two successive sucrose density gradients. The virus was layered on a discontinuous 30%, 45%, and 60% (w/v in 150 mM NaCl, 50 mM Tris-HCl, and 1 mM EDTA, pH 7.5) sucrose gradient and centrifuged 90 minutes at 35,000 rpm in an SW-41 rotor. The visible band between 30% and 45% was collected, diluted 1:2, and layered on a continuous 30-60% sucrose gradient for 18 hours at 35,000 rpm in an SW-41 rotor. Fractions (purRSV) were analyzed by spectrophotometry and viral titering using a HEp-2 cell-based plaque assay, as described (Behera, A. K. et al. *Biochem. Biophys. Res. Commun.*, 2001, 280(1): 188-195).

Heparin and Heparinase Treatment.

RSV was incubated with 1000 U/ml heparin at 37° C. for 2 hours and then used to infect A549 cells for 30 minutes at 37° C. After treatment, the cells were washed with PBS and total protein was extracted. A549 cells were also incubated with 1000 U/ml heparin for 2 hours at 37° C. and then infected with RSV for 30 minutes at 37° C. for 2 hours before total protein was extracted. For heparinase treatment, RSV or cells were similarly treated with 10 U/ml heparinase.

Immunofluorescence.

RSV-infected and uninfected cells were fixed in chilled acetone for 10 minutes, air-dried, and stained for 30 minutes at 37° C. with FITC-labeled anti-RSV mAbs (CHEMICON, Temecula, Calif.). The slides were washed three times in PBS-Tween 20, air dried, mounted with Fluoromount G (FISHER, Pittsburgh, Pa.), and observed by fluorescence microscopy. RSV-positive cells were counted in 15 random fields and from 2 to 3 different slides for each treatment group.

Immunoblotting.

Immunoblotting was carried out as previously described (Behera, A. K. et al. *Biochem. Biophys. Res. Commun.*, 1998, 251(3): 704-709). After transfer, membranes were blocked with 5% non-fat dried milk, incubated with antibody to a specific STAT protein or to the corresponding phospho-STAT protein (NEW ENGLAND BIOLABS, Beverly, Mass.), secondary antibody conjugated to horseradish peroxidase was added, and immunocomplexes detected by enhanced chemiluminescence (NEW ENGLAND BIOLABS, Beverly, Mass.).

Immunocytochemistry.

A549 cells were cultured to 45-50% confluence on 8-well slides in EMEM. NHBE cells were cultured in BEGM (CLONETICS, CA) with 0.5% FBS. Cells were infected with supRSV or purRSV at an MOI of 1 for 30 minutes, after which they were washed with PBS and fixed in cold methanol for 10 minutes. After three washes with TBST (50 mM Tris-HCl, pH 7.4, 150 mM NaCl, and 0.1% Triton X-100), the slides were blocked with 5.5% normal goat serum in TBST for 1 hours, washed with TBS, and incubated with primary antibody in TBS/3% BSA overnight at 4° C. Cells were washed, incubated with secondary antibody, and developed using the VECTASTAIN ABC Kit (VECTOR LABORATORIES, Burlingame, Calif.). Control cells were either mock infected (no RSV) or treated with an equivalent concentration of sucrose.

DNA Transfection.

A549 cells were grown to 60% confluence and transfected with 12 μg of either WT or dominant-negative STAT-1 DNA and a pRL-TK plasmid (PROMEGA) at a 10:1 ratio and 35 μl Lipofectin (LIFE TECHNOLOGY, Gaithersburg, Md.) for 15 hours at 37° C. Transfection medium was replaced with complete growth medium, cells were incubated at 37° C. for 6 hours, and infected with supRSV at MOI of 1 for 30 minutes at 37° C. *Renilla* luciferase (pRL-TK) activity was used to normalize transfection efficiency.

Differential Gene Expression Analysis.

The protocols for cRNA preparation, target hybridization, fluidics station setup, the probe array scan, and data analysis were according to the Affymetrix technical manual (AFFYMETRIX, Santa Clara, Calif.). Briefly, 10 μg total RNA was isolated from uninfected and RSV-infected A549 cells and used to synthesize cDNA. The cDNA was used as an in vitro transcription template to make a biotinylated cRNA probe for hybridization to chips (HUGENEFL array, AFFYMETRIX, CA) carrying 5000 human genes. Probe arrays were scanned and results were processed using AFFYMETRIX GENECHIP 3.0 software. Gene expression profiles were created after all data sets were raised to a uniform value and normalized with all genes. A change in expression of a specific gene was considered to be significant if the average difference across the probe set was greater than 2-fold.

Promoter Analysis.

The promoter regions of early growth response (EGR-1), c-Fos, zinc-finger transcription factor (ZFTF), and IL-6, were analyzed using MATINSPECTOR V2.2 (GENOMATIX software GmbH). Potential cis-regulatory elements and critical sequences shown are based on analysis of 5' upstream sequences from GenBank.

Reverse Transcriptase-Polymerase Chain Reaction.

Reverse transcriptase-polymerase chain reaction (RT-PCR) was performed, as previously described (Behera, A. K. et al. *Biochem. Biophys. Res. Commun.*, 2001, 280(1): 188-195). A PCR cycle comprised 94° C. (5 minutes); 94° C. (1 minutes), 56° C. (30 seconds), and 72° C. (1 minute); and 72° C. for 7 minutes. Runs of 22, 25, 32, 35, and 40 cycles for each sample were used to determine the linear amplification range. RT-PCR was repeated three times at that cycle and products quantified by densitometry normalized with respect to -actin as internal control. The forward (fp) and reverse (rp) primers used were: Egr-1-fp, 5'-CCC CTT CCC CAA TTA CTA TTC C-3' (SEQ ID NO:1); Egr-1-rp, 5'-CCA AGT GAG GAC CTA ACT CC-3' (SEQ ID NO:2); cFos-fp, 5'-CCT TCG TCT TCA CCT ACC C-3' (SEQ ID NO:3); cFos-rp, 5'-GAA GAG GTA AGG ACT TGA GTC C-3' (SEQ ID NO:4); ZFTF-fp, 5'-TTC TGA GTG ACA AAG TGA CTG C-3' (SEQ ID NO:5); ZFTF-rp, 5'-TAG GAG ACA GAT TTG GGC AGG-3' (SEQ ID NO:6); -actin-fp, 5'-CGC GAG AAG ATG ACC CAG-3' (SEQ ID NO:7); -actin-rp, 5'-ATC ACG ATG CCA GTG GTA C-3' (SEQ ID NO:8); IL6-fp, 5'-AAC TCC TTC TCC ACA AGC G-3' (SEQ ID NO:9); IL6-rp, 5'-TGG ACT GCA GGA ACT CCT T-3' (SEQ ID NO:10); RSV N-fp, 5' GCG ATG TCT AGG TTA GGA AGA A-3' (SEQ ID NO:11); and RSV N-RP, 5'-GCT ATG TCC TTG GGT AGT AAG CCT-3' (SEQ ID NO:12).

Promoter-Reporter Gene Expression Analysis.

The IL-6 promoter sequence was cloned upstream of a green-fluorescent protein reporter to generate plasmid pIL6-EGFP. pIL6-EGFP was transfected into A549 cells using LIPOFECTAMINE PLUS (INVITROGEN) in serum-free media for 6 hours. After transfection, cells were treated with medium alone or infected with RSV. Twenty-four hours later, cells were fixed in 2% paraformaldehyde and analyzed on a FACScan flow cytometer (BECTON-DICKINSON, Mountainview, Calif.).

Electrophoretic Mobility Shift Assay.

A549 cells were grown to 85-90% confluence and infected with RSV for 15 or 30 minutes at 37° C. Nuclear extracts were prepared by subjecting cells to three cycles of freeze-thaw (dry ice/ethanol and 37° C.). After centrifugation (10,000 g, 4° C., 1 minute), pellets were resuspended in buffer containing 0.2 mM EDTA, 20 mM Hepes, 1.5 mM MgCl2, 420 mM KCl, 25% glycerol, 1 μl/ml leupeptin, 1 μg/ml pepstatin, 1 mM DTT, and 1 mM PMSF and stored at −70° C. The Sis-inducible element (SIE, 5'-AGCTTCATTTCCCGTAAATC-CCTA-3' (SEQ ID NO:13)) was used as probe for STAT binding. The probe was labeled with [$^{32}$P]dATP (10 mCi/ml; AMERSHAM LIFE SCIENCE), using Klenow fragment and Labeling Mix (PHARMACIA BIOTECH) at room temperature for 30 minutes. DNA-binding reactions containing 40,000 cpm of labeled probe and 2-6 μg cytosolic protein extract were incubated 30 minutes at 30° C. and run on a 5% polyacrylamide gel. Gels were fixed, dried, and exposed to a storage phosphor screen visualized using a MOLECULAR DYNAMICS PHOSPHORIMAGER.

Statistical Analysis.

All experiments were repeated 2-3 times and representative experiments are shown. Experiments involving enumeration or quantification followed a paired experimental design. Three replicates were used for each treatment and mean values of the replicates were used to compare difference between treatments. A two-sided paired t test was used to compare difference between means. A $p < 0.05$ level of significance (two-sided) was utilized.

EXAMPLE 1

RSV-Induced Early Gene Expression Analysis Suggests Involvement of STATs

Figure 1A:
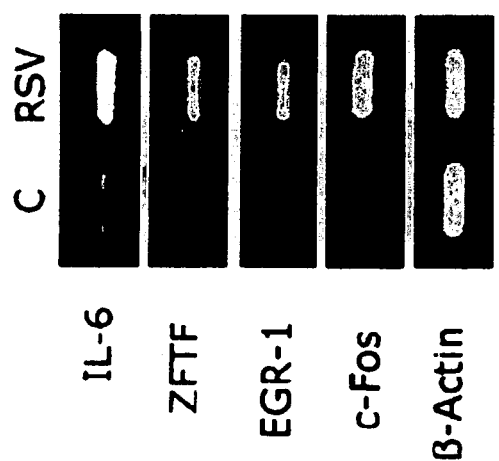
Figure 1C:
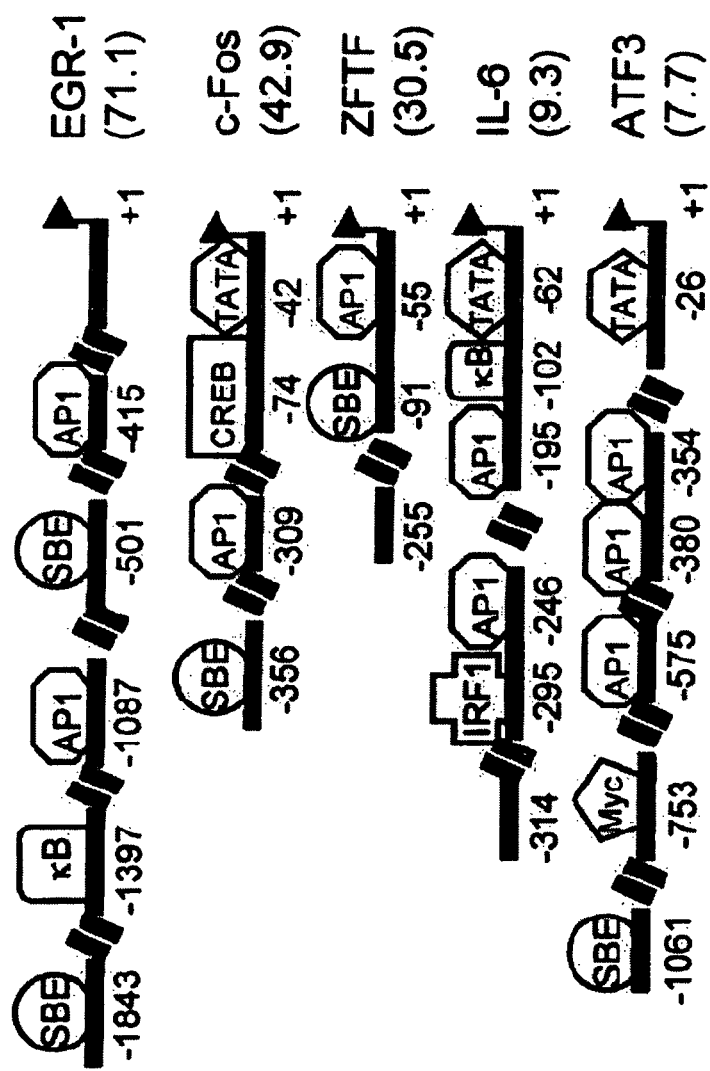

In an effort to identify and characterize the molecules participating in early signaling pathways, differential gene expression in supRSV-infected A549 cells was performed. Analysis of RNAs from uninfected control and supRSV-infected A549 cells revealed altered expression of 53 genes. Expression ranged from a 5.5-fold reduction to a 56.4-fold increase and genes showing >3-fold changes in expression in RSV-infected cells are listed in Table 1. Expression of five genes was downregulated 2.2-5.5-fold in cells infected with RSV compared to the control (data not shown). Four regulatory genes, early growth response (EGR-1), c-Fos, zinc-finger transcription factor (ZFTF), and interleukin-6 (IL-6), were upregulated 2-10-fold as measured by RT-PCR (FIGS. 1A and 1B). These genes were selected based on their high expression as well as their potential role in viral pathogenesis. Northern blot analysis of control and RSV-infected cells showed that ZFTF and EGR-1 mRNA can be detected 30-60 minutes after RSV exposure (data not shown). The promoter regions of RSV-activated regulatory genes from microarray analysis are shown in FIG. 1C. Early gene activation potentially involves several transcription factors including STATs, which have heretofore not been described in RSV-infected cells.

TABLE 1

| Probe set | Gene description | Fold change |
|---|---|---|
| M57731 | Gro-b | 56.4* |
| X52541 | Early growth response gene (Egr-1) | 55.1 * |
| V01512 | c-Fos cellular oncogene | 29.3 |
| M92843 | Zinc-finger transcription factor (ZFTF) | 24.2 |
| X04602 | Interleukin 6 (IL-6) | 19.8* |
| L19871 | Activating transcription factor | 8.3* |
| D28235 | Prostaglandin-endoperoxide synthase-2 | 7.9* |
| X51345 | JUN-B protein (Jun-B) | 5.6 |
| U04636 | Cyclooxygenase-2 (hCox-2) | 4.8 |
| U44975 | DNA-binding protein (CPBP) | 4.0 |

TABLE 1-continued

| Probe set | Gene description | Fold change |
|---|---|---|
| U15932 | Protein phosphatase | 3.8 |
| HG4069 | Monocyte chemotactic protein 1 (MCP-1) | 3.2* |

Changes in mRNA expression in A549 epithelial cells following a 30-minute exposure to respiratory syncytial virus

EXAMPLE 2

RSV Exposure Induces STAT-1α in A549 and NHBE Cells

Figure 2A:
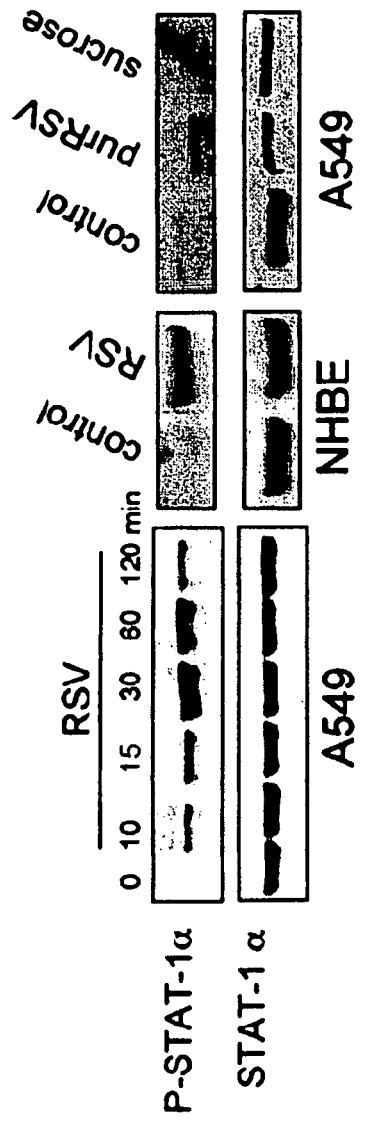
Figure 2B:
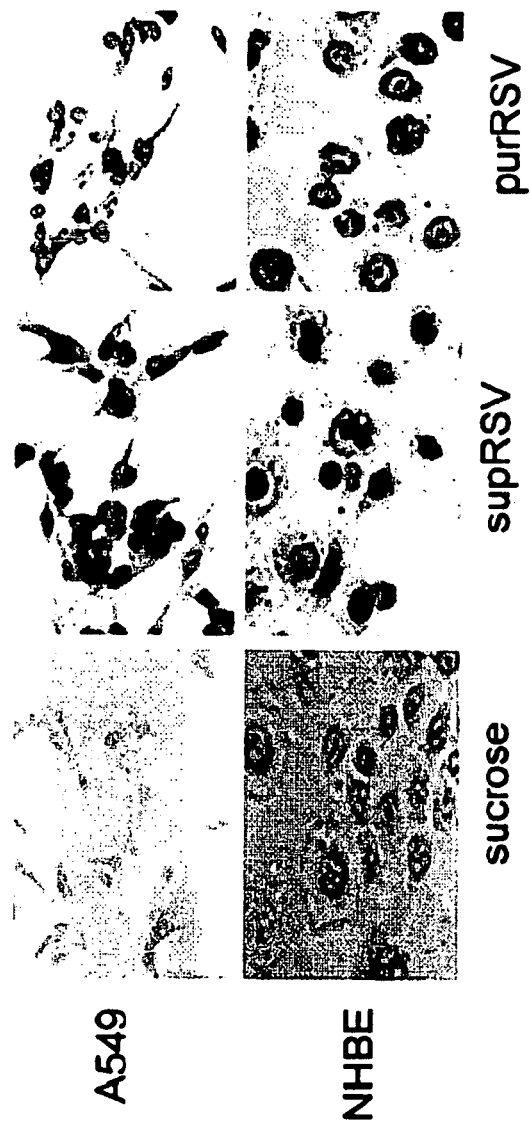

RSV infection induced the phosphorylation of STAT-1α in A549 cells with maximum phosphorylation at 30 minutes and a decrease 1-2 hours after RSV infection (FIG. 2A). To determine if STAT phosphorylation was specific to A549 cells, primary cultures of NHBE cells were exposed to RSV for 30 minutes. NHBE cells also activated STAT-1α in response to RSV (FIG. 2A). Factors are present in the viral supernatant that might affect STAT-1α phosphorylation; therefore, RSV was purified by sucrose gradient centrifugation to remove these factors. Exposure of A549 cells to purified RSV (purRSV) also induced STAT-1α phosphorylation (FIG. 2A). To verify that phosphorylation activated STAT-1, the nuclear localization of phospho-STAT-1 was examined by immunofluorescence. A549 and NHBE cells were exposed to supRSV or purRSV at an MOI of 1 for 30 minutes and stained with antibody to phospho-STAT-1α. Both supRSV and purRSV induced nuclear localization of STAT-1α (FIG. 2B).

EXAMPLE 3

RSV Attachment is Critical to STAT Activation

Figure 3A:
FIGS. 3A and 3B show that RSV infection is necessary for STAT-1α phosphorylation. A549 cells were infected for 30 minutes with RSV or with RSV incubated with isotype-matched control antibody (C), polyclonal RSV antibody (xRSV), mAb to G protein (xG) or mAb to F protein (xF). Bound RSV was removed by immunoprecipitation with protein A-Sepharose. Lysates were blotted and probed with anti-phospho-STAT-1α, then re-probed with anti-STAT-1α. Results are shown in FIG. 3A. A549 cells were treated with heparinase 10 U/ml (lane 3) or heparin 1000 U (lane 5), then infected with RSV for 30 minutes or infected with virus pretreated (for 30 minutes) with heparinase 10 U/ml (lane 4) or heparin 1000 U (lane 6) before adding to cells. Lysates were blotted and probed with anti-phospho-STAT-1α, then re-probed with anti-STAT-1α. Results are shown in FIG. 3B.
Figure 3B:
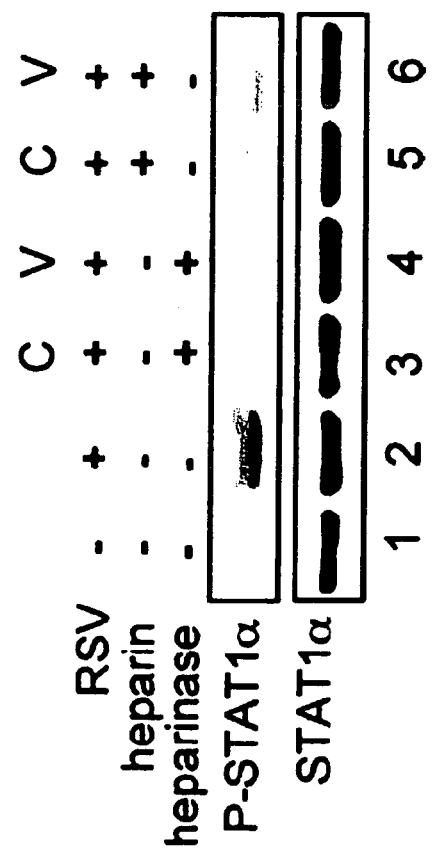

RSV suspensions were incubated with antibodies to the RSV F or G protein (CHEMICON, Temecula, Calif.) and immunoprecipitated with protein A-Sepharose to deplete them of RSV. RSV depletion blocked STAT-1α activation, as shown in FIG. 3A, indicating that interaction of epithelial cells with RSV is required for STAT-1α phosphorylation. RSV infection involves attachment of G proteins to cellular peptidoglycans, such as heparan sulfate, and fusion with the cell membrane via the viral F protein. Treatment of cells with heparin or heparinase blocks RSV infection (Feldman, S. A. et al. *J. Virol.*, 1999, 73(8): 6610-6617). RSV-induced activation of STAT-1 was abolished in A549 cells treated with heparin or heparinase or infected with RSV that had been pretreated with heparin or heparinase, as shown in FIG. 3B. These experiments indicate that RSV attachment is required for STAT-1α activation.

EXAMPLE 4

Blocking STAT-1 Attenuates RSV Infection

Figures 4D, 4E, 4F:
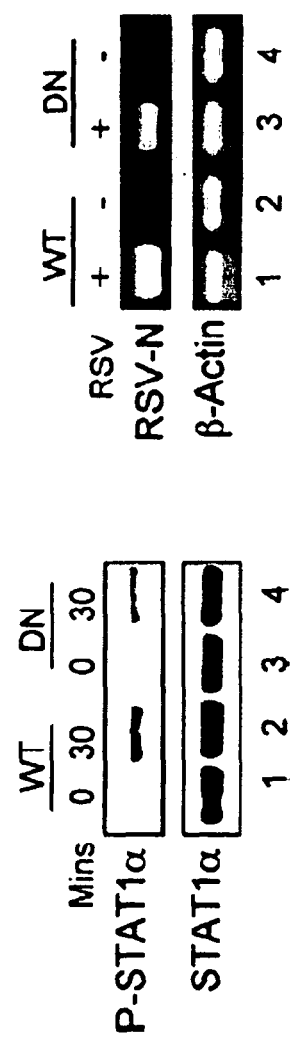

To further establish the role of STATs in RSV infection, A549 cells were preincubated with AG490 for 4 hours, an inhibitor of JAK, before infection with supRSV. AG490 decreased phosphorylation of STAT-1α in RSV-infected A549 cells compared to untreated controls, as shown in FIG. 4A. Treatment with AG490 also significantly (p<0.001) decreased RSV infection, as determined by a plaque assay. Viable cell counts on control and AG490-treated cells showed that AG490 at these doses had no cytotoxic or anti-proliferative effects, as shown in FIG. 4B. A more specific inhibition of STAT activation was obtained by transfecting A549 cells with a dominant-negative (Y701F, DN) STAT-1α (FIG. 4C). Cells transfected with DN-STAT-1α showed a decrease in phospho-STAT-1α (FIG. 4D) and RSV-N gene transcription (FIG. 4E), compared to WT. Immunofluorescence analysis of infected cells 24 hours after RSV exposure showed a >60% decrease in RSV-infected A549 cells transfected with the DN construct, as shown in FIG. 4F. There was no difference in growth between the cultures transfected with the wild type or the DN constructs (data not shown). These results suggest that STAT-1α activation is necessary for RSV infection.

EXAMPLE 5

STAT-3 is Also Involved in RSV Infectivity and is Induced by IL-6

Figure 5A:
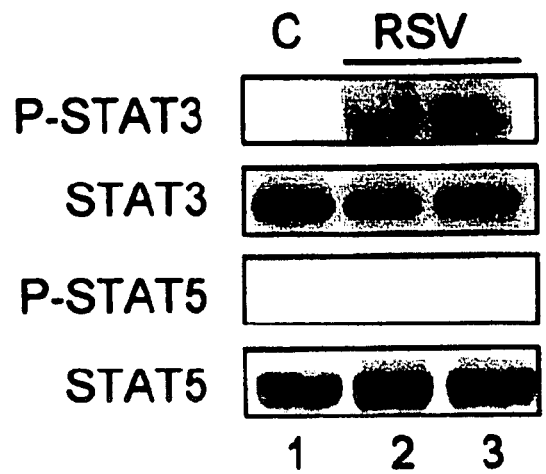
Figure 5B:
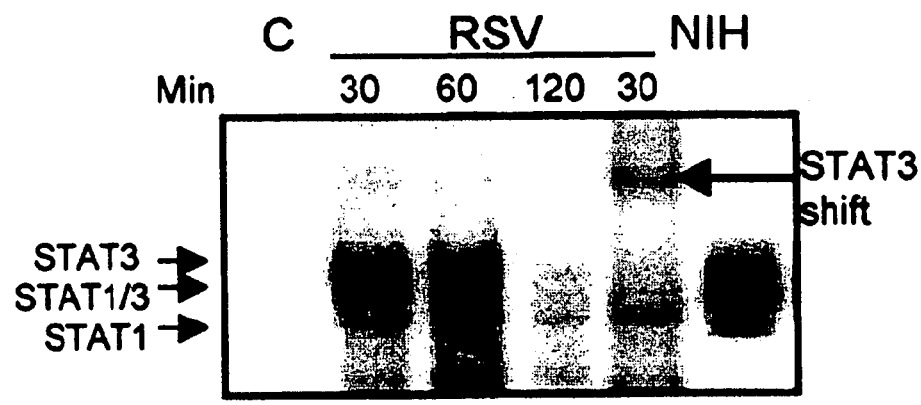
Figure 5C:
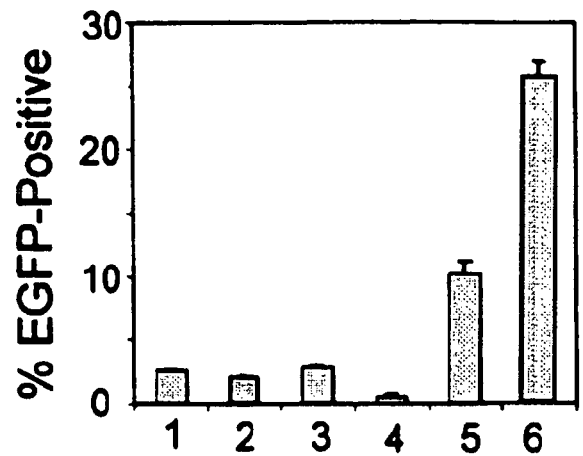
Figure 5D:
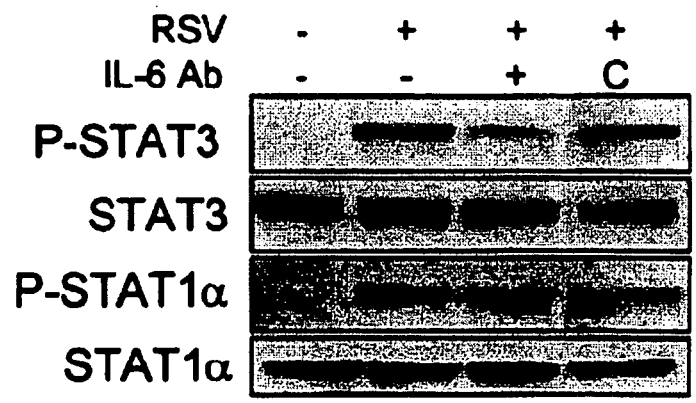
Figure 5E:
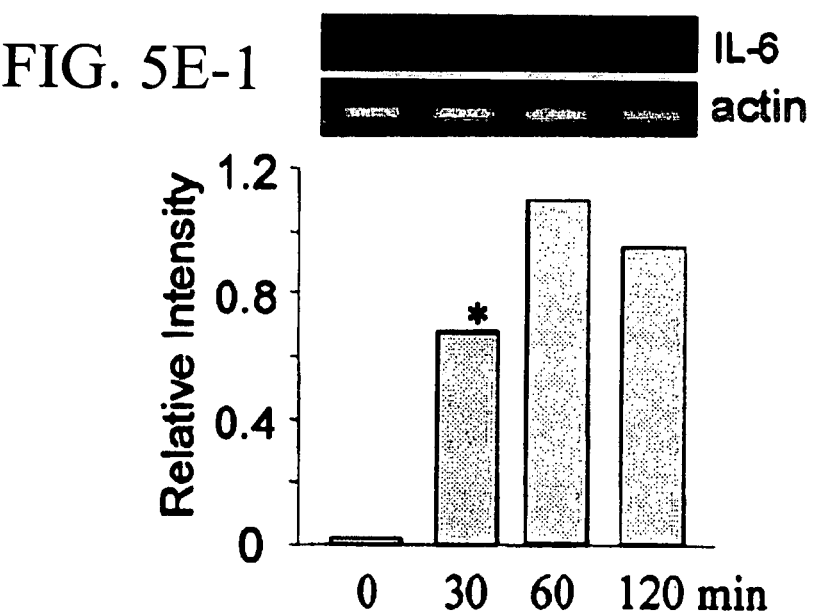

To investigate the possibility that RSV infection activates other STATs, the phosphorylation of STAT-3 and STAT-5 was examined using two different preparations of RSV (FIG. 5A). STAT-3 phosphorylation but not STAT-5 was observed. Analysis of nuclear extracts by electrophoretic mobility shift showed binding of both STAT-1α and STAT-3 and a supershift with anti-STAT-3 antibody, as shown in FIG. 5B. Since the microarray analysis showed that IL-6 was highly upregulated in RSV-infected cells, the possibility that RSV activates STAT-3 secondary to IL-6 induction was examined. A reporter gene, enhanced green-fluorescent protein (EGFP), was cloned downstream of the IL-6 promoter and cells were transfected with this construct and infected with RSV. Both purRSV- and supRSV-induced EGFP expression, as shown in FIG. 5C. Incubation of supRSV with anti-IL-6 prior to infection of A549 cells resulted in decreased STAT-3 activation; STAT-1 was unaffected (FIG. 5D). RT-PCR analysis of IL-6 mRNA from cells infected with purified RSV showed induction of IL-6 mRNA within 30 minutes of infection (*p<0.0001), as shown in FIGS. 5E and 5E1. These data demonstrate that RSV induces IL-6, which in turn activates STAT-3 in A549 cells.

This investigation of RSV-induced early gene expression and signaling processes in A549 epithelial cells demonstrated changes in the expression of several genes and activation of the STAT-1α and STAT-3 signaling pathways, which are critical to early gene activation and a successful infection. The identification by microarray analysis of 53 differentially regulated genes in A549 cells exposed to RSV is consistent with changes in gene expression reported in other studies (Garofalo, R. et al. *J. Immunol.*, 1996, 157(6): 2506-2513; Bitko, V. et al. *Virology*, 1997, 232(2): 369-378; Elias, J. A. et al. *J. Biol. Chem.*, 1994, 269(35): 22261-22268; Zhu, H. et al. *Proc. Natl. Acad. Sci. USA*, 1998, 95(24): 14470-14475; Eckmann, L. et al. *J. Biol. Chem.*, 2000, 275(19): 14084-14094). The microarray data were confirmed by RT-PCR and Northern blot analyses that showed elevated expression of regulatory genes in RSV-infected cells. The key finding from the microarray results is that RSV-induced early gene expression involves STAT activation. Early genes such as RANTES, ICAM-1, and iNOS have STAT-binding elements (SBE) in their 5' promoters and are reported to be regulated by STAT activation (Cremer, I. et al. *FEBS Lett.*, 2002, 511(1-3): 41-45; Roy, J. et al. *J. Biol. Chem.*, 2001, 276(18): 14553-14561). RSV-upregulated genes identified by the microarray analysis were also found to have STAT-binding sites. Primary cultured normal human lung epithelial cells exhibited RSV-induced gene expression paralleling that in neoplastic A549 cells, showing that the observed activation of STAT-1α also occurs ex vivo in normal cells. Constituents in the RSV- HEP-2 supernatant might potentially activate STATs, but demonstration that purified RSV also activates STAT-1α and that depletion of RSV from the supernatant abrogates STAT-1α phosphorylation clearly implicates RSV infection in the activation of STAT-1α.

Pretreatment of cells with the JAK inhibitor AG490 prior to RSV infection caused a significant decrease in STAT-1α phosphorylation, suggesting that RSV activates STAT-1α via the JAK-STAT pathway. AG490 at doses that did not affect cell proliferation strongly inhibited RSV infection. Although the mechanism of the AG490-mediated decrease in RSV infection is unclear, the early signaling molecules seem to have a definitive role in the infection process. Further confirmation of the importance of STAT-1α in successful RSV infection was obtained by transfecting cells with dominant-negative STAT-1α DN-STAT-1α expression inhibited STAT-1α activation, decreased expression of RSV-N-gene transcripts, and reduced the numbers of infected cells compared to wild type.

The microarray data showed rapid and significant induction of IL-6, which prompted the examination of whether STAT-3 or STAT-5 was involved in RSV infection. RSV induced the activation of STAT-3 but not STAT-5, as evidenced by STAT-3 phosphorylation and a mobility shift assay. STAT-3 activation was also found to be dependent upon the expression of IL-6. Whether, STAT-3 plays an important role in regulating specific genes that are critical to RSV replication and successful infection is being investigated.

This report establishes for the first time that RSV induces the expression of a number of early genes in epithelial cells some of which may be critical to RSV infection. STAT-1α and STAT-3, which upregulate a number of these genes, are activated by RSV and determine the magnitude of the infection and accompanying inflammation. It has been reported that STAT-1α is constitutively activated in asthmatics (Sampath, D. et al. *J. Clin. Invest.*, 1999, 103(9): 1353-1361). Since RSV is one of the earliest triggers of airway inflammation and exacerbation of asthma, and a majority of infants experience RSV infection in the first two years of life, RSV may be instrumental in the initial airway activation-switching on an autocrine loop that is responsible for the inflammatory cascade and constitutive expression of STAT-1α in asthmatics.

MATERIALS AND METHODS FOR EXAMPLES 6-9

Virus Strains and Cell Culture.

RSV A2 strain was obtained from the American Type Culture Collection (ATCC, Rockville, Md., USA). In some experiments, rgRSV (an engineered RSV expressing enhanced green fluorescent protein) was used. A549 cell line, representing type II alveolar epithelial cells, was obtained from the ATCC. The cells were grown at 37° C. in 5% $CO_2$ in RPMI medium, supplemented with 10% fetal bovine serum. Normal human bronchial epithelial cells (NHBE) were obtained from CAMBREX (Walkersville, Md., USA) and grown in serum-free bronchial epithelium growth medium supplemented as indicated by the manufacturer. NHBE at passage 2 and 3 was used for the experiments.

Reagents.

Heparin and heparinase were obtained from Sigma-Aldrich (St. Louis, Mo., USA). AG490 (Janus kinase (JAK) inhibitor), PD98059 (MAPK/ERK kinase-1 (MEK-1) inhibitor), were obtained from CALBIOCHEM (San Diego, Calif., USA). Polyclonal anti-phospho antibodies or antibodies to STAT-1, ERK, or IκBα were obtained from CELL SIGNALING (Beverly, Mass., USA). Fluorescein isothiocyanate (FITC)-labeled anti-RSV N mouse monoclonal antibody was obtained from CHEMICON (Temecula, Calif., USA).

Treatment with Inhibitors.

A549 cells were incubated with AG490 (50 μM) or PD98059 (80 μM) for 4 hours at 37° C. and then infected with RSV. At 30 minutes, 60 minutes, and 240 minutes following infection, the cells were washed with phosphate-buffered saline (PBS) and the total protein extracted (see Immunoblotting). In some experiments, subconfluent NHBE cells were exposed to AG490 (50 μM) and PD98059 (80 μM) for 2 hours at 37° C. prior to rgRSV infection.

Heparin and Heparinase Treatment.

Either A549 cells or RSV was incubated with 1000 U/ml heparin at 37° C. for 2 hours before proceeding to infection for 30 minutes at 37° C. After treatment, the cells were washed with PBS and total protein was extracted. In some experiments, heparinase (10 U/ml) was used following the same protocol explained above.

RSV Purification and Plaque Assay.

RSV was PEG-precipitated and purified on two successive sucrose density gradients as described (Kong, X. et al. *Biochem. Biophys. Res. Commun.*, 2003, 306: 616-622). The plaque assay was used to determine infectious viral titers of purified fractions, as described (Behera, A. K. et al. *Biochem. Biophys. Res. Commun.*, 2001, 280: 188-195; Kong, X. et al. *Biochem. Biophys. Res. Commun.*, 2003, 306: 616-622). Because of the possible contamination of ATCC RSV with human adenovirus type 1, the purified preparations were tested for the presence of adenovirus by polymerase chain reaction using specific primers that amplify a product of 213 base pairs as previously reported by Cameron et al. (Cameron, R. et al. *Virus Res.*, 2003, 92: 151-156) and found that the preparations were not contaminated with adenovirus.

Immunofluorescence.

Acetone-fixed cells were stained with FITC-labeled anti-RSV monoclonal antibodies, as described (Kong, X. et al. *Biochem. Biophys. Res. Commun.*, 2003, 306: 616-622). RSV-positive cells (green fluorescence) were counted randomly from 15 different spots and from two or three different slides for each treatment group and the percentages of infected cells were plotted for wild type (WT) and dominant negative (DN) mutant cells.

Immunoblotting.

Whole cell protein extracts were prepared by lysing cells in 50 mM HEPES, 150 mM NaCl, 1 mM EDTA, 1 mM EGTA, 10% glycerol, 0.5% NP-40, 0.1 mM phenylmethylsulfonyl fluoride, 2.5 μg/ml leupeptin, 0.5 mM NaF, and 0.1 mM sodium vanadate. 50 μg whole cell protein was subjected to sodium dodecyl sulfate-polyacrylamide gel electrophoresis (SDS-PAGE) in 10% polyacrylamide and then transferred onto a nitrocellulose membrane, which was processed following the manufacturers' instructions. The antibody reactions were detected by enhanced chemiluminescence using LUMIGLO (CELL SIGNALLING TECHNOLOGY).

Mitogen-Activated Protein (MAP) Kinase Assay.

A549 cells were infected with purified RSV and harvested at various times post infection, as specified. ERK-1/2 were immunoprecipitated and their kinase activity was tested using an Elk-1 fusion protein (CELL SIGNALING TECHNOLOGY, Beverly, Mass., USA). Elk-1 phosphorylation at Ser383 was determined by Western blot.

DNA Transfection.

WT and DN mutant MEK-1 has been described previously (Catling, A. D. et al. *Mol. Cell. Biol.*, 1995, 15: 5214-5225). In addition, plasmid DNA of WT and mutant STAT-1α was also used in other experiments. A549 cells grown in a 100 mm tissue culture plate to 70-80% confluence were transfected with 12 µg of DNA and 35 µl of Lipofectin (Life Technology) for 15 hours at 37° C. following the guidelines of the instruction manual. Cells were then infected with RSV for 30 minutes at 37° C. before cell protein was extracted.

Statistical Analysis.

Statistical significance was analyzed using Student's t-test for paired observations. A P<0.05 level of significance (two-sided) was utilized throughout.

EXAMPLE 6

RSV Exposure Induces ERK-1 and ERK-2 Phosphorylation in A549Epithelial Cells

Figure 6A:
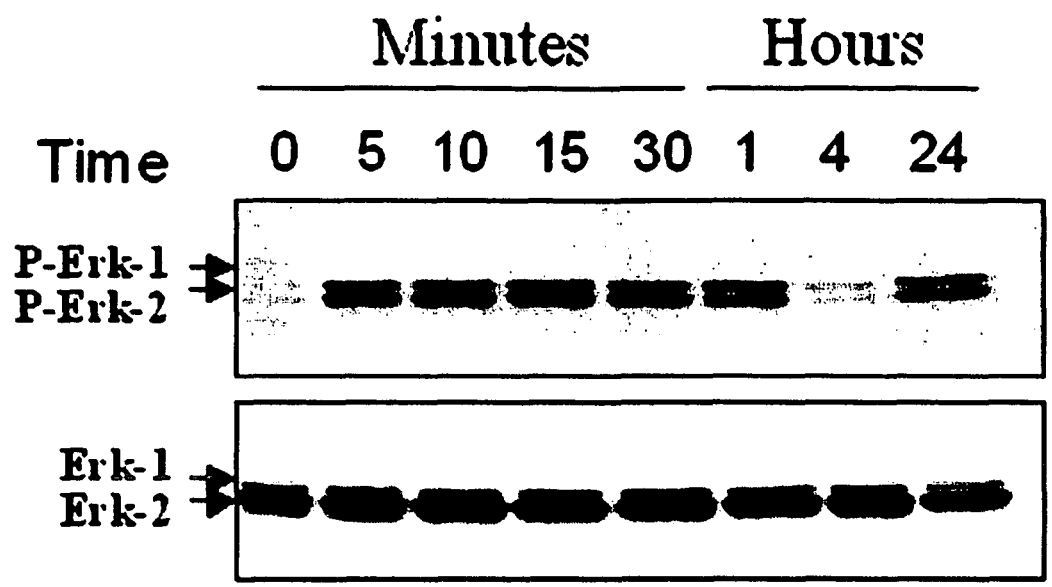
FIGS. 6A and 6B show that exposure to RSV activates ERK-1 and ERK-2 in A549 cells.
Figure 6B:
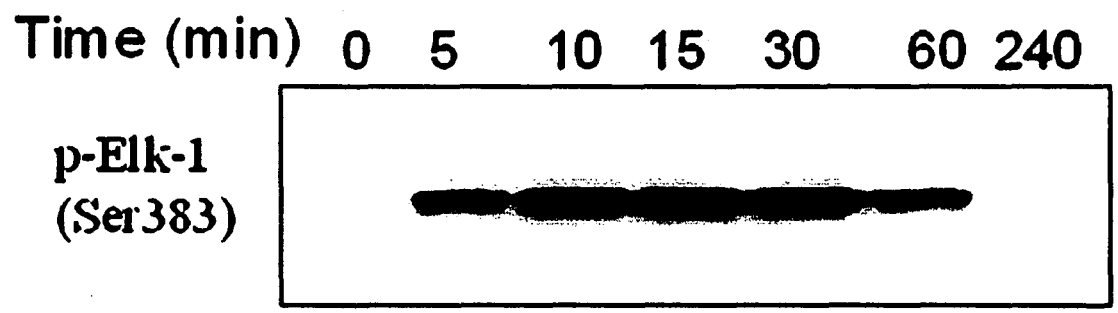
Figure 7:
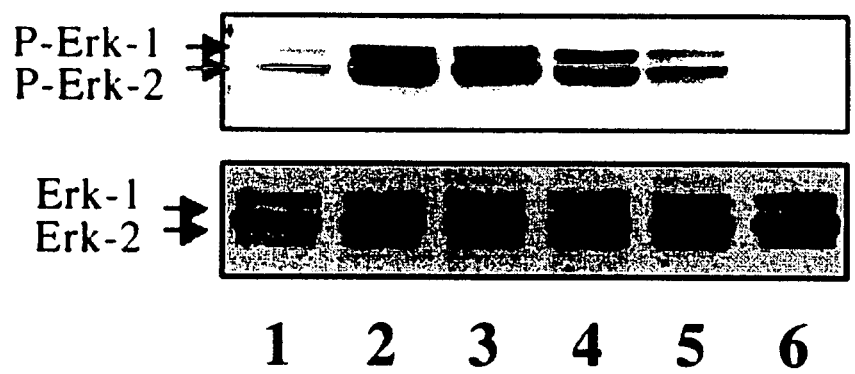
FIG. 7 shows the effect of heparin and heparinase on RSV-induced ERK-1/2 activation. Proteins were isolated from untreated cells (lane 1) or cells infected with RSV for 30 minutes (lanes 2-6) after pretreatment of cells for 30 minutes with heparinase (lane 3) or heparin (lane 5), or infected with virus pretreated with heparinase (lane 4) or heparin (lane 6) prior to addition to the cells. Proteins were separated by SDS-PAGE, blotted and probed with anti-phospho ERK-1/2 and then re-probed with anti-ERK-1/2.

RSV infection induced the increased phosphorylation of ERK-1 and ERK-2 in A549 cells, as demonstrated by Western blotting using corresponding antibodies and phosphoantibodies (FIG. 6A). The phosphorylation of the ERK-1 and ERK-2 was induced at 5 minutes post-RSV exposure and continued until 2 hours post RSV infection. At 4 hours following exposure to RSV, ERK-1 and ERK-2 phosphorylation was not detected; however, ERK-1 and ERK-2 phosphorylation reappeared at 24 hours after infection. Assays of A549 cells infected with sucrose-purified RSV at a multiplicity of infection of 1 confirmed that the rapid activation of ERK-1/2 is due to RSV per se and not to cytokines or growth factors (FIG. 6B). The rapid activation of ERK-1/2 suggested that RSV attachment is responsible for triggering the signaling. In fact, heparin, a known inhibitor of RSV attachment (Feldman, S. A. et al. *J. Virol.*, 1999, 73: 6610-6617; Bourgeois, C. et al. *J. Virol.*, 1998, 72: 7221-7227), abolished the RSV-induced activation of ERK-1/2 (FIG. 7).

EXAMPLE 7

ERK-1/2 Phosphorylation is Linked with Activation of STAT-1 K and of I κB

Figure 8A:
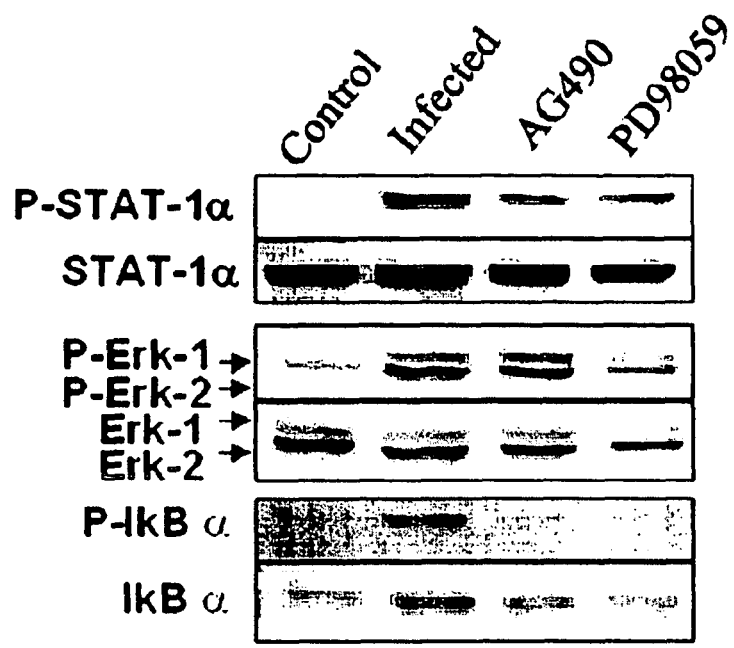
FIGS. 8A-8D show the effects of inhibitors of phosphorylation of STAT-1α and ERK-1/2.
Figure 8B:
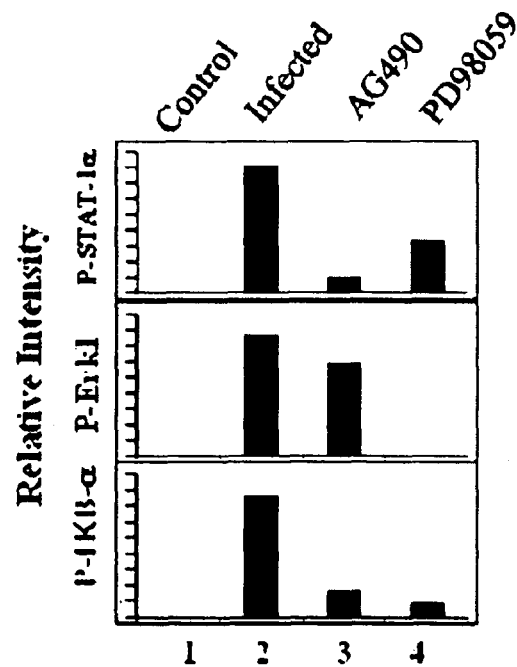
Figure 8C:
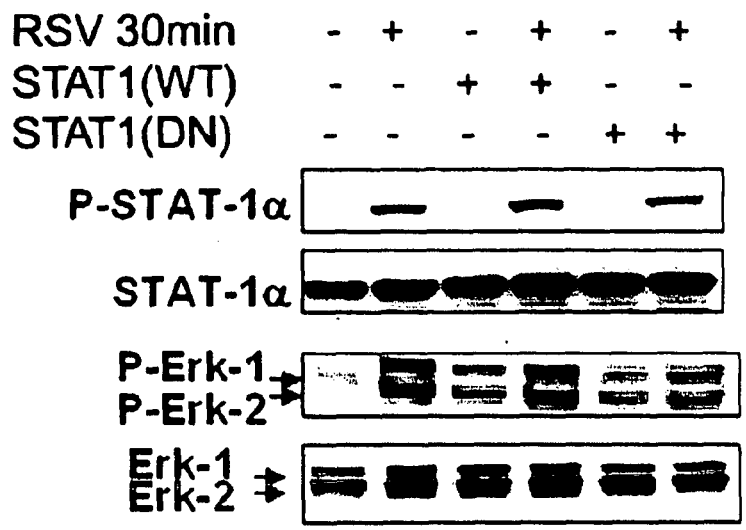
Figure 8D:
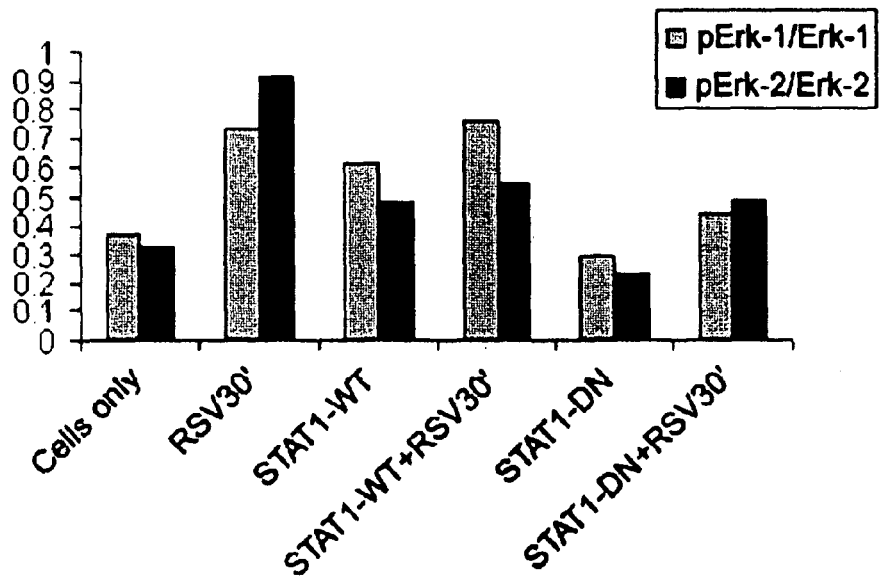

A549 cells exhibit activation of STAT-1α and STAT-3 and NF-κB following exposure to RSV (Kong, X. et al. *Biochem. Biophys. Res. Commun.*, 2003, 306: 616-622). Specific inhibitors to STAT-1K and ERK-1/2 pathways were used to determine if blocking one pathway affects the phosphorylation of both of them and IκBα (FIGS. 8A and 8B). A decrease in RSV-induced STAT-1K phosphorylation and in IκBα phosphorylation in cells pre-incubated with AG490 suggests a possible interaction between these two pathways. Although AG490 failed to inhibit ERK activation, PD98059 significantly affected the phosphorylation of both STAT-1α and IκB (FIG. 8B). To determine if phospho-STAT-1α is required for the increase in phospho-ERK-1/2 seen in RSV infection, cells were transfected with plasmids encoding either WT- or DN-STAT-1α. Both STAT-1α and ERK-1/2 phosphorylation decreased in cells transfected with DN STAT-1α compared to WT STAT-1α in response to RSV infection (FIG. 8C). Together, these results suggest that both STAT-1α and ERK-1/2 participate in the phosphorylation of each other as well as in phosphorylation of IκBα in the context of RSV infection.

EXAMPLE 8

Inhibition of ERKs Attenuates RSV Infection

Figure 9A:
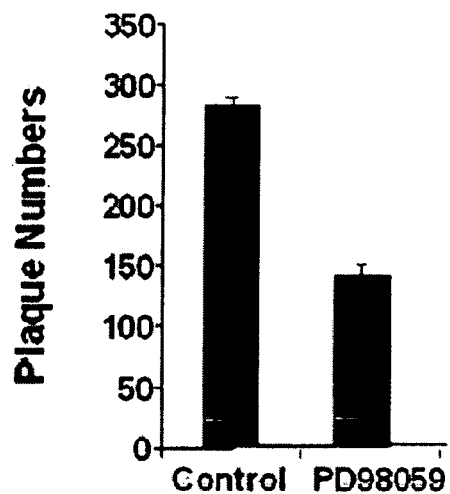
FIGS. 9A and 9B shows that inhibition of ERK-1/2 activation decreases RSV infection of A549 cells.
Figure 9B:
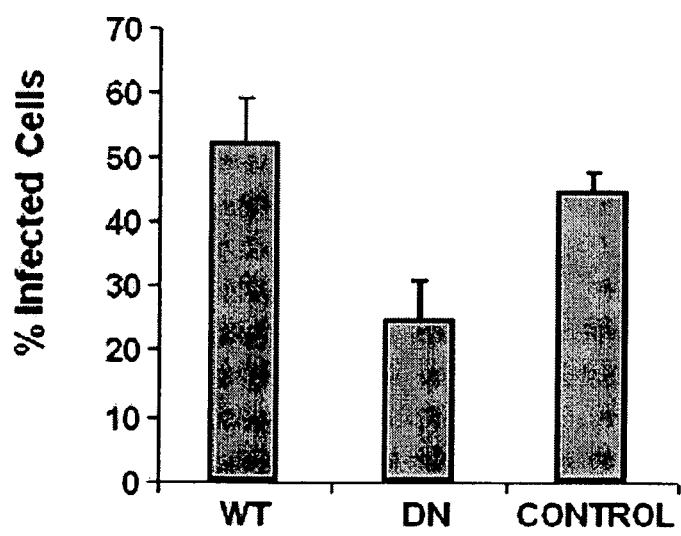
Figure 10A:
FIGS. 10A-10F show the effects of STAT and ERK-1/2 inhibitors on RSV infection of NHBE cells. NHBE cells were treated with either AG490 (50 µM) (FIGS. 10C and 10D) or PD98059 (80 µM) (FIGS. 10E and 10F) for 2 hours. DMSO was used as a mock control (FIGS. 10A and 10B). After inhibitor removal, cells were infected with rgRSV for 2 hours. Then, rgRSV was removed and growth medium with inhibitors was added to the cells for 16 hours before fluorescent images (DMSO, FIG. 10B; AG490, FIG. 10D; PD98059, FIG. 10F) as well as light transmission images (DMSO, FIG. 10A; AG490, FIG. 10C; PD98059, FIG. 10E) were taken.
Figure 10B:
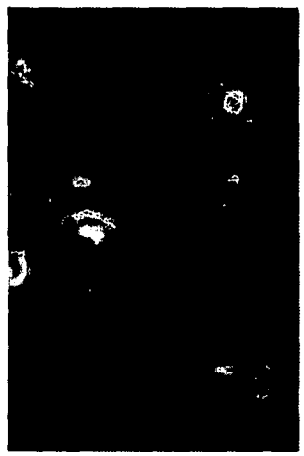
Figure 10C:
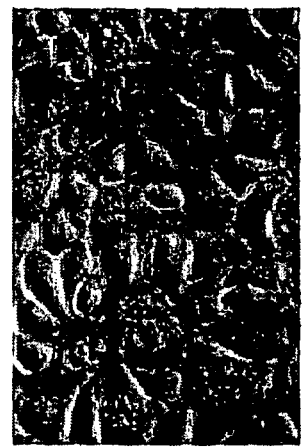
Figure 10D:
Figure 10E:
Figure 10F:
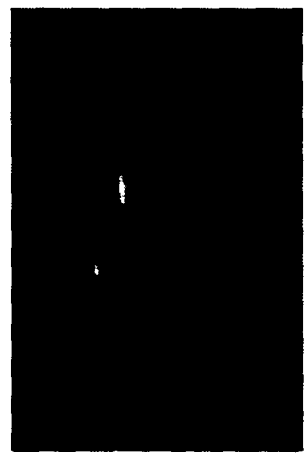

To examine whether ERKs play a specific role in RSV infection, A549 cells were treated with PD98059 and then infected with RSV. After 24 hours of RSV infection, there was a decrease in the percentage of infected cells treated with the inhibitor compared to those treated with control, suggesting that the ERK pathway plays a role during RSV infection (FIG. 9A). Moreover, the number of infected cells in DN MEK-1-transfected A549 cells was reduced in >60% compared to those transfected with a WT construct (FIG. 9B). These results indicate that ERK-1/2 pathway plays a role during the infection.

EXAMPLE 9

Requirement of STAT and ERK-1/2 Activation for Successful RSV Infection of Primary NHBE Cells To determine if both JAK-STAT-1α and ERK pathways are required for a successful RSV infection in primary NHBE cells, they were exposed to either AG490 or PD98059 before being infected with rgRSV. Exposure of NHBE to AG490 or PD98059 caused a significant reduction in the number of infected cells (FIG. 10A-10F). These results strongly suggest that JAK-STAT-1α and ERK-1/2 are required for a successful RSV infection in bronchial epithelial cells.

This study provides evidence in support of a rapid and transient activation of ERK-1/2 in RSV-infected A549 cells. Such activation appears to be dependent on the presence of phospho-STAT-1α and is required for both STAT-1α and IκBα phosphorylation. Results of studies using DN mutants and specific inhibitors indicate that ERK-1/2 activation is important for successful RSV infection. Also, ERK-1 and ERK-2 activation constitutes an integral pathway of early signaling cascades involved in RSV infection.

RSV was reported to activate ERK-2 at the early stages of infection (10 minutes after RSV exposure) and that such activation was required for IL-8 production (Chen, W. et al. *Exp. Lung Res.*, 2000, 26: 13-26). However, given that RSV supernatant contains a number of cytokines and chemokines which may activate ERK-2, the significance of this report was unclear. The present study tests ERK activity in A549 cells exposed to sucrose-purified RSV, and provides evidence of ERK-1 activation. The rapid activation of ERK-1 and ERK-2 is consistent with the finding that a number of genes are activated within 30 minutes of RSV infection (Kong, X. et al. *Biochem. Biophys. Res. Commun.*, 2003, 306: 616-622).

The rapid activation of ERK-1/2 after RSV infection led to the hypothesis that RSV attachment causes ERK signaling, which is supported by the fact that the heparin- or heparinase-treated RSV did not induce ERK-1/2 phosphorylation. Both RSV-G and -F proteins were reported to bind to heparin sulfate on the cell surface (Karger, A. et al. *J. Gen. Virol.*, 2001, 82: 631-640; Feldman, S. A. et al. *Arch. Virol.*, 2001, 146: 2369-2383; Techaarpornkul, S. et al. *Virology*, 2002, 294: 296-304). Interestingly, however, the treatment of A549 cells with heparinase, which abrogated STAT-1α phosphorylation, did not affect the phosphorylation of ERK-1/2. The reason for the segregation of signaling in heparinase-treated A549 cells after RSV exposure is unclear.

The fact that PD98059 and DN STAT-1α inhibited the phosphorylation of STAT and ERK pathways, respectively, suggests the existence of cross-talk between these pathways during RSV infection. Previously, Stancato et al. have reported that STAT-1 may scaffold signaling components required for activation of the Raf/MEK/ERK signaling cascade (Stancato, L. F. et al. *J. Biol. Chem.*, 1998, 273: 18701-18704).

Notably, STAT-1α activation is also required for NF-κB activation in infected cells evidenced by AG490 effect upon IκBα phosphorylation. This agrees with a previous report in which the JAK inhibition prevented the degradation of IκBα and blocked the translocation of NF-κB p65 into the nucleus (Cruz, M. T. et al. *Nitric Oxide,* 2001, 5: 53-61).

The evidence that inhibiting ERK significantly decreases RSV infection in A549 and NHBE cells suggests that this pathway may be important in turning on genes for virus replication and/or morphogenesis. To rule out the possibility that this effect on viral replication is due to diminished cell proliferation, viable cells were enumerated at 12, 24, 48, and 72 hours after treatment with inhibitors. The results showed no significant difference in cell numbers between treated and untreated cells (data not shown).

Involvement of ERKs in virus infection is not unprecedented. ERK pathway activation is required at different levels during HIV-1 infection. The association of ERK-2 with different HIV-1 strains derived from T cells and promonocytic cells has been reported (Cartier, C. et al. *J. Virol.,* 1997, 71: 4832-4837). ERK phosphorylates several HIV-1 proteins important for viral replication, such as Vif, Rev, Tat, p17 (Gag), and Nef (Yang, X. and Gabuzda, D. *J. Virol.,* 1999, 73: 3460-3466). HIV-1 infectivity is enhanced when cells are treated with ERK stimulators or when cells are transfected with activated forms of Ras, Raf, and MEK molecules (Yang, X. and Gabuzda, D. *J. Virol.,* 1999, 73: 3460-3466). In addition, specific inhibitors of the ERK pathway such as PD98059 reduced the infectivity of HIV-1 virions (Yang, X. and Gabuzda, D. *J. Virol.,* 1999, 73: 3460-3466). Finally, HIV-1 infection of brain microvascular endothelia is dependent on the activation of the ERK pathway and inhibition of this pathway repressed virus entry (Liu, N. Q. et al. *J. Virol.,* 2002, 76: 6689-6700).

In the same line, the ERK activation pathway is also required during the early stages of influenza infection. Inhibiting the normal process that conveys the activation of ERK impairs influenza virus replication because it affects the early stage of nuclear export of viral ribonucleoprotein, probably as a result of impaired activity of the viral nuclear export protein (Pleschka, S. et al. *Nat. Cell Biol.,* 2001, 3: 301-305; Ludwig, S. et al. *Trends Mol. Med.,* 2003, 9: 46-52).

In addition to impairing viral infection, there are other instances in which virus propagation could be affected by blocking the function of the ERK pathway. In the case of Borna disease virus, the ERK pathway seems to be required for the virus to spread to neighboring cells (Planz, O. et al. *J. Virol.,* 2001, 75: 4871-4877). Regarding viral pathogenesis, ERK activation has been implicated in the development of Visna virus infection-associated encephalitis, and if this pathway is inhibited, viral replication is abolished secondary to a defect in Rev function (Barber, S. A. et al. *J. Virol.,* 2002, 76: 817-828). Present evidence also indicates that hepatitis virus B, C, and E activate ERK through different means and take advantage of such activation as a strategy for their own survival (Panteva, M. et al. *Virus Res.,* 2003, 92: 131-140). In the early stages of infection, vaccinia virus triggers the activation of ERK through an unknown mechanism. Interestingly, when cells are exposed to inhibitors of the ERK pathway, the viral multiplication is impaired (de Magalhaes, J. C. et al. *J. Biol. Chem.,* 2001, 276: 38353-38360).

Taken together, all of these previous reports highlight the role the ERK pathway in the efficient infection and replication of certain virus species as well as how evolution has endowed these viruses to develop mechanisms that allowed them to sequester host cell signaling pathways. This study establishes for the first time that STAT-1α, and ERK-1/2 are required for successful RSV infection. The demonstration that RSV infection is inhibited in primary NHBE cells confirms the generality of the signaling requirement seen in A549 cells.

All patents, patent applications, provisional applications, and publications referred to or cited herein are incorporated by reference in their entirety, including all figures, tables, nucleic acid sequences, and amino acid sequences, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. A method for reducing respiratory syncytial virus (RSV) infection of respiratory epithelial cells in a mammalian subject suffering from an RSV infection, comprising administering an effective amount of an inhibitor of the janus kinase (JAK)/signal transducer and activator of transcription (STAT) signaling pathway or the mitogen-activated kinase (MAPK)/extracellular signal-regulated kinase (ERK) signaling pathway to the respiratory epithelial cells.

2. The method of claim 1, further comprising determining whether the subject is suffering from an RSV infection before or after said administering.

3. The method of claim 1, wherein the subject is a non-human mammal.

4. The method of claim 1, wherein the subject is human.

5. The method of claim 1, wherein the inhibitor is administered intranasally or orally.

6. The method of claim 1, wherein the inhibitor is administered intranasally as an aerosol or drops.

7. The method of claim 1, wherein the inhibitor is administered with an agent that promotes internalization of the inhibitor by the subject's respiratory epithelial cells.

8. The method of claim 1, wherein the inhibitor is an agent selected from the group consisting of a polynucleotide, polypeptide, antibody, and small molecule.

9. The method of claim 1, wherein the inhibitor is a polynucleotide, and wherein the polynucleotide encodes a polypeptide which, when expressed, inhibits JAK/STAT or MAPK/ERK signaling within the subject.

10. The method of claim 1, wherein the inhibitor is a polynucleotide, and wherein the polynucleotide is an antisense molecule or a small interfering RNA (siRNA) molecule.

11. The method of claim 10, wherein the polynucleotide reduces expression of STAT-1 or STAT-3 within the subject.

12. The method of claim 10, wherein the polynucleotide reduces expression of ERK1 or ERK2 within the subject.

13. The method of claim 1, wherein the inhibitor is a polynucleotide, and wherein the polynucleotide is administered to the subject within a vector.

14. The method of claim 1, wherein the inhibitor is a JAK/STAT signaling inhibitor selected from the group consisting of AG490, PIAS protein, cytokine-inducible Src homology 2-containing (CIS) protein, CIS-related protein, suppressor of cytokine signaling-I protein (SOCS-1), tyrphostin, 4,5-dimethoxy-2-nitrobenzoic acid, 4,5-dimethoxy-2-nitrobenzamide, 4-(phenyl)-amino-6,7-dimethoxyquinazoline, 4-(4'-hydroxyphenyl)-amino-6,7-dimethoxyquinazoline, 4-(3'-bromo-4'-hydroxylphenyl)-amino-6,7-dimethoxyquinalzoline, forskolin, and 3-isobutyl-1-methylxanthine (IBMX).

15. The method of claim 1, wherein the inhibitor is a MAPK/ERK signaling inhibitor selected from the group consisting of GW5074, BAY 43-9006, ISIS 5132, PD98059, PD184352, U0126, Ro 09-2210, L-783,277, purvalanol, and imidazolium trans-imidazoledimethyl sulfoxide-tetrachlororuthenate (NAMI-A).

16. A method for reducing respiratory syncytial virus (RSV) infection of respiratory epithelial cells in a human subject suffering from an RSV infection, comprising orally or intranasally administering an effective amount of an inhibitor of the janus kinase (JAK)/signal transducer and activator of transcription (STAT) signaling pathway or the mitogen-activated kinase (MAPK)/extracellular signal-regulated kinase (ERK) signaling pathway to the respiratory epithelial cells.

17. The method of claim 1, further comprising administering an anti-viral agent to the subject.

18. The method of claim 16, further comprising determining whether the subject is suffering from an RSV infection before or after said administering.

19. The method of claim 16, further comprising administering an anti-viral agent to the subject.

20. The method of claim 1, wherein the inhibitor inhibits STAT-1 signaling in the respiratory epithelial cells.

21. The method of claim 1, wherein the inhibitor inhibits STAT-3 signaling in the respiratory epithelial cells.

22. The method of claim 16, wherein the inhibitor inhibits STAT-1 signaling in the respiratory epithelial cells.

23. The method of claim 16, wherein the inhibitor inhibits STAT-3 signaling in the respiratory epithelial cells.

24. The method of claim 1, wherein the inhibitor inhibits ERK1 signaling in the respiratory epithelial cells.

25. The method of claim 1, where in the inhibitor inhibits ERK2 signaling in the respiratory epithelial cells.

26. The method of claim 16, wherein the inhibitor inhibits ERK1 signaling in the respiratory epithelial cells.

27. The method of claim 16, where in the inhibitor inhibits ERK2 signaling in the respiratory epithelial cells.

* * * * *

UNITED STATES PATENT AND TRADEMARK OFFICE
CERTIFICATE OF CORRECTION

PATENT NO. : 8,592,368 B2  
APPLICATION NO. : 11/018954  
DATED : November 26, 2013  
INVENTOR(S) : Shyam S. Mohapatra It is certified that error appears in the above-identified patent and that said Letters Patent is hereby corrected as shown below:

In the Specification

Column 23,
Line 7, "(mRNAs)" should read --(miRNAs)--

Column 23,
Line 10, "mRNAs" should read --miRNAs--

Column 23,
Lines 13-14, "MRNA precursor with RNA" should read --miRNA precursor with miRNA--

Column 23,
Line 15, "mRNA" should read --miRNA--

Signed and Sealed this  
Fifteenth Day of April, 2014

Michelle K. Lee  
*Deputy Director of the United States Patent and Trademark Office*

SEQUENCE LISTING

<160> NUMBER OF SEQ ID NOS: 19

<210> SEQ ID NO 1
<211> LENGTH: 22
<212> TYPE: DNA
<213> ORGANISM: Artificial Sequence
<220> FEATURE:
<223> OTHER INFORMATION: forward primer Egr-1-fp

<400> SEQUENCE: 1
ccccttcccc aattactatt cc            22

<210> SEQ ID NO 2
<211> LENGTH: 20
<212> TYPE: DNA
<213> ORGANISM: Artificial Sequence
<220> FEATURE:
<223> OTHER INFORMATION: reverse primer Egr-1-rp

<400> SEQUENCE: 2
ccaagtgagg acctaactcc              20

<210> SEQ ID NO 3

```
<211> LENGTH: 19
<212> TYPE: DNA
<213> ORGANISM: Artificial Sequence
<220> FEATURE:
<223> OTHER INFORMATION: forward primer cFos-fp

<400> SEQUENCE: 3
ccttcgtctt cacctaccc                                                    19

<210> SEQ ID NO 4
<211> LENGTH: 22
<212> TYPE: DNA
<213> ORGANISM: Artificial Sequence
<220> FEATURE:
<223> OTHER INFORMATION: reverse primer cFos-rp

<400> SEQUENCE: 4
gaagaggtaa ggacttgagt cc                                                22

<210> SEQ ID NO 5
<211> LENGTH: 22
<212> TYPE: DNA
<213> ORGANISM: Artificial Sequence
<220> FEATURE:
<223> OTHER INFORMATION: forward primer ZFTF-fp

<400> SEQUENCE: 5
ttctgagtga caaagtgact gc                                                22

<210> SEQ ID NO 6
<211> LENGTH: 21
<212> TYPE: DNA
<213> ORGANISM: Artificial Sequence
<220> FEATURE:
<223> OTHER INFORMATION: reverse primer ZFTF-rp

<400> SEQUENCE: 6
taggagacag atttgggcag g                                                 21

<210> SEQ ID NO 7
<211> LENGTH: 18
<212> TYPE: DNA
<213> ORGANISM: Artificial Sequence
<220> FEATURE:
<223> OTHER INFORMATION: forward primer beta-actin-fp

<400> SEQUENCE: 7
cgcgagaaga tgacccag                                                     18

<210> SEQ ID NO 8
<211> LENGTH: 18
<212> TYPE: DNA
<213> ORGANISM: Artificial Sequence
<220> FEATURE:
<223> OTHER INFORMATION: reverse primer beta-actin-rp

<400> SEQUENCE: 8
atcacgatgc cagtggta                                                     18

<210> SEQ ID NO 9
<211> LENGTH: 19
<212> TYPE: DNA
<213> ORGANISM: Artificial Sequence
<220> FEATURE:
<223> OTHER INFORMATION: forward primer IL6-fp

<400> SEQUENCE: 9
```

```
aactccttct ccacaagcg                                                    19

<210> SEQ ID NO 10
<211> LENGTH: 19
<212> TYPE: DNA
<213> ORGANISM: Artificial Sequence
<220> FEATURE:
<223> OTHER INFORMATION: reverse primer IL6-rp

<400> SEQUENCE: 10
tggactgcag gaactcctt                                                    19

<210> SEQ ID NO 11
<211> LENGTH: 22
<212> TYPE: DNA
<213> ORGANISM: Artificial Sequence
<220> FEATURE:
<223> OTHER INFORMATION: forward primer RSV N-fp

<400> SEQUENCE: 11
gcgatgtcta ggttaggaag aa                                                22

<210> SEQ ID NO 12
<211> LENGTH: 24
<212> TYPE: DNA
<213> ORGANISM: Artificial Sequence
<220> FEATURE:
<223> OTHER INFORMATION: reverse primer RSV N-rp

<400> SEQUENCE: 12
gctatgtcct tgggtagtaa gcct                                              24

<210> SEQ ID NO 13
<211> LENGTH: 24
<212> TYPE: DNA
<213> ORGANISM: Artificial Sequence
<220> FEATURE:
<223> OTHER INFORMATION: Sis-inducible element SIE

<400> SEQUENCE: 13
agcttcattt cccgtaaatc ccta                                              24

<210> SEQ ID NO 14
<211> LENGTH: 13
<212> TYPE: PRT
<213> ORGANISM: Artificial Sequence
<220> FEATURE:
<223> OTHER INFORMATION: peptide inhibitor of ERK1/2 activation

<400> SEQUENCE: 14

Met Pro Lys Lys Lys Pro Thr Pro Ile Gln Leu Asn Pro
1               5                   10

<210> SEQ ID NO 15
<211> LENGTH: 7
<212> TYPE: PRT
<213> ORGANISM: Artificial Sequence
<220> FEATURE:
<223> OTHER INFORMATION: nuclear localization signal (NLS)

<400> SEQUENCE: 15

Pro Lys Lys Lys Arg Lys Val
1               5

<210> SEQ ID NO 16
<211> LENGTH: 6
<212> TYPE: PRT
```

```
<213> ORGANISM: Artificial Sequence
<220> FEATURE:
<223> OTHER INFORMATION: nuclear localization signal (NLS)

<400> SEQUENCE: 16

Ala Arg Arg Arg Arg Pro
1               5

<210> SEQ ID NO 17
<211> LENGTH: 10
<212> TYPE: PRT
<213> ORGANISM: Artificial Sequence
<220> FEATURE:
<223> OTHER INFORMATION: nuclear localization signal (NLS)

<400> SEQUENCE: 17

Glu Glu Val Gln Arg Lys Arg Gln Lys Leu
1               5                   10

<210> SEQ ID NO 18
<211> LENGTH: 9
<212> TYPE: PRT
<213> ORGANISM: Artificial Sequence
<220> FEATURE:
<223> OTHER INFORMATION: nuclear localization signal (NLS)

<400> SEQUENCE: 18

Glu Glu Lys Arg Lys Arg Thr Tyr Glu
1               5

<210> SEQ ID NO 19
<211> LENGTH: 20
<212> TYPE: PRT
<213> ORGANISM: Artificial Sequence
<220> FEATURE:
<223> OTHER INFORMATION: nuclear localization signal (NLS)

<400> SEQUENCE: 19

Ala Val Lys Arg Pro Ala Ala Thr Lys Lys Ala Gly Gln Ala Lys Lys
1               5                   10                  15

Lys Lys Leu Asp
            20
```